(12) United States Patent
Woolf et al.

(10) Patent No.: US 9,193,783 B2
(45) Date of Patent: *Nov. 24, 2015

(54) DRG11-RESPONSIVE (DRAGON) POLYPEPTIDES

(75) Inventors: Clifford J. Woolf, Newton, MA (US); Tarek A. Samad, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 740 days.

This patent is subject to a terminal disclaimer.

(21) Appl. No.: 13/407,497

(22) Filed: Feb. 28, 2012

(65) Prior Publication Data

US 2012/0204281 A1 Aug. 9, 2012

Related U.S. Application Data

(60) Continuation of application No. 13/281,510, filed on Oct. 26, 2011, which is a continuation of application No. 12/509,951, filed on Jul. 27, 2009, now abandoned, which is a division of application No. 11/230,180, filed on Sep. 19, 2005, now abandoned, which is a division of application No. 10/419,296, filed on Apr. 17, 2003, now Pat. No. 7,319,138.

(60) Provisional application No. 60/373,519, filed on Apr. 18, 2002.

(51) Int. Cl.

| C07K 14/475 | (2006.01) |
|---|---|
| A61K 38/18 | (2006.01) |
| C07K 16/18 | (2006.01) |
| C07K 14/435 | (2006.01) |
| C07K 14/46 | (2006.01) |
| C07K 14/47 | (2006.01) |
| A61K 38/00 | (2006.01) |

(52) U.S. Cl.
CPC ........... *C07K 16/18* (2013.01); *C07K 14/43509* (2013.01); *C07K 14/461* (2013.01); *C07K 14/47* (2013.01); *A01K 2217/05* (2013.01); *A01K 2217/075* (2013.01); *A61K 38/00* (2013.01); *C07K 2317/92* (2013.01)

(58) Field of Classification Search
None
See application file for complete search history.

(56) References Cited

U.S. PATENT DOCUMENTS

| 5,011,912 | A | 4/1991 | Hopp et al. |
|---|---|---|---|
| 6,046,319 | A | 4/2000 | Power et al. |
| 6,090,621 | A | 7/2000 | Kavanaugh et al. |
| 6,800,455 | B2 | 10/2004 | Stanton et al. |
| 6,821,724 | B1 | 11/2004 | Mittman et al. |
| 6,943,241 | B2 | 9/2005 | Isogai et al. |
| 7,166,573 | B1 | 1/2007 | Obata |
| 7,511,018 | B2 | 3/2009 | Goldberg et al. |
| 7,534,764 | B2 | 5/2009 | Ganz et al. |
| 2002/0110804 | A1 | 8/2002 | Stanton et al. |
| 2004/0010134 | A1 | 1/2004 | Rosen et al. |
| 2004/0014141 | A1 | 1/2004 | Woolf et al. |
| 2004/0102376 | A1 | 5/2004 | Mueller et al. |
| 2004/0248249 | A1 | 12/2004 | Tran et al. |
| 2006/0035263 | A1 | 2/2006 | Woolf et al. |
| 2006/0063208 | A1 | 3/2006 | Woolf et al. |
| 2007/0231863 | A1 | 10/2007 | Woolf et al. |
| 2007/0259816 | A1 | 11/2007 | Woolf et al. |

FOREIGN PATENT DOCUMENTS

| EP | 1130094 A2 | 9/2001 |
|---|---|---|
| WO | 00/73801 A2 | 12/2000 |
| WO | 01/54708 A1 | 8/2001 |
| WO | 02/051438 A2 | 7/2002 |
| WO | 03/004615 A2 | 1/2003 |

OTHER PUBLICATIONS

Non-Final Office Action dated Feb. 10, 2014 issued in U.S. Appl. No. 13/281,510, filed Oct. 26, 2011.
AZ602846 (NCBI website Dec. 13, 2000) '1M0421L17R Mouse 10kb plasmid UUGC1M library Mus musculus genomic clone UUGC1M0421L17 R, genomic survey sequence'.
Non-Final Office Action dated Jul. 2, 2013, issued in related U.S. Appl. No. 13/407,491, filed Feb. 28, 2012.
Final Office Action dated May 13, 2013, issued in related U.S. Appl. No. 13/281,510, filed Oct. 26, 2011.
Office Action Issued in U.S. Appl. No. 13/281,510, dated Jun. 18, 2014 (13 pages).
Anderson, "Cellular and molecular biology of neural crest cell lineage determination." Trends Genet 13:276-280 (1997).
Anderson, "Lineages and transcription factors in the specification of vertebrate primary sensory neurons." Guff. Opin. Neurobiol. 9:517-524 (1999).
Babitt et al, J. Biol. Chem., 280(33):29820-29827 (2005).
Babitt et al.., NAT. GENET., 38(5):531-539 (2006).
Bell et al., "Dynamic domains of gene expression in the early avian forebrain." Dev. Biol. 236:76-88 (2001).
Benson et al., "Molecules, maps and synapse specificity." Nat, Rev. Neurosci. 2:899-909 (2001).
Bork et at (1996). "Go hunting in sequence databases but watch out for the traps." Trends in Genetics. 12 (10):425-427.
Bork, A. (2000). "Powers and pitfalls in sequence analysis: the 70% hurdle." Genome Res. 10:398-400.
Brenner, S.E. (1999). "Errors in genome function." Trends in Genetics. 15(4):132-133.
Brose et al., "Slit proteins bind Robo receptors and have an evolutionarily conserved role in repulsive axon guidance." Cell 96:795-806 (1999).

(Continued)

*Primary Examiner* — Christine J Saoud
*Assistant Examiner* — Jon M Lockard
(74) *Attorney, Agent, or Firm* — Lathrop & Gage LLP

(57) ABSTRACT

This invention features methods and compositions useful for treating and diagnosing diseases of the nervous system, retina, skin, muscle, joint, and cartilage using a Dragon family protein. Protein and nucleic acid sequences of human, murine, zebrafish, and *C. elegans* Dragon family members are also disclosed.

4 Claims, 21 Drawing Sheets

(56) References Cited

OTHER PUBLICATIONS

Brose et al., "Slit proteins: key regulators of axon guidance, axonal branching, and cell migration." Cuff. Opin. Neurobiol. 10:95-102 (2000).

Chen et al, "The paired homeodomain protein DRG11 is required for the projection of cutaneous sensory afferent fibers to the dorsal spinal cord." Neuron 31:59-73 (2001).

Cheng et al., "Plexin-a3 mediates semaphorin signaling and regulates the development of hippocampal axonal projections." Neuron 32:249-263 (2001).

Chin, "On the Preparation and Utilization of Isolated and Purified Oligonucleotides." Katherine R. Everett Law Library, University of North Carolina, Chapel Hill, NC, CD ROM (2002).

Chin, "On the Preparation and Utilization of Isolated and Purified Oligonucelotides." Katherine R. Everett Law Library, University of North Carolina, Chapel Hill, NC, Text Description of Contents and Hard Copy of Initial Portion of the Text File on CD ROM (2002).

Cross et al., "Isolation of CpG islands from large genomic clones." Nucleic Acids Res. 27:2099-2107 (1999).

Cross et al., "Purification of CpG Islands using a methylated DNA binding column." Nat. Genet. 6:236-244 (1994).

Database NCBI, Auffray C. et al., NCBI Accession No. CAB 98207, Jul. 2000.

Database TrEMBL Q95XN8, Du et al., The sequence of C. elegans cosmid Y71G12B, Dec. 2001.

Doerks et al. (1998). "Protein annotation: detective work for function prediction." Trends in Genetics, 14(6):248-250.

Emahazion et al. 2001 Trends in Genetics vol. 17 p. 407.

Enomoto et al., "RET signaling is essential for migration, axonal growth and axon guidance of developing sympathetic neurons." Development 128:3963-3974 (2001).

Frisen et al., "Ephrin-A5 (AL-1/RAGS) is essential for proper retinal axon guidance and topographic mapping in the mammalian visual system." Neuron 20:235-243 (1998).

Filip et al. (2004). "Issues in stem cell plasticity." J. Cell. Mol. Med. 8(4):572-577.

Hao et al., "C. elegans slit acts in midline, dorsal-ventral, and anterior-posterior guidance via the SAX-3lRobo receptor." Neuron 32:25-38 (2001).

Hirschhorn et al. Genetics in Medicine 2002 vol. 4 p. 45.

Hu et al., "Plexin B mediates axon guidance in drosophila by simultaneously inhibiting active Rac and enhancing RhoA signaling." Neuron 32:39-51 (2001).

International Search Report for PCT/US03/12079 dated Mar. 21, 2004.

Ioannidis et al. 2001 Nature Genetics VO1. 29 p. 306.

Jessell et al., "Development. The decade of the developing brain." CWT. Opin. Neumbiol. 10:599-611 (2000).

Jessell, "Neuronal specification in the spinal cord: Inductive signals and transcriptional codes." Nat. Rev. Genet. 1:20-29 (2000).

Liu et al., "Semaphorin-mediated axonal guidance via Rho-related G proteins." Curl. Opin. Cell. Bloi. 13:619-626 (2001).

Lo et al., "Specification of neurotransmitter identity by Phox2 proteins in neural crest stem cells." Neuron 22:693-705 (1999).

Lucentini, The Scientist 2004 p. 20.

Lundquist et al., "Three C. elegans Rac proteins and several alternative Rac regulators control axon guidance, cell migration and apoptotic cell phagocytosis." Development 128:4475-4488 (2001).

Mikayama et al. (1993). "Molecular cloning and functional expression of a cDNA encoding glycosylation-inhibiting factor." Proc.Natl. Acad. Sci. USA. 90:10056-10060.

Monnier et al., "RGM is a repulsive guidance molecule for retinal axons." Nature 419:392-395 (2002).

Muller et al., "Chromophore-assisted laser inactivation of a repulsive axonal guidance molecule." Curr. Biol. 6:1497-1502 (1996).

Mueller et al., "RGM, a repulsive guidance molecule, is involved in retinal axon guidance in vitro." Taniguchi Symposia on Brain Sci. 20:215-229 (1997).

Ngo et al. (1994). "Computational complexity, protein structure prediction, and the Levinthal paradox." In Merz and Le Grand (Eds.) The Protein Folding Problem and Tertiary Structure Prediction. Birkhauser:Boston, pp. 492-495.

Ogura, et al. "Evidence for two distinct retinoic acid response pathways for HOXB1 gene regulation." Proc Natl. Acad. Sci. USA 92:392-396 (1995).

Saito, et al. "Identification by differential RT-PCR of a novel paired homeodomain protein specifically expressed in sensory neurons and a subset of their CNS targets." Mol. Cell. Neuroscl. 6:280-292 (1995).

Samad et al., "DRAGON: a member of the Repulsive Guidance Molecule-related family of neuronal- and muscle-expressed membrane proteins is regulated by DRG11 and has neuronal adhesive properties." J. Neurosci. 24:2027-2036 (2004).

Samad et al., "DRAGON, a Bone Morphogenetic Protein co-receptor." J. Biol. Chem. 280:14122-14129 (2005).

Skolnick et al. (2000). "From genes to protein structure and function: novel applications of computational approaches in the genomic era." Trends in Biotech. 18(1):34-39.

Smith et al. (1997). "The challenges of genome sequence annotation or The devil is in the details." Nature Biotech. 15:1222-1223.

Supplementary Partial European Search Report for EP 03 72 8442 dated Mar. 17, 2006.

Waténabe, et at. "Isolation of estrogen-responsive genes with a CpG island library." Mol. and Cell. Biol. 18:442-449 (1998).

Wells, J.A. (1990). "Additivity of mutational effects in proteins." Biochemistry. 29(37):8509-8517.

Xia et al., "Localization and action of Dragon (Repulsive Guidance Molecule b), a novel Bone Morphogenetic Protein coreceptor, throughout the reproductive axis." Endocrinology 146:3614-3621 (2005).

Office Action corresponding to U.S. Appl. No. 14/307,264, mailed Apr. 23, 2015.

Office Action corresponding to U.S. Appl. No. 14/307,250, mailed Apr. 6, 2015.

Genomic Screening for Target Genes

FIG. 1B

```
   1 - AGACCTGCATGGACGGGCATGGGCGTGAGAGCAGCACCTTCCTGCGCCGCCGCCCCCGCC -   60
     -                    M  G  V  R  A  A  P  S  C  A  A  A  P  A
  61 - GCCGCCGGGGCTGAGCAGTCCCGCCGCCCCGGGCTCTGGCCGCCGTCGCCCCCGCCGCCG -  120
     - A  A  G  A  E  Q  S  R  R  P  G  L  W  P  P  S  P  P  P  P
 121 - CTGTTGCTGCTGCTGCTGCTCAGCCTTGGGCTGCTCCACGCAGGTGATTGCCAACAGCCT -  180
     - L  L  L  L  L  L  L  S  L  G  L  L  H  A  G  D  C  Q  Q  P
 181 - ACTCAATGCCGAATCCAGAAATGTACCACAGACTTCGTGGCCCTGACTGCACACCTGAAC -  240
     - T  Q  C  R  I  Q  K  C  T  T  D  F  V  A  L  T  A  H  L  N
 241 - TCTGCCGCTGATGGGTTTGACTCTGAGTTTTGCAAGGCACTTCGCGCCTATGCTGGCTGC -  300
     - S  A  A  D  G  F  D  S  E  F  C  K  A  L  R  A  Y  A  G  C
 301 - ACCCAGCGAACTTCAAAGGCCTGCCGAGGCAACCTGGTGTACCATTCTGCTGTGTTAGGC -  360
     - T  Q  R  T  S  K  A  C  R  G  N  L  V  Y  H  S  A  V  L  G
 361 - ATCAGTGATCTCATGAGCCAGAGGAACTGTTCCAAGGATGGACCCACATCTTCCACCAAT -  420
     - I  S  D  L  M  S  Q  R  N  C  S  K  D  G  P  T  S  S  T  N
 421 - CCGGAAGTGACCCATGACCCCTGTAACTACCACAGCCACGGGGGAGTCAGAGAACATGGG -  480
     - P  E  V  T  H  D  P  C  N  Y  H  S  H  G  G  V  R  E  H  G
 481 - GGAGGGGACCAGAGACCCTCCCAATTACCTTTTCTGTGGCTTGTTTGGAGACCCTCACCTT -  540
     - G  G  D  Q  R  P  P  N  Y  L  F  C  G  L  F  G  D  P  H  L
 541 - CGAACTTTCAAGGATCACTTCCAGACATGCAAAGTGGAAGGGGCCTGGCCACTCATAGAC -  600
     - R  T  F  K  D  H  F  Q  T  C  K  V  E  G  A  W  P  L  I  D
 601 - AACAATTACCTTTCGGTTCAAGTGACGAACGTGCCTGTGGTCCCCGGGTCCAGTGCAACT -  660
     - N  N  Y  L  S  V  Q  V  T  N  V  P  V  V  P  G  S  S  A  T
 661 - GCTACAAACAAGGTCACGATTATCTTCAAAGCACAGCACGAGTGCACGGATCAGAAGGTG -  720
     - A  T  N  K  V  T  I  I  F  K  A  Q  H  E  C  T  D  Q  K  V
 721 - TACCAAGCTGTGACAGATGACCTGCCGGCCGCCTTTGTAGATGGCACCACCAGTGGGGGG -  780
     - Y  Q  A  V  T  D  D  L  P  A  A  F  V  D  G  T  T  S  G  G
 781 - GACGGTGACGTGAAGAGTCTTCACATCGTGGAGAAGGAGAGTGGCCGCTACGTAGAGATG -  840
     - D  G  D  V  K  S  L  H  I  V  E  K  E  S  G  R  Y  V  E  M
 841 - CATGCCCGCTACATAGGCACCACAGTGTTTGTGCGACAGCTGGGTCGCTACCTAACCCTC -  900
     - H  A  R  Y  I  G  T  T  V  F  V  R  Q  L  G  R  Y  L  T  L
 901 - GCTATCCGGATGCCCGAAGACTTGGCCATGTCCTATGAGGAAAGCCAGGACTTGCAGCTG -  960
     - A  I  R  M  P  E  D  L  A  M  S  Y  E  E  S  Q  D  L  Q  L
 961 - TGTGTGAATGGCTGCCCCATGAGTGAATGCATTGATGATGGACAAGGCCAGGTGTCTGCT - 1020
     - C  V  N  G  C  P  M  S  E  C  I  D  D  G  Q  G  Q  V  S  A
1021 - ATCCTGGGGCACAGCCTGCCTCACACCACCTCAGTGCAGGCCTGGCCTGGCTACACACTG - 1080
     - I  L  G  H  S  L  P  H  T  T  S  V  Q  A  W  P  G  Y  T  L
1081 - GAGACTGCCAGCACCCAATGCCACGAGAAGATGCCGGTGAAGGACATCTATTTCCAATCG - 1140
     - E  T  A  S  T  Q  C  H  E  K  M  P  V  K  D  I  Y  F  Q  S
1141 - TGTGTCTTCGACCTGCTCACCACTGGTGATGCCAACTTTACTGCTGCAGCCCACAGTGCC - 1200
     - C  V  F  D  L  L  T  T  G  D  A  N  F  T  A  A  A  H  S  A
1201 - TTGGAGGATGTGGAAGCGCTGCACCCAAGAAAGGAACGCTGGCACATCTTCCCCAGCAGC - 1260
     - L  E  D  V  E  A  L  H  P  R  K  E  R  W  H  I  F  P  S  S
1261 - TGTGGGGGATGTAGGGATTTGCCTGTTGGTCTTGGACTCACATGCTTGATCCTTATTATG - 1320
     - C  G  G  C  R  D  L  P  V  G  L  G  L  T  C  L  I  L  I  M
1321 - TTTTTGTAG - 1329
     - F  L  *
```

DRAGON protein structure:

N-terminus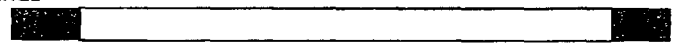C-terminus

Signal peptide                                 GPI-anchor

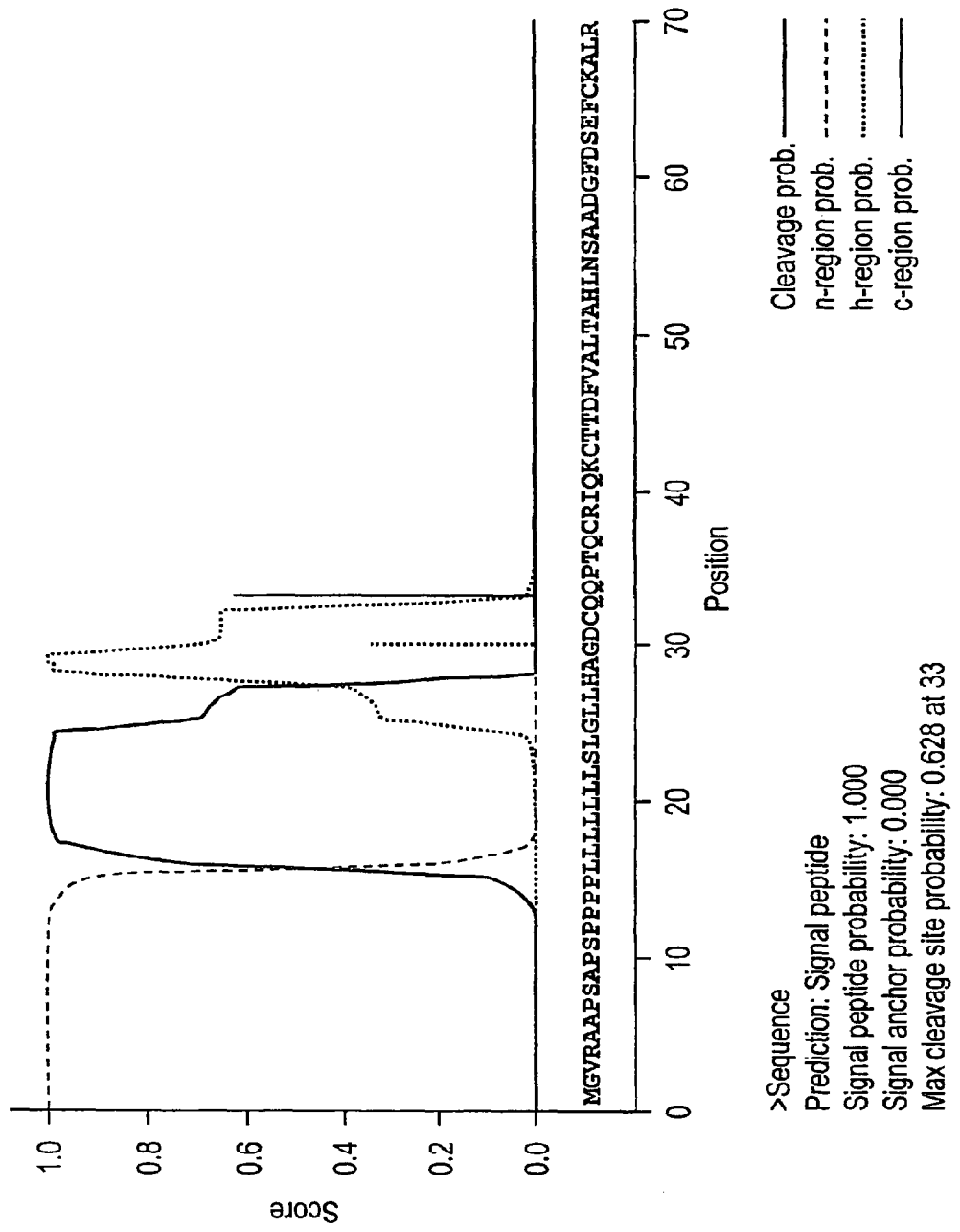

FIG. 3

```
mDRAGON    PSPPPPLLILLLSLGLLHAGD--------CQQPTQCRIQKCTTDFVALTAHL
           P PPPPLL LL L LL A              C  T  R+  C    VA A +
IGFBP      PLPPPPLLPLLPLLLLLGASGGGGGARAEVLFRCPPCTPERLAACGPPVAPPAAV mDRAGON    NSAADGFDSEFCKALR------AYAGCTQRTSKAC--------RGNLVY--HSAVLGISDL
           + A G           + R       + C +    +AC              +G   Y    + L + L
IGFBP      AAVAGGARMPCAELVRERGCGCCSVCARLEGEACGVYTPRCGQGLRCYPHPGSELPLQAL
```

FIG. 4

```
mDRAGON    -MSQRNCSKDGPTS-STNPEVTHDPCNYHSHGGVREH 134
           M +   C K        +PE    D    + HS GG+ E+
EPHB3      VMGEGTCEKRRDAEYGASPEQVADNGDDHSEGGLVEN 164 mDRAGON    PPSPPP---PLLL-LLLLSLGLLHAGDCQQPTQCRIQ-KCTTDFVALTAHLNSAAD---G
           PPSPPP    PLL  LLLL L  LL  AG  C+      + +   K T   +A T+H  S +    G
EPHB3      PPSPPPGLLPLLPLLLLPAG-CRALEETLMDTKWVTSELAWTSHPESGEEEVSG mDRAGON    FDSEFCKALRAYAGCTQRTS 102
           +D  E     +R Y C  R  S
EPHB3      YD-EAMNPIRTYQVCNVRES 86
```

FIG. 5

```
mDRAGON  PAAAGAEQSRRPGLWPPSPPPL----LLLLLSLGLLHAGDCQQPTQCRIQ-KCTTDSV
         P A G + RRP + PP PPPP+   LLLLL  G  A C   + C    +CT
hNotch3  PGARGRRRRRRP-MSPPPPPPVRALPLLLLLAGPGAA-APPCLDGSPCANGGRCTQLPS mDRAGON  ALTAHLNSAADGFDSEFCKALRAYAGCTQRTSKACRGNLVYHSAVLGISDLMSQRNCSKD
         A L    G+ E C+     C    S C G V  S+V+  +  S R C +
hNotch3  REAACL--CPPGWGERCQLEDP----CH---SGPCAGRGVCQSSVVAGTARFSCR-CPRG mDRAGON  --GPTSSTNPEVTHDPCNYHSHGGVREHGGGDQR-----PPNY 157
           GP  S    PC    +HG  R  G D R      PP Y
hNotch3  FRGPDCSLPDPCLSSPC---AHGA-RCSVGPDGRFLCSCPPGY 150 mDRAGON  KSLHIVEKESGRYVEMHARYIGTTVFVRQLGRYLTLAIRMPEDLAMSYEESQDLQLCVNG
         + LH+ E+   ++E  R +      ++ +   L + I   D+ + +E   +++
mPIP5K   QKLHVGEESKKNFLEKLKRDVEFLAQLKIMDYSLLVGIH---DVDRAEQEEMEVE----ER mDRAGON  CPMSECIDDGQGQVSAILGHSLPHTT--SVQAWPGY--------TLETASTQCHEKMPVK
         EC +DG G  S +  P  +  ++ ++P +              +++  + + HE  P K
mPIP5K   AEEEECENDGVGG-SLLCSYGTPPDSPGNLLSFPRFFGPGEEFDPSVDVYAMKSHESAPKK mDRAGON  DIYFQSCVFDLLTTGDANFTAA-------AHSALEDVEALHPRK--ERWHIFPSS 395
         ++YF + + D+LT  DA   AA       H A  ++  ++P +   +R++ F S+
mPIP5K   EVYFMA-IIDILTPYDAKKKAAHAAKTVKHGAGAEISTVNPEQYSKRFNEFMSN 389
```

FIG. 6

```
mDRAGON    QKCTTDSVALTAHLNSAADGFDSEFCKALRAYAGCTQRTSKACRGNLVYHSAVLGISD--
           + C T       AA G  +E C  + A GC       + +G       Y     G  D
THR1       ENCLTTKYGCCPDGKGAAKGHHNEGCGCVYAQYGCCPDGKTSAKGAGFY----GCPDSC mDRAGON    LMSQRNCSKDGPTSSTNPEVTHDPCNYHSHG---------GVREHGGGDQRPPNYLFC
           SQ  C  DG T +             PC Y  +G          GR G D R   Y C
           AQSQFGCCPDGKTPARGSHKEGCPCQYTRYGCCPDGETTALGPRNDGCDDCRYAKYGCC mDRAGON   60 QKCTTDFVALTAHLNSAADGFDSEFCKALRAYAGCTQRTSKACRGNLVYHSAVLGISDLM 119
          + C      A    S+  GF  E  C+          C QRT+  C GN   H   L  I+ +
mSlit2   830 EPCHKKVCAHGMCQPSSQSGFTCE-CEEGWMGPLCDQRTNDPCLGNKCVHGTCLPINAFS 888 mDRAGON  120 SQRNCSK-DGPTSSTNPEVTHDPCNYHS--HGGVREHGGGDQRPPNYLFCGLFGD 171
             C + G      E   +PC        HG R  G G  +P       G+ GD
mSlit2   889 YSCKCLEGHGGVLCDEEEDLFNPCQMIKCKHGKCRLSGVG--QPYCECNSGFTGD 941
```

DRAGON | DRG11

Luciferase activity assay

Control | Prom+DRG11 | Prom/-DRG11

Interaction between DRAGON promoter and DRG11-DBD

DRAGON mRNA

WT | DRG11-/-

Adult: Cortex, Cerebellum, Skin, Liver, Heart, Kidney | E14.5: Whole emb, Brain

```
DRAGON : MGVRAAPSCAAAPAAAGAEQSRRPGLWPSPPPLLLLLLLSTGLFHAGDCQQPTQCRIQ :  60
DL-2   : -------MQPPRERLVVTGRAGWMGRGAGRSALGLWPTTAFLLCSFPAAISPCKIL :  51
DL-1   : --------------------------MGQSPSPRSPHGSPPTLSTHTTLELLLCGQAHSQCKIL :  37

DRAGON : --------NSAADGEDS-EFCKALRAYAGCTQRTSKACRNLVYH : 109
DL-2   : KCTTDEVALTAHL------SHAPASDDVPEFCAALRTYALCTRRTARTCRGDLAYH : 101
DL-1   : KCNSEFWSATSSG------SHAPASDDVPEFCAALRTYALCTRRTARTCRGDLAYH : 101
         RCNAEYVSSTLHLRGGSPDTPRGGGRGGLASGGLCRALRSYALCTRRTARTCRGDLAFH :  97

DRAGON : SAVLGISDLMSQRNCSKDGPTSSTNPEVTHDPCNYHSGG------VREHGGGDQRPPNY : 163
DL-2   : SAVHGIEDIMSQBNCSKDGPTSQPRVRTLPPAGDSQERSDSPEICHYEKSFHKHSAAPNY : 161
DL-1   : SAVHGIEDIMIQHNCSROGETAPPPARGPALPGAGPAPLTPDPCDYEARFSRLHGRAPGE : 157

DRAGON : LFCGLFGDPHLRTEKDHFQTCKVEGAWPLIDNNYLSVQVTNVPVPGSSATATNKVTIIE : 223
DL-2   : THCGLFGDPHLRTETDHFQTCKYQGAWPLIDNNYLNVQVTNTPVLPGSAATATSKLTIIE : 221
DL-1   : LHCASHGDPHVRSEHNQFHTCRVQGAWPLIDNDFIFVQATSSEVSSGANATTIRKVTIIE : 217

DRAGON : KAQHECTDQKVYQAVTBDDIEPAAFVDGTTSGGD-VKSLHIVEKESGRYVEMHARYIGTT : 282
DL-2   : KNFQECVDQKVYQAEMDELPSAFADGSKNGGDKHGANSLKITEKVSGQHVEIQAKYIGTT : 281
DL-1   : KNMQECIDQKVYQAEVDNLPAAFEDGSINGGDRPGGSSLSIQTANLGSHVEIRAAYIGTT : 277

DRAGON : VEVRQLGRYLTLAIRMPEDIAMSYEE--SQDLQLCVNGCPMSECIDDGQGQVSAILGHSL : 340
DL-2   : IVVRQVGRYLTFAVRMPPEVVNAVEDRDSQGHYLECLRGCPLNQQIDFQAFRANAESPRRP : 341
DL-1   : IILRQTAGQLSFSIRVAEDVARAFSA--EQDLQLCVGGCPSQRLSRSERNR--------- : 327

DRAGON : PHTTSVQAWPG-YTLETASTQCHEKMPVKDIYFQSCVFDLLTTCGDANFTAFAHSALEDVE : 399
DL-2   : AAASPSPVVPETFPYETAVAKCKEKLPVEDLYYQACVFDLLTTCGDVNFTLAAYYAIEDGK : 401
DL-1   : ------RGAIAIDTRRRLCKEGLPVEDAYEQSCVFDVSVSGDPNFTVAAQTALDDAR : 378

DRAGON : ALHPRKERWHILPP-------------------------------- : 436
DL-2   : MLHSNKDKLRLRERTRELPGAVAAAAAATTFPTAPQILGTIPLLVLEPVLW--- : 454
DL-1   : IFLTDLENLHLPP---SDAGPPLSPAICLVPLLSALFVWLLCFSK : 420
```

FIG. 8B

```
Human     : MGLRAAP--SSAAAAAEVEQRRRPGLCPP--PLELTLFLFSLGEHAC-DCQQPAQCRI :  56
Mouse     : MGVRAAPSCAAAPAAAGAEQSRRPGLWPPSPPPPLHLLLSLGFLHAC-DCQQPTQCRI :  59
Zebrafish : ------------MGMGRAGSYYPGAERLISPVLHLLVLCTLSSLTPIGESQVTPQCRI :  47

Human     : QKCTTDFVSLTSHLNSAVDGFDSEFCKALRAYAGCTQRTSKACRGNLVYHSAVLGISDIM : 116
Mouse     : QKCTTDFVALTAHLNSAADGFDSEFCKALRAYAGCTQRTSKACRGNLVYHSAVLGISDIM : 119
Zebrafish : QKCTTDFVSLTSHLNPSLDGFDTEFCKALRAYSACTQRTAKSCRGNLVFHSAMIGITDIM : 107

Human     : SQRNCSKDGPTSSTNPEVTHDPCNYHSHAGAREHRRGDQNPPS----YLFCGLFGDPHLR : 172
Mouse     : SQRNCSKDGPTSSTNPEVTHDPCNYHSHGGVREHGGDQRPPN----YLFCGLFGDPHLR : 175
Zebrafish : SQRNCSKDGPTSSTHPVIPIEPCNYHSRHHHHVSRFGTGVPEHPRLMYLFCGLFGDPHLR : 167

Human     : TFKDNFQTCKVEGAWPLIDNYLSVQVTNVPVVPGSSATATNKVTIIFKAHHECTDQKVY : 232
Mouse     : TFKDHFQTCKVEGAWPLIDNYLSVQVTNVPVVPGSSATATNKVTIIFKAQHECTDQKVY : 235
Zebrafish : QFQTCKVEGAWPLIDNNYLSVQVTNVPVVYGSSATATNKITIIFKPYQECTDQKVY : 227

Human     : QAVTDDLPAAFVDGTTSGGDSDAKSLRIVEREESGHYVEMHARYIGTTVFVRQVGRYLTLA : 292
Mouse     : QAVTDDLPAAFVDGTTSGGDGDVKSLHIVEKEESGRYVEMHARYIGTTVFVRQLGRYLTLA : 295
Zebrafish : QAVTDDLPAAFVDGTISGGDSETRSIWILEKSPCRHVEIHEAVIGVTIIIRQQGRYLTLA : 287

Human     : IRMPEDIAMSYESQDLQLCVNGCPLSERIDDGQGQVSALLGHSLP------RTSLVQAW : 346
Mouse     : IRMPEDIAMSYESQDLQLCVNGCPMSECIDDGQGQVSALLGHSLP------HTTSVQAW : 349
Zebrafish : VRMPELAMAFDEIQDLQLCMNGCPTLSERIDQEGHLQLPVLGLQQAGFQQQQQPRVEAQR : 347

Human     : PGYTLETANTQCHEKMPVKDIYFQSCVFDLLTTGDANFTAAAHSALEDVEALHPRKERWH : 406
Mouse     : PGYTLETASTQCHEKMPVKDIYFQSCVFDLLTTGDANFTAAAHSALEDVEALHPRKERWH : 409
Zebrafish : GVFTLESASRRCRDQLEVKDIYFHSCVFDLLTTGDANETTAAYNALKDMETLHPKKERWQ : 407

Human     : IFPSSGNGTPRGGSDISVSLGLTCIHIVFI : 437
Mouse     : IFPSSCG----GCRDTPVGLGLTCIHIMFL : 436
Zebrafish : IFPNSASRLSPFSLLITALISSFLIAVLI-- : 436
```

FIG. 10
Dragon (mRNA) Adult Rat DRG
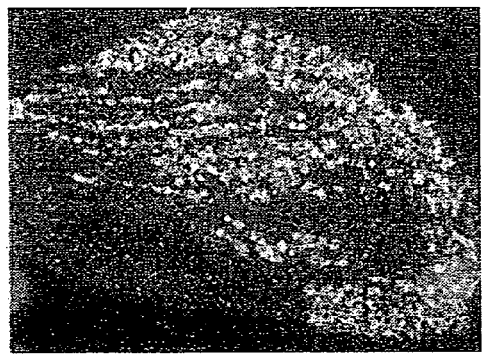
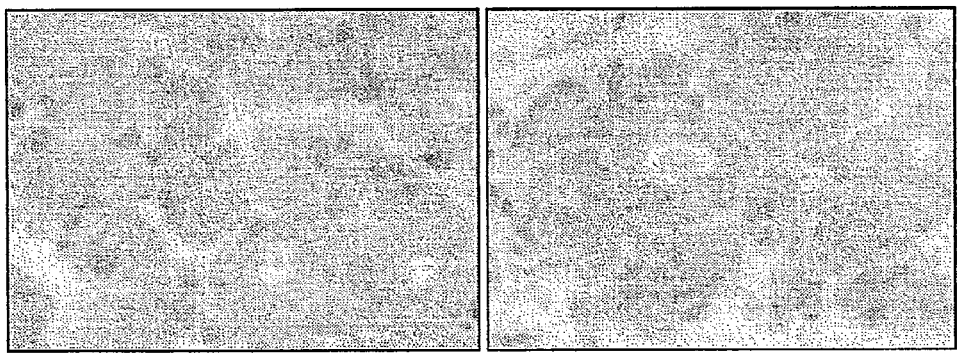
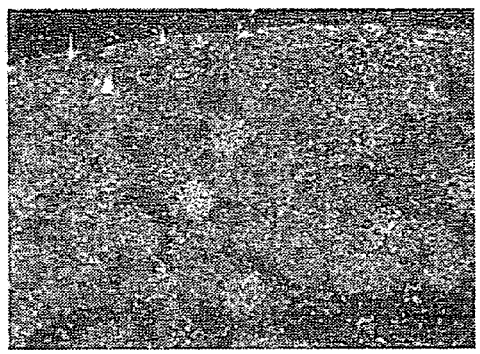

Cell adhesion assay

Cell adhesion assay

Cell adhesion assay

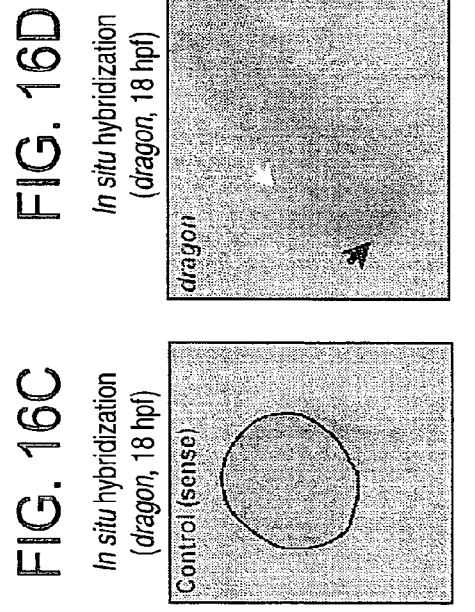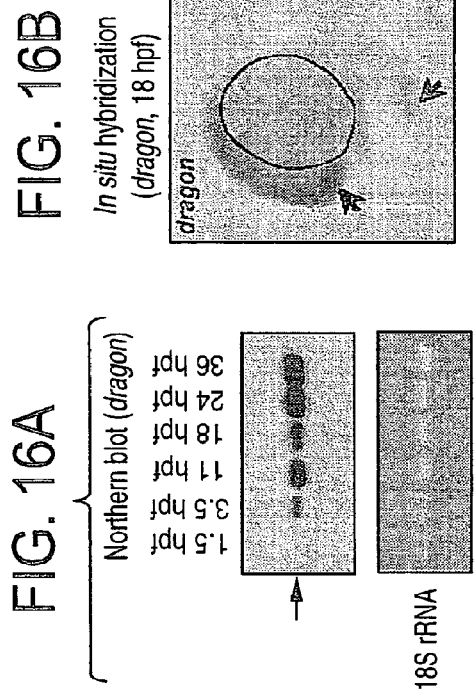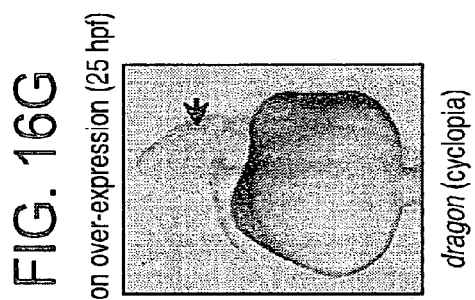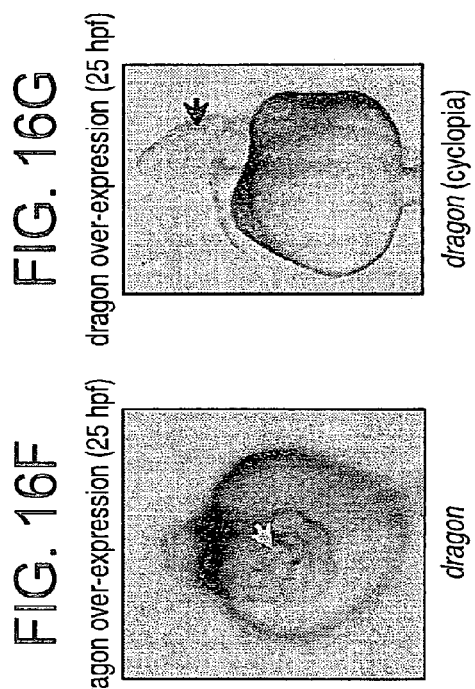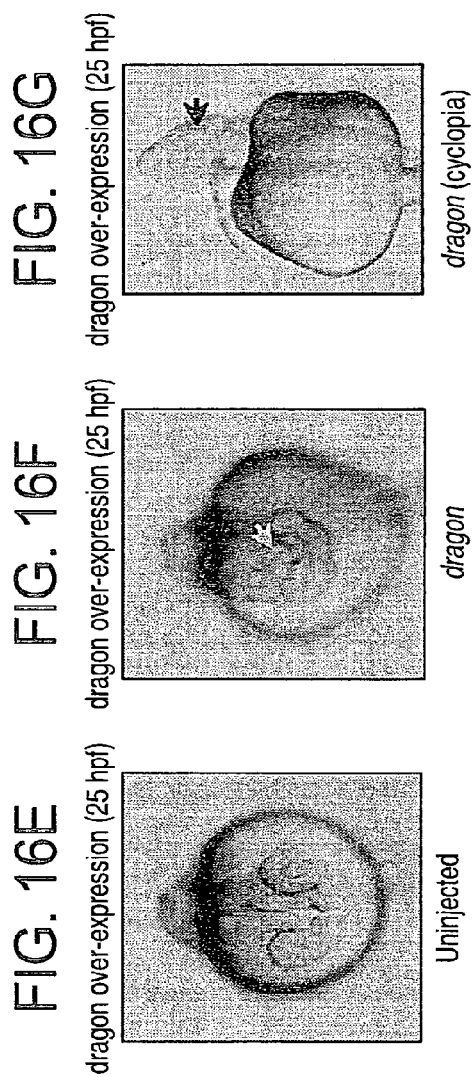

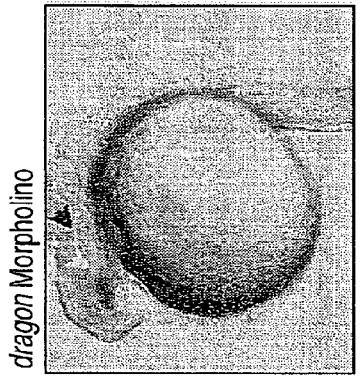
FIG. 16I Control Morpholino  FIG. 16J dragon Morpholino
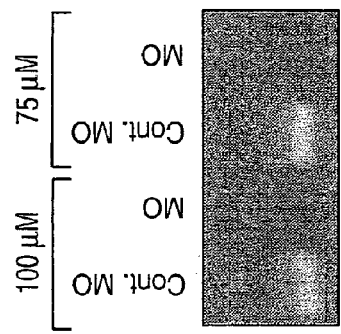
FIG. 16H
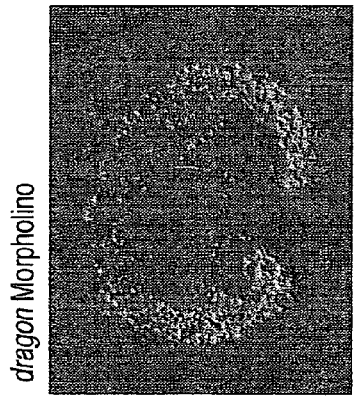
FIG. 16K Uninjected
FIG. 16L Control Morpholino
FIG. 16M dragon Morpholino

FIG. 17

```
mDRAGON   FCGLFGDPHLRTFKDHFQTCKVEGAWPLIDNNYLSVQVTNVPVVPGSSATATNKVTIIFK
          +C LFGDPHL F   QTC  EGA PL+DN Y  VQVTN V  +   T  KVT++ +
C. elegans YCSLFGDPHLIMFNGSVQTCSEEGARPLVDNRYFLVQVTNRNVRGEALTTTVTKVTVLVR AQHECTDQKVYQAVTDD--LPAAFVDGTTSGGDVKSLHIVEK--ESGRYVEMHARYIG
          +H CT   Y+A +D+  LP  FVDGTT        + S H VE    +   YVE+    +I
C. elegans -KHNCTASLRYEASSDEEGLPRGFVDGTTF----QMTSKHSVEVLWQDDNYVEIALHFIH TTVFVRQLGRYLTLAIRMPEDLAMSYEESQDL--QLCVNGCPMSECI
          +++ +R+ G YL+++R P    + E  D+ +LC +GC  S  I
          SSIHIRRQGPYLSVSVRAP---TIVLETGGDVARELCWSGCRKSSRI
```

C. elegans DRAGON

MRRHWKEFECEKWESCNDNSHVKRKHVNTGHICGGKFELSEKNLAAKFKYSGDTVWRGRPNFLKSLCYFN
PPPSNRKLKYCSLFGDPHLIMFNGSVQTCSEEGARPLVDNRYFLVQVTNRNVRGEALTTTVTKVTVLVRK
HNCTASLRYEASSDEEGLPRGFVDGTTFQMTSKHSVEVLWQDDNYVEIALHFIHSSIHIRRQGPYLSVSV
RAPTIVLETGGDVARELCWSGCRKSSRIPAELAVEMTKKFAECYRRRVHVPKKVAEETTFLSEQKVLPIY
DRCKDIGNIGVFFDASARKILNFRVSGSQVTSLQNCKARRGLRRGQAILERYFSAPKPKKFHLCTATGG
QVTALQSFEARRGLRRGQATTVERCISAPRDPTDLKIFALTDNCEETKKYWNFFRYDILCDTHSQNFLLP

SEQUENCE LISTING

<160> NUMBER OF SEQ ID NOS: 36

<210> SEQ ID NO 1
<211> LENGTH: 1332
<212> TYPE: DNA
<213> ORGANISM: Mus musculus

<400> SEQUENCE: 1

| | | | | | |
|---|---|---|---|---|---|
| acgagacctg | catggacggg | catgggcgtg | agagcagcac | cttcctgcgc | cgccgccccc | 60 |
| gccgccgccg | gggctgagca | gtcccgccgc | cccgggctct | ggccgccgtc | gccccgccg | 120 |
| ccgctgttgc | tgctgctgct | gctcagcctt | gggctgctcc | acgcaggtga | ttgccaacag | 180 |
| cctactcaat | gccgaatcca | gaaatgtacc | acagacttcg | tggccctgac | tgcacacctg | 240 |
| aactctgccg | ctgatgggtt | tgactctgag | ttttgcaagg | cacttcgcgc | ctatgctggc | 300 |
| tgcacccagc | gaacttcaaa | ggcctgccga | ggcaacctgg | tgtaccattc | tgctgtgtta | 360 |
| ggcatcagtg | atctcatgag | ccagaggaac | tgttccaagg | atggacccac | atcttccacc | 420 |
| aatccggaag | tgacccatga | cccctgtaac | taccacagcc | acgggggagt | cagagaacat | 480 |
| gggggagggg | accagagacc | tcccaattac | ctttttctgtg | gcttgtttgg | agaccctcac | 540 |
| cttcgaactt | tcaaggatca | cttccagaca | tgcaaagtgg | aaggggcctg | gccactcata | 600 |
| gacaacaatt | acctttcggt | tcaagtgacg | aacgtgcctg | tggtccccgg | gtccagtgca | 660 |
| actgctacaa | acaaggtcac | gattatcttc | aaagcacagc | acgagtgcac | ggatcagaag | 720 |
| gtgtaccaag | ctgtgacaga | tgacctgccg | gccgcctttg | tagatggcac | caccagtggg | 780 |
| ggggacggtg | acgtgaagag | tcttcacatc | gtggagaagg | agagtggccg | ctacgtagag | 840 |
| atgcatgccc | gctacatagg | caccacagtg | tttgtgcgac | agctgggtcg | ctacctaacc | 900 |
| ctcgctatcc | ggatgcccga | agacttggcc | atgtcctatg | aggaaagcca | ggacttgcag | 960 |
| ctgtgtgtga | atggctgccc | catgagtgaa | tgcattgatg | atggacaagg | ccaggtgtct | 1020 |
| gctatcctgg | ggcacagcct | gcctcacacc | acctcagtgc | aggcctggcc | tggctacaca | 1080 |
| ctggagactg | ccagcaccca | atgccacgag | aagatgccgg | tgaaggacat | ctatttccaa | 1140 |
| tcgtgtgtct | tcgacctgct | caccactggt | gatgccaact | ttactgctgc | agcccacagt | 1200 |
| gccttggagg | atgtggaagc | gctgcaccca | agaaaggaac | gctggcacat | cttccccagc | 1260 |
| agctgtgggg | gatgtaggga | tttgcctgtt | ggtcttggac | tcacatgctt | gatccttatt | 1320 |
| atgttttttgt | ag | | | | | 1332 |

<210> SEQ ID NO 2
<211> LENGTH: 1897
<212> TYPE: DNA
<213> ORGANISM: Mus musculus

<400> SEQUENCE: 2

| | | | | | |
|---|---|---|---|---|---|
| gccaaatttc | ttcttccagt | cacagaagta | cccagagaaa | ttcactaggt | aggaggctca | 60 |
| tcatctggga | agaaccggtg | cctgggggga | cctggctgga | taggtatggg | ccagtcccct | 120 |
| agtccccggt | ccccccacgg | cagccctcca | actctaagca | ccctcactct | cctgctgctc | 180 |
| ctctgtggac | aggctcactc | ccagtgcaag | atcctccgct | gcaatgccga | gtatgtctcg | 240 |
| tccactctgc | atcttcgggg | aggtggctca | ccggacacgc | cgcgtggagg | cggccgtggt | 300 |
| gggctggcct | caggtggctt | gtgtcgcgcc | ctgcgctcct | acgctctctg | cacgcggcgc | 360 |
| acggcccgca | cctgccgcgg | ggaccttgct | ttccactctg | cggtgcatgg | catagaggac | 420 |
| ctgatgatcc | agcacaactg | ctcacgccag | ggtcccacgg | ccccgccccc | ggcccggggc | 480 |

```
cccgccctgc ccggggccgg gccagcgccc ctgaccccag atccctgtga ctatgaggcc    540
cggttttcca ggctgcacgg tcgagccccg ggcttcttgc attgcgcatc ctttggagat    600
ccccatgtgc gcagtttcca caaccaattt cacacatgcc gtgtccaagg agcttggccc    660
ttgctagata acgacttcct ctttgtccag gccaccagct ccccggtttc gtcgggagcc    720
aacgctacca ccatccggaa ggtcactatc atatttaaaa acatgcagga atgcattgac    780
cagaaagtct accaggctga ggtggacaat cttcctgcag cctttgaaga tggttctatc    840
aatggggggcg accgacctgg gggctcgagt tgtccattc aaactgctaa ccttgggagt     900
cacgtggaga ttcgagctgc ctacattgga caactatca tcattcgaca gacagctggg      960
cagctctcct tctccatcag ggtagcagag gatgtggcgc gggccttctc cgcagagcag    1020
gacctacagc tgtgtgttgg gggatgccct ccgagccagc gactctctcg ctcagagcgc    1080
aaccgccgtg gggctatagc catagatact gccagaaggc tgtgtaagga agggcttccg    1140
gttgaagatg cctacttcca atcctgcgtc tttgatgttt cagtctccgg tgaccccaac    1200
tttactgtgg cagctcagac agctctggac gatgcccgaa tcttcttgac ggatttagag    1260
aacttacatc tctttccctc agatgcgggg cctcccctct ctcctgccat ctgcctagtc    1320
ccgcttcttt cggccctctt tgttctgtgg ctttgcttca gtaagtaggc cagcaaccca    1380
tgactggttt ggaaacgatt tgaggataga ggttggtgtg agaaaccaca agatgtgcc     1440
aaaggaaaca gcggggacag gagacaacac ttactcaatc agatgaggtt gcagtccagg    1500
gctgaaatga ccctagaata aagattctgg gccagggttt tgcactccag accttggtgt    1560
gggctattca ccatggattt cccagttagt gatttcccac ttgtaatgaa attccactct    1620
ccatacacct gataccactc ctacaagcct agagattgtg agagtgctaa tgaccagtga    1680
aacattaaag gactgagata tcgtaaaggc aaaaacatga ttctctttga gaaagtcaaa    1740
agaggagaag ctaattagga aaagcttttg gttcagaaac gaagtgggca ttgtctggca    1800
gaggaagtca gcttttggag actggcacca actcagaaac gggcatttcc atcccttcct    1860
aatctgttat taaagcgatt agttctccat cctgtcc                              1897
```

<210> SEQ ID NO 3
<211> LENGTH: 1559
<212> TYPE: DNA
<213> ORGANISM: Mus musculus

<400> SEQUENCE: 3

```
cctcccacct cacccagggg cccacgagcg accgccctac acctagtctt cgcgcgcagc     60
cccgccagcg ccaaccccc gcgggctgga ggggctcatg cagccgccaa gggagaggct    120
agtggtaaca ggccgagctg gatggatggg tatggggaga ggggcaggac gttcagccct    180
gggattgtgg ccgaccctcg ccttccttct ctgcagcttc cccgcagcca tctcccctg     240
caaaatcctc aagtgcaact ctgagttctg gagcgcacg tcatcaggca gccacgcccc      300
tgcctccgac gacgtgccgg agttctgtgc agccctgcgc acctacgccc tgtgcactcg    360
gcggacagcc cgcacctgcc ggggcgacct ggcttaccac tcggctgtcc atggcataga    420
ggaccttatg agccagcaca actgctccaa ggacggcccc acctcacagc cgcgagtgcg    480
cacgctcccg ccagctgggg acagccagga gcgctcggat agccccgaga tctgccacta    540
tgagaagagt ttccacaagc actcagctgc ccccaactac actcactgcg gcctcttgg     600
ggacccacac ctcaggactt tcacagacca cttccagaca tgcaaggtgc aaggcgcctg    660
```

-continued

| | |
|---|---|
| gcctctcatc gacaataatt acctgaacgt gcaagtcacc aatacacctg tgctgccggg | 720 |
| ctccgcagct accgccacca gcaagctcac catcatcttc aagaacttcc aagagtgtgt | 780 |
| ggaccagaaa gtctaccaag ctgaaatgga cgaacttccg tctgcctttg cggacggctc | 840 |
| caaaaatggg ggagataaac acggggccaa cagcctgaag atcacagaga aggtgtcggg | 900 |
| ccagcacgtg gagatccagg ccaagtacat cggcaccacc atcgtggtgc gacaggtggg | 960 |
| ccgctacctg acctttgccg tccggatgcc cgaggaggta gtcaacgccg tggaggaccg | 1020 |
| tgacagccaa ggcctctacc tctgcctgcg gggctgcccg ctcaaccagc agatcgactt | 1080 |
| ccaggctttc cgtgccaacg ctgaaagccc tcgcaggcca gcagccgcca gtccctctcc | 1140 |
| cgtggtcccc gagacattcc cctatgagac agccgtggcc aagtgcaaag agaagctgcc | 1200 |
| cgtagaagac ctgtactacc aggcctgtgt cttcgacctc ctcacgactg gtgatgtgaa | 1260 |
| cttcacgctg gctgcctact atgctttgga ggatggcaag atgctccact ccaacaagga | 1320 |
| caagctgcat ctgtttgaaa ggactcggga gctgccagga gccgtggccg ccgccgccgc | 1380 |
| cgctgccacc acattcccct ggccccccca gattctcctt ggcaccatcc cacttctggt | 1440 |
| cctcctgcct gtgttgtggt agacagttgg ccatgtaggt aggatacaga ggagagtaac | 1500 |
| gactgccctg agccttgggc tcctgcccct ggcttctcct tttgtctgtg ggctcaagt | 1559 |

<210> SEQ ID NO 4
<211> LENGTH: 3946
<212> TYPE: DNA
<213> ORGANISM: Homo sapiens

<400> SEQUENCE: 4

| | |
|---|---|
| acgacacctg catggacggg catgggcttg agagcagcac cttccagcgc cgccgctgcc | 60 |
| gccgccgagt tgagcagcg ccgccgcccc gggctctgcc cccgccgct ggagctgctg | 120 |
| ctgctgctgc tgttcagcct cgggctgctc cacgcaggtg actgccaaca gccagcccaa | 180 |
| tgtcgaatcc agaaatgcac cacggacttc gtgtccctga cttctcacct gaactctgcc | 240 |
| gttgacggct ttgactctga gttttgcaag gccttgcgtg cctatgctgg ctgcacccag | 300 |
| cgaacttcaa aagcctgccg tgcaacctg gtataccatt ctgccgtgtt gggtatcagt | 360 |
| gacctcatga gccagaggaa ttgttccaag gatggaccca tcctctac caaccccgaa | 420 |
| gtgacccatg atccttgcaa ctatcacagc cacgctggag ccaggaaca caggagaggg | 480 |
| gaccagaacc ctcccagtta cctttttttgt ggcttgtttg gagatcctca cctcagaact | 540 |
| ttcaaggata acttccaaac atgcaaagta aaggggcct ggccactcat agataataat | 600 |
| tatctttcag ttcaagtgac aaacgtacct gtggtccctg gatccagtgc tactgctaca | 660 |
| aataaggtca ctattatctt caaagcccac catgagtgta cagatcagaa agtctaccaa | 720 |
| gctgtgacag atgacctgcc ggccgccttt gtggatggca ccaccagtgg tgggacagc | 780 |
| gatgccaaga gcctgcgtat cgtggaaagg gagagtggcc actatgtgga gatgcacgcc | 840 |
| cgctatatag ggaccacagt gtttgtgcgg caggtgggtc gctacctgac ccttgccatc | 900 |
| cgtatgcctg aagacctggc catgtcctac gaggagagcc aggacctgca gctgtgcgtg | 960 |
| aacggctgcc ccctgagtga acgcatcgat gacgggcagg gccaggtgtc tgccatcctg | 1020 |
| ggacacagcc tgcctcgcac ctccttggtg caggcctggc ctggctacac actggagact | 1080 |
| gccaacactc aatgccatga gaagatgcca gtgaaggaca tctatttcca gtcctgtgtc | 1140 |
| ttcgacctgc tcaccactgg tgatgccaac tttactgccg cagcccacag tgccttggag | 1200 |
| gatgtggagg ccctgcaccc aaggaaggaa cgctggcaca ttttcccag cagtggcaat | 1260 |

```
gggactcccc gtggaggcag tgatttgtct gtcagtctag gactcacctg cttgatcctt   1320
atcgtgtttt tgtaggggtt gtcttttgtt ttggtttttt attttttgtc tataacaaaa   1380
ttttaaaata tatattgtca taatatattg agtaaaagag tatatatgta tataccatgt   1440
atatgacagg atgtttgtcc tgggacaccc accagattgt acatactgtg tttggctgtt   1500
ttcacatatg ttggatgtag tgttctttga ttgtatcaat tttgttttgc agttctgtga   1560
aatgttttat aatgtccctg cccagggacc tgttagaaag cactttatttt tttatatatt  1620 aaatatttat gtgtgtgctt ggttgatatg tatagtacat atacacagac atccatatgc   1680
agcgtttcct ttgaaggtga ccagttgttt gtagctattc ttggctgtac cttcctgccc   1740
tttcccattg ctactgattt gccacggtgt gcagctttta ctcgccacct tccggtggag   1800
ctgcctcgtt cctttgaact atgccctcac ccttctgccc tcacttgatt tgaaagggtc   1860
gttaactctc ccttacaggt gctttgactc ttaaacgctg atcttaagaa gctctcttca   1920
tctaagagct gttactttt cagaagggg ggtattattg gtattctgat tactctcaat    1980
tctaattgtt atatatttga gcccatacag tgtattaggt tgaaccatag aaactgctat   2040
tctcgtaggt caaaagggtc tagtgatgga agttttgtag ataagtacca ggcatctcag   2100
taactcctag acttttttctc atcccatgcc ccgttttaaa ttgtcagttt tccctctgac  2160
tcttctgtgt taaaacatga aactataaat ttagtaatta tcatgccttg ctcttttaa    2220 tctatatgac tgatgcaagc ccctcttctt aaccgtttct tggctttgag cccagaaaca   2280
cagctctccc tgtctccaac tccagtaagc cctcctcagc ctcaccttac gaatccaaag   2340
aactggggtt tgttaggttc tttctctaat gtagaggccc agatcccatc acaaagtttt   2400
tcattcttcc ttgtccacca tgatcttcat cacagtcttt gatatgtctg catgcaaagt   2460
ggaacagagt tgggcggcaa tgacagaaga gcttccttgg cctgactcgg tgtgcggcca   2520
cttcggcact gcttaatcca gatattcttg ttaactaagc attgtgcttc ccaggtggtc   2580
tgaagtcagg tactctctct ctcaacacct gtagttgaat atgatttggt cagttgctcg   2640
ttgtaacttg gagaaattcc tataaagtaa gatctccttg cctcttccat ccattgttgg   2700
cacccccttg caaaaggaaa agaacagcaa aagtcaggag cagtaatctg agaaagttaa   2760
ctccaggata ggtaggtttc tattgttata gctagatgta aatctttagt tccaagaagt   2820
gatagagttt ctgctttaat aatttgttga taagttaca taaacagaaa taaaagatac    2880
tatctttacc gtagtagttc aggccaagat tatgcttagt tttagttctc caggtagtta   2940
cttttgccat gtcctattga tcagtgacac tgccagaggc ccataccggc aagaggaaga   3000
ggacgtcatt ttgtaaagtt taacttctta gcgaactgat gtgccaccca gtcacagagt   3060
ggagttgtga attcatgtag aggtggcaaa cctctacctt tgttgatga gagaataatc     3120 ttgggcagtc tgggaaaata aggaaggcat ctccttctta ctcatggaga ttcaactata   3180
gagagttgaa acctaaaccc gccttccttt tatagaagct ggactagaga cggactgacc   3240
atcagctctg aactgtggct ttttttgttc acctatgatg ccatgtacca aattcagaag   3300
ctatcgttaa taatttgttt tataattgag tagtacaagc gaggaaaaaa tacggaggat   3360
aaccactatt tttgtgcaaa tagtatgaaa gtgaagtaaa agcaatagaa gaaatttcta   3420
taggatctgg gtttagagtg tgtatcatta ataaatatac ctttgctctt tcagggaaa    3480 ataacaacca cccttactga tagttgggaa aagaagattg ggttattttg ccatatcatt   3540
tagctggaag tgacatttaa aagcaccctg catcactagt aatagtgtat tttgctattc   3600
```

-continued

```
tgcccttgta atcggtgtcc ctgtaaaaca atccccacag attactttca gaaatagatg    3660
tatttctcta cgtaagggcc aggtttattt tctccttttt tgagatttct agaaaaaatg    3720
ctgcttgcac atgttggttc ttgaaacctt agctagaaga atttcaggtc ataccaacat    3780
gtggataggc tatagctgtt cagaggtctc ctgggggagc ttaaaacggg ggaaacactg    3840
gttttcacag atgctccaca tggctgtctt taaaagactc aaaactttt tttgtcctct    3900 ttgttatgct tggaagctcc cccccccca acagtgtgtc gagtct                   3946

<210> SEQ ID NO 5
<211> LENGTH: 436
<212> TYPE: PRT
<213> ORGANISM: Mus musculus

<400> SEQUENCE: 5

Met Gly Val Arg Ala Ala Pro Ser Cys Ala Ala Pro Ala Ala Ala
 1               5                  10                  15

Gly Ala Glu Gln Ser Arg Arg Pro Gly Leu Trp Pro Ser Pro Pro
                20                  25                  30

Pro Pro Leu Leu Leu Leu Leu Leu Ser Leu Gly Leu Leu His Ala
                35                  40                  45

Gly Asp Cys Gln Gln Pro Thr Gln Cys Arg Ile Gln Lys Cys Thr Thr
50                  55                  60

Asp Phe Val Ala Leu Thr Ala His Leu Asn Ser Ala Ala Asp Gly Phe
65                  70                  75                  80

Asp Ser Glu Phe Cys Lys Ala Leu Arg Ala Tyr Ala Gly Cys Thr Gln
                85                  90                  95

Arg Thr Ser Lys Ala Cys Arg Gly Asn Leu Val Tyr His Ser Ala Val
                100                 105                 110

Leu Gly Ile Ser Asp Leu Met Ser Gln Arg Asn Cys Ser Lys Asp Gly
                115                 120                 125

Pro Thr Ser Ser Thr Asn Pro Glu Val Thr His Asp Pro Cys Asn Tyr
130                 135                 140

His Ser His Gly Gly Val Arg Glu His Gly Gly Asp Gln Arg Pro
145                 150                 155                 160

Pro Asn Tyr Leu Phe Cys Gly Leu Phe Gly Asp Pro His Leu Arg Thr
                165                 170                 175

Phe Lys Asp His Phe Gln Thr Cys Lys Val Glu Gly Ala Trp Pro Leu
                180                 185                 190

Ile Asp Asn Asn Tyr Leu Ser Val Gln Val Thr Asn Val Pro Val Val
                195                 200                 205

Pro Gly Ser Ser Ala Thr Ala Thr Asn Lys Val Thr Ile Ile Phe Lys
210                 215                 220

Ala Gln His Glu Cys Thr Asp Gln Lys Val Tyr Gln Ala Val Thr Asp
225                 230                 235                 240

Asp Leu Pro Ala Ala Phe Val Asp Gly Thr Thr Ser Gly Gly Asp Gly
                245                 250                 255

Asp Val Lys Ser Leu His Ile Val Glu Lys Glu Ser Gly Arg Tyr Val
                260                 265                 270

Glu Met His Ala Arg Tyr Ile Gly Thr Thr Val Phe Val Arg Gln Leu
                275                 280                 285

Gly Arg Tyr Leu Thr Leu Ala Ile Arg Met Pro Glu Asp Leu Ala Met
            290                 295                 300

Ser Tyr Glu Glu Ser Gln Asp Leu Gln Leu Cys Val Asn Gly Cys Pro
305                 310                 315                 320
```

Met Ser Glu Cys Ile Asp Asp Gly Gln Gly Gln Val Ser Ala Ile Leu
                325                 330                 335

Gly His Ser Leu Pro His Thr Thr Ser Val Gln Ala Trp Pro Gly Tyr
            340                 345                 350

Thr Leu Glu Thr Ala Ser Thr Gln Cys His Glu Lys Met Pro Val Lys
        355                 360                 365

Asp Ile Tyr Phe Gln Ser Cys Val Phe Asp Leu Leu Thr Thr Gly Asp
    370                 375                 380

Ala Asn Phe Thr Ala Ala His Ser Ala Leu Glu Asp Val Glu Ala
385                 390                 395                 400

Leu His Pro Arg Lys Glu Arg Trp His Ile Phe Pro Ser Ser Cys Gly
                405                 410                 415

Gly Cys Arg Asp Leu Pro Val Gly Leu Gly Leu Thr Cys Leu Ile Leu
            420                 425                 430

Ile Met Phe Leu
        435

<210> SEQ ID NO 6
<211> LENGTH: 397
<212> TYPE: PRT
<213> ORGANISM: Mus musculus

<400> SEQUENCE: 6

Met Gly Gln Ser Pro Ser Pro Arg Ser Pro His Gly Ser Pro Pro Thr
1               5                   10                  15

Leu Ser Thr Leu Thr Leu Leu Leu Leu Cys Gly Gln Ala His Ser
            20                  25                  30

Gln Cys Lys Ile Leu Arg Cys Asn Ala Glu Tyr Val Ser Ser Thr Leu
        35                  40                  45

Arg Leu Arg Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
            100                 105                 110

Ser Arg Gln Asp Pro Cys Asp Tyr Glu Ala Arg Phe Ser Arg Leu His
        115                 120                 125

Gly Arg Ala Pro Gly Phe Leu His Cys Ala Ser Phe Gly Asp Pro His
    130                 135                 140

Val Arg Ser Phe His Asn Gln Phe His Thr Cys Arg Val Gln Gly Ala
145                 150                 155                 160

Trp Pro Leu Leu Asp Asn Asp Phe Leu Phe Val Gln Ala Thr Ser Ser
                165                 170                 175

Pro Val Ser Ser Gly Ala Asn Ala Thr Thr Ile Arg Lys Ile Thr Ile
            180                 185                 190

Ile Phe Lys Asn Met Gln Glu Cys Ile Asp Gln Lys Val Tyr Gln Ala
        195                 200                 205

Glu Val Asp Asn Leu Pro Ala Phe Glu Asp Gly Ser Ile Asn Gly
    210                 215                 220

Gly Asp Arg Pro Gly Gly Ser Ser Leu Ser Ile Gln Thr Ala Asn Leu
225                 230                 235                 240

Gly Ser His Val Glu Ile Arg Ala Ala Tyr Ile Gly Thr Thr Ile Ile

```
            245                 250                 255
Ile Arg Gln Thr Ala Gly Gln Leu Ser Phe Ser Ile Arg Val Ala Glu
                260                 265                 270

Asp Val Ala Arg Ala Phe Ser Ala Glu Gln Asp Leu Gln Leu Cys Val
            275                 280                 285

Gly Gly Cys Pro Pro Ser Gln Arg Leu Ser Arg Ser Glu Arg Asn Arg
        290                 295                 300

Arg Gly Ala Ile Ala Ile Asp Thr Ala Arg Arg Leu Cys Lys Glu Gly
305                 310                 315                 320

Leu Pro Val Glu Asp Ala Tyr Phe Gln Ser Cys Val Phe Asp Val Ser
                325                 330                 335

Val Ser Gly Asp Pro Asn Phe Thr Val Ala Ala Gln Thr Ala Leu Asp
            340                 345                 350

Asp Ala Arg Ile Phe Leu Thr Asp Leu Glu Asn Leu His Leu Phe Pro
        355                 360                 365

Ser Asp Ala Gly Pro Pro Leu Ser Pro Ala Ile Cys Leu Val Pro Leu
    370                 375                 380

Leu Ser Ala Leu Phe Val Leu Trp Leu Cys Phe Ser Lys
385                 390                 395

<210> SEQ ID NO 7
<211> LENGTH: 464
<212> TYPE: PRT
<213> ORGANISM: Mus musculus

<400> SEQUENCE: 7

Met Gln Pro Pro Arg Glu Arg Leu Val Val Thr Gly Arg Ala Gly Trp
  1               5                  10                  15

Met Gly Met Gly Arg Gly Ala Gly Arg Ser Ala Leu Gly Leu Trp Pro
                 20                  25                  30

Thr Leu Ala Phe Leu Leu Cys Ser Phe Pro Ala Ala Ile Ser Pro Cys
             35                  40                  45

Lys Ile Leu Lys Cys Asn Ser Glu Phe Trp Ser Ala Thr Ser Ser Gly
 50                  55                  60

Ser His Ala Pro Ala Ser Asp Val Pro Glu Phe Cys Ala Ala Leu
 65                  70                  75                  80

Arg Thr Tyr Ala Leu Cys Thr Arg Arg Thr Ala Arg Thr Cys Arg Gly
                 85                  90                  95

Asp Leu Ala Tyr His Ser Ala Val His Gly Ile Glu Asp Leu Met Ser
            100                 105                 110

Gln His Asn Cys Ser Lys Asp Gly Pro Thr Ser Gln Pro Arg Val Arg
        115                 120                 125

Thr Leu Pro Pro Ala Gly Asp Ser Gln Glu Arg Ser Asp Ser Pro Glu
    130                 135                 140

Ile Cys His Tyr Glu Lys Ser Phe His Lys Ser Ala Ala Pro Asn
145                 150                 155                 160

Tyr Thr His Cys Gly Leu Phe Gly Asp Pro His Leu Arg Thr Phe Thr
                165                 170                 175

Asp His Phe Gln Thr Cys Lys Val Gln Gly Ala Trp Pro Leu Ile Asp
            180                 185                 190

Asn Asn Tyr Leu Asn Val Gln Val Thr Asn Thr Pro Val Leu Pro Gly
        195                 200                 205

Ser Ala Ala Thr Ala Thr Ser Lys Thr Leu Ala Thr Val Leu Gly Pro
    210                 215                 220
```

```
Met Gln Leu Thr Ile Ile Phe Lys Asn Phe Gln Glu Cys Val Asp Gln
225                 230                 235                 240

Lys Val Tyr Gln Ala Glu Met Asp Glu Leu Pro Ser Ala Phe Ala Asp
            245                 250                 255

Gly Ser Lys Asn Gly Asp Lys His Gly Ala Asn Ser Leu Lys Ile
            260                 265                 270

Thr Glu Lys Val Ser Gly Gln His Val Glu Ile Gln Ala Lys Tyr Ile
            275                 280                 285

Gly Thr Thr Ile Val Val Arg Gln Val Gly Arg Tyr Leu Thr Phe Ala
        290                 295                 300

Val Arg Met Pro Glu Glu Val Val Asn Ala Val Glu Asp Arg Asp Ser
305                 310                 315                 320

Gln Gly Leu Tyr Leu Cys Leu Arg Gly Cys Pro Leu Asn Gln Gln Ile
                325                 330                 335

Asp Phe Gln Ala Phe Arg Ala Asn Ala Glu Ser Pro Arg Arg Pro Ala
                340                 345                 350

Ala Ala Ser Pro Ser Pro Val Val Pro Glu Thr Phe Pro Tyr Glu Thr
                355                 360                 365

Ala Val Ala Lys Cys Lys Glu Lys Leu Pro Val Glu Asp Leu Tyr Tyr
                370                 375                 380

Gln Ala Cys Val Phe Asp Leu Leu Thr Thr Gly Asp Val Asn Phe Thr
385                 390                 395                 400

Leu Ala Ala Tyr Tyr Ala Leu Glu Asp Gly Lys Met Leu His Ser Asn
                405                 410                 415

Lys Asp Lys Leu His Leu Phe Glu Arg Thr Arg Glu Leu Pro Gly Ala
                420                 425                 430

Val Ala Ala Ala Ala Ala Ala Thr Thr Phe Pro Leu Ala Pro Gln
                435                 440                 445

Ile Leu Leu Gly Thr Ile Pro Leu Val Leu Leu Pro Val Leu Trp
450                 455                 460

<210> SEQ ID NO 8
<211> LENGTH: 437
<212> TYPE: PRT
<213> ORGANISM: Homo sapiens

<400> SEQUENCE: 8

Met Gly Leu Arg Ala Ala Pro Ser Ser Ala Ala Ala Ala Ala Ala Glu
1               5                   10                  15

Val Glu Gln Arg Arg Arg Pro Gly Leu Cys Pro Pro Pro Leu Glu Leu
                20                  25                  30

Leu Leu Leu Leu Leu Phe Ser Leu Gly Leu Leu His Ala Gly Asp Cys
            35                  40                  45

Gln Gln Pro Ala Gln Cys Arg Ile Gln Lys Cys Thr Thr Asp Phe Val
        50                  55                  60

Ser Leu Thr Ser His Leu Asn Ser Ala Val Asp Gly Phe Asp Ser Glu
65                  70                  75                  80

Phe Cys Lys Ala Leu Arg Ala Tyr Ala Gly Cys Thr Gln Arg Thr Ser
                85                  90                  95

Lys Ala Cys Arg Gly Asn Leu Val Tyr His Ser Ala Val Leu Gly Ile
                100                 105                 110

Ser Asp Leu Met Ser Gln Arg Asn Cys Ser Lys Asp Gly Pro Thr Ser
            115                 120                 125

Ser Thr Asn Pro Glu Val Thr His Asp Pro Cys Asn Tyr His Ser His
        130                 135                 140
```

```
Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
            180                 185                 190

Asn Tyr Leu Ser Val Gln Val Thr Asn Val Pro Val Val Pro Gly Ser
        195                 200                 205

Ser Ala Thr Ala Thr Asn Lys Ile Thr Ile Ile Phe Lys Ala His His
    210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
                260                 265                 270

Ala Arg Tyr Ile Gly Thr Thr Val Phe Val Arg Gln Val Gly Arg Tyr
            275                 280                 285

Leu Thr Leu Ala Ile Arg Met Pro Glu Asp Leu Ala Met Ser Tyr Glu
    290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
                340                 345                 350

Thr Ala Asn Thr Gln Cys His Glu Lys Met Pro Val Lys Asp Ile Tyr
            355                 360                 365

Phe Gln Ser Cys Val Phe Asp Leu Leu Thr Thr Gly Asp Ala Asn Phe
    370                 375                 380

Thr Ala Ala His Ser Ala Leu Glu Asp Val Glu Ala Leu His Pro
385                 390                 395                 400

Arg Lys Glu Arg Trp His Ile Phe Pro Ser Ser Gly Asn Gly Thr Pro
                405                 410                 415

Arg Gly Gly Ser Asp Leu Ser Val Ser Leu Gly Leu Thr Cys Leu Ile
                420                 425                 430

Leu Ile Val Phe Leu
        435

<210> SEQ ID NO 9
<211> LENGTH: 426
<212> TYPE: PRT
<213> ORGANISM: Mus musculus

<400> SEQUENCE: 9

Met Gly Glu Pro Gly Gln Ser Pro Ser Pro Arg Ser Ser His Gly Ser
 1               5                  10                  15

Pro Pro Thr Leu Ser Thr Leu Thr Leu Leu Leu Leu Cys Gly Leu
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Ser Ser Gly Ala Leu Arg Gly
    50                  55                  60

Gly Gly Gly Gly Gly Arg Gly Gly Val Gly Ser Gly Gly Leu Cys
```

```
            65                  70                  75                  80
Arg Ala Leu Arg Ser Tyr Ala Leu Cys Thr Arg Thr Ala Arg Thr
                    85                  90                  95

Cys Arg Gly Asp Leu Ala Phe His Ser Ala Val His Gly Ile Glu Asp
                100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 10
<211> LENGTH: 450
<212> TYPE: PRT
<213> ORGANISM: Mus musculus

<400> SEQUENCE: 10

Met Gln Pro Pro Arg Glu Arg Leu Val Val Thr Gly Arg Ala Gly Trp
1               5                   10                  15
```

-continued

Met Gly Met Gly Arg Gly Ala Gly Arg Ser Ala Leu Gly Phe Trp Pro
            20                  25                  30
Thr Leu Ala Phe Leu Leu Cys Ser Phe Pro Ala Ala Thr Ser Pro Cys
                35                  40                  45
Lys Ile Leu Lys Cys Asn Ser Glu Phe Trp Ser Ala Thr Ser Gly Ser
 50                  55                  60
His Ala Pro Ala Ser Asp Asp Thr Pro Glu Phe Cys Ala Ala Leu Arg
 65                  70                  75                  80
Ser Tyr Ala Leu Cys Thr Arg Arg Thr Ala Arg Thr Cys Arg Gly Asp
                85                  90                  95
Leu Ala Tyr His Ser Ala Val His Gly Ile Glu Asp Leu Met Ser Gln
                100                 105                 110
His Asn Cys Ser Lys Asp Gly Pro Thr Ser Gln Pro Arg Leu Arg Thr
            115                 120                 125
Leu Pro Pro Ala Gly Asp Ser Gln Glu Arg Ser Asp Ser Pro Glu Ile
 130                 135                 140
Cys His Tyr Glu Lys Ser Phe His Lys His Ser Ala Thr Pro Asn Tyr
 145                 150                 155                 160
Thr His Cys Gly Leu Phe Gly Asp Pro His Leu Arg Thr Phe Thr Asp
                165                 170                 175
Arg Phe Gln Thr Cys Lys Val Gln Gly Ala Trp Pro Leu Ile Asp Asn
            180                 185                 190
Asn Tyr Leu Asn Val Gln Val Thr Asn Thr Pro Val Leu Pro Gly Ser
            195                 200                 205
Ala Ala Thr Ala Thr Ser Lys Leu Thr Ile Ile Phe Lys Asn Phe Gln
 210                 215                 220
Glu Cys Val Asp Gln Lys Val Tyr Gln Ala Glu Met Asp Glu Leu Pro
 225                 230                 235                 240
Ala Ala Phe Val Asp Gly Ser Lys Asn Gly Gly Asp Lys His Gly Ala
                245                 250                 255
Asn Ser Leu Lys Ile Thr Glu Lys Val Ser Gly Gln His Val Glu Ile
            260                 265                 270
Gln Ala Lys Tyr Ile Gly Thr Thr Ile Val Val Arg Gln Val Gly Arg
            275                 280                 285
Tyr Leu Thr Phe Ala Val Arg Met Pro Glu Glu Val Val Asn Ala Val
 290                 295                 300
Glu Asp Trp Asp Ser Gln Gly Leu Tyr Leu Cys Leu Arg Gly Cys Pro
 305                 310                 315                 320
Leu Asn Gln Gln Ile Asp Phe Gln Ala Phe His Thr Asn Ala Glu Gly
                325                 330                 335
Thr Gly Ala Arg Arg Leu Ala Ala Ala Ser Pro Ala Pro Thr Ala Pro
            340                 345                 350
Glu Thr Phe Pro Tyr Glu Thr Ala Val Ala Lys Cys Lys Glu Lys Leu
            355                 360                 365
Pro Val Glu Asp Leu Tyr Tyr Gln Ala Cys Val Phe Asp Leu Leu Thr
 370                 375                 380
Thr Gly Asp Val Asn Phe Thr Leu Ala Ala Tyr Tyr Ala Leu Glu Asp
 385                 390                 395                 400
Val Lys Met Leu His Ser Asn Lys Asp Lys Leu His Leu Tyr Glu Arg
                405                 410                 415
Thr Arg Asp Leu Pro Gly Arg Ala Ala Ala Gly Leu Pro Leu Ala Pro
            420                 425                 430
Arg Pro Leu Leu Gly Ala Leu Val Pro Leu Leu Ala Leu Leu Pro Val

```
            435                 440                 445

Phe Cys
    450

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

Thr Ala Ala Ala His Ser Ala Leu Glu Asp Val Glu Ala Leu His Pro
1               5                   10                  15

Arg Lys

<210> SEQ ID NO 12
<211> LENGTH: 93
<212> TYPE: PRT
<213> ORGANISM: Artificial Sequence
<220> FEATURE:
<223> OTHER INFORMATION: Synthetic

<400> SEQUENCE: 12

Pro Leu Pro Pro Pro Leu Leu Pro Leu Leu Pro Leu Leu Leu Leu Leu
1               5                   10                  15

Leu Gly Ala Ser Gly Gly Gly Gly Ala Arg Ala Glu Val Leu Phe
            20                  25                  30

Arg Cys Pro Pro Cys Thr Pro Glu Arg Leu Ala Ala Cys Gly Pro Pro
        35                  40                  45

Pro Val Ala Pro Pro Ala Ala Val Val Met Gly Glu Gly Thr Cys Glu
    50                  55                  60

Asp Arg Arg Asp Ala Glu Tyr Gly Ala Ser Pro Glu Gln Val Ala Asp
65                  70                  75                  80

Asn Gly Asp Asp His Ser Glu Gly Gly Leu Val Glu Asn
                85                  90

<210> SEQ ID NO 13
<211> LENGTH: 78
<212> TYPE: PRT
<213> ORGANISM: Artificial Sequence
<220> FEATURE:
<223> OTHER INFORMATION: Synthetic

<400> SEQUENCE: 13

Pro Pro Ser Pro Pro Gly Leu Leu Pro Leu Leu Pro Pro Leu Leu
1               5                   10                  15

Leu Leu Pro Leu Leu Leu Leu Pro Ala Gly Cys Arg Ala Leu Glu Glu
            20                  25                  30

Thr Leu Met Asp Thr Lys Trp Val Thr Ser Glu Leu Ala Trp Thr Ser
        35                  40                  45

His Pro Glu Ser Gly Trp Glu Glu Val Ser Gly Tyr Asp Glu Ala Met
    50                  55                  60

Asn Pro Ile Arg Thr Tyr Gln Val Cys Asn Val Arg Glu Ser
65                  70                  75

<210> SEQ ID NO 14
<211> LENGTH: 148
<212> TYPE: PRT
<213> ORGANISM: Artificial Sequence
<220> FEATURE:
```

<223> OTHER INFORMATION: Synthetic

<400> SEQUENCE: 14

```
Pro Gly Ala Arg Gly Arg Arg Arg Arg Pro Met Ser Pro
1               5                   10                  15
Pro Pro Pro Pro Pro Val Arg Ala Leu Pro Leu Leu Leu Leu Leu Ala
            20                  25                  30
Gly Pro Gly Ala Ala Ala Pro Pro Cys Leu Asp Gly Ser Pro Cys Ala
        35                  40                  45
Asn Gly Gly Arg Cys Thr Gln Leu Pro Ser Arg Glu Ala Ala Cys Leu
50                  55                  60
Cys Pro Pro Gly Trp Val Gly Glu Arg Cys Gln Leu Glu Asp Pro Cys
65                  70                  75                  80
His Ser Gly Pro Cys Ala Gly Arg Gly Val Cys Gln Ser Ser Val Val
                85                  90                  95
Ala Gly Thr Ala Arg Phe Ser Cys Arg Cys Pro Arg Gly Phe Arg Gly
            100                 105                 110
Pro Asp Cys Ser Leu Pro Asp Pro Cys Leu Ser Ser Pro Cys Ala His
        115                 120                 125
Gly Ala Arg Cys Ser Val Gly Pro Asp Gly Arg Phe Leu Cys Ser Cys
130                 135                 140
Pro Pro Gly Tyr
145
```

<210> SEQ ID NO 15
<211> LENGTH: 166
<212> TYPE: PRT
<213> ORGANISM: Artificial Sequence
<220> FEATURE:
<223> OTHER INFORMATION: Synthetic

<400> SEQUENCE: 15

```
Gln Lys Leu His Val Gly Glu Glu Ser Lys Lys Asn Phe Leu Glu Lys
1               5                   10                  15
Leu Lys Arg Asp Val Glu Phe Leu Ala Gln Leu Lys Ile Met Asp Tyr
            20                  25                  30
Ser Leu Leu Val Gly Ile His Asp Val Asp Arg Ala Glu Gln Glu Glu
        35                  40                  45
Met Glu Val Glu Glu Arg Ala Glu Glu Glu Cys Glu Asn Asp Gly
    50                  55                  60
Val Gly Gly Ser Leu Leu Cys Ser Tyr Gly Thr Pro Pro Asp Ser Pro
65                  70                  75                  80
Gly Asn Leu Leu Ser Phe Pro Arg Phe Phe Gly Pro Gly Glu Phe Asp
                85                  90                  95
Pro Ser Val Asp Val Tyr Ala Met Lys Ser His Glu Ser Ala Pro Lys
            100                 105                 110
Lys Glu Val Tyr Phe Met Ala Ile Ile Asp Ile Leu Thr Pro Tyr Asp
        115                 120                 125
Ala Lys Lys Lys Ala Ala His Ala Ala Lys Thr Val Lys His Gly Ala
130                 135                 140
Gly Ala Glu Ile Ser Thr Val Asn Pro Glu Gln Tyr Ser Lys Arg Phe
145                 150                 155                 160
Asn Glu Phe Met Ser Asn
                165
```

<210> SEQ ID NO 16

```
<211> LENGTH: 114
<212> TYPE: PRT
<213> ORGANISM: Artificial Sequence
<220> FEATURE:
<223> OTHER INFORMATION: Synthetic

<400> SEQUENCE: 16

Glu Asn Cys Leu Thr Thr Lys Tyr Gly Cys Cys Pro Asp Gly Lys Gly
  1               5                  10                  15

Ala Ala Lys Gly His His Asn Glu Gly Cys Cys Val Tyr Ala Gln
             20                  25                  30

Tyr Gly Cys Cys Pro Asp Gly Lys Thr Ser Ala Lys Gly Ala Gly Phe
             35                  40                  45

Tyr Gly Cys Pro Asp Ser Cys Ala Gln Ser Gln Phe Gly Cys Cys Pro
 50                  55                  60

Asp Gly Lys Thr Pro Ala Arg Gly Ser His Lys Glu Gly Cys Pro Cys
 65                  70                  75                  80

Gln Tyr Thr Arg Tyr Gly Cys Cys Pro Asp Gly Glu Thr Thr Ala Leu
                 85                  90                  95

Gly Pro Arg Asn Asp Gly Cys Asp Asp Cys Arg Tyr Ala Lys Tyr Gly
                100                 105                 110

Cys Cys

<210> SEQ ID NO 17
<211> LENGTH: 112
<212> TYPE: PRT
<213> ORGANISM: Artificial Sequence
<220> FEATURE:
<223> OTHER INFORMATION: Synthetic

<400> SEQUENCE: 17

Glu Pro Cys His Lys Lys Val Cys Ala His Gly Met Cys Gln Pro Ser
  1               5                  10                  15

Ser Gln Ser Gly Phe Thr Cys Glu Cys Glu Glu Gly Trp Met Gly Pro
             20                  25                  30

Leu Cys Asp Gln Arg Thr Asn Asp Pro Cys Leu Gly Asn Lys Cys Val
             35                  40                  45

His Gly Thr Cys Leu Pro Ile Asn Ala Phe Ser Tyr Ser Cys Lys Cys
 50                  55                  60

Leu Glu Gly His Gly Gly Val Leu Cys Asp Glu Glu Asp Leu Phe
 65                  70                  75                  80

Asn Pro Cys Gln Met Ile Lys Cys Lys His Gly Lys Cys Arg Leu Ser
                 85                  90                  95

Gly Val Gly Gln Pro Tyr Cys Glu Cys Asn Ser Gly Phe Thr Gly Asp
                100                 105                 110

<210> SEQ ID NO 18
<211> LENGTH: 420
<212> TYPE: PRT
<213> ORGANISM: Canhorbitidtis elegans

<400> SEQUENCE: 18

Met Arg Arg His Trp Lys Glu Phe Glu Cys Glu Lys Trp Glu Ser Cys
  1               5                  10                  15

Asn Asp Asn Ser His Val Lys Arg Lys His Val Asn Thr Gly His Ile
             20                  25                  30

Cys Gly Gly Lys Phe Glu Leu Ser Glu Lys Asn Leu Ala Ala Lys Phe
             35                  40                  45
```

```
Lys Tyr Ser Gly Asp Thr Val Trp Arg Gly Arg Pro Asn Phe Leu Lys
    50                  55                  60
Ser Leu Cys Tyr Phe Asn Pro Pro Ser Asn Arg Lys Leu Lys Tyr
65                  70                  75                  80
Cys Ser Leu Phe Gly Asp Pro His Leu Ile Met Phe Asn Gly Ser Val
                    85                  90                  95
Gln Thr Cys Ser Glu Glu Gly Ala Arg Pro Leu Val Asp Asn Arg Tyr
                100                 105                 110
Phe Leu Val Gln Val Thr Asn Arg Asn Val Arg Gly Glu Ala Leu Thr
                115                 120                 125
Thr Thr Val Thr Lys Val Thr Val Leu Val Arg Lys His Asn Cys Thr
130                 135                 140
Ala Ser Leu Arg Tyr Glu Ala Ser Ser Asp Glu Glu Gly Leu Pro Arg
145                 150                 155                 160
Gly Phe Val Asp Gly Thr Thr Phe Gln Met Thr Ser Lys His Ser Val
                    165                 170                 175
Glu Val Leu Trp Gln Asp Asp Asn Tyr Val Glu Ile Ala Leu His Phe
                180                 185                 190
Ile His Ser Ser Ile His Ile Arg Arg Gln Gly Pro Tyr Leu Ser Val
                195                 200                 205
Ser Val Arg Ala Pro Thr Ile Val Leu Glu Thr Gly Gly Asp Val Ala
210                 215                 220
Arg Glu Leu Cys Trp Ser Gly Cys Arg Lys Ser Arg Ile Pro Ala
225                 230                 235                 240
Glu Leu Ala Val Glu Met Thr Lys Lys Phe Ala Glu Cys Tyr Arg Arg
                    245                 250                 255
Arg Val His Val Pro Lys Lys Val Ala Glu Glu Thr Thr Phe Leu Ser
                260                 265                 270
Glu Gln Lys Val Leu Pro Ile Tyr Asp Arg Cys Lys Asp Ile Gly Asn
                275                 280                 285
Ile Gly Val Phe Phe Asp Ala Ser Ala Arg Lys Ile Leu Asn Phe Arg
290                 295                 300
Val Ser Gly Ser Gln Val Thr Ser Leu Gln Asn Cys Lys Ala Arg Arg
305                 310                 315                 320
Gly Leu Arg Arg Gly Gln Ala Ile Ile Leu Glu Arg Tyr Phe Ser Ala
                    325                 330                 335
Pro Lys Pro Lys Lys Phe His Leu Cys Thr Ala Thr Gly Gly Gln Val
                340                 345                 350
Thr Ala Leu Gln Ser Phe Glu Ala Arg Arg Gly Leu Arg Arg Gly Gln
                355                 360                 365
Ala Thr Thr Val Glu Arg Cys Ile Ser Ala Pro Arg Asp Pro Thr Asp
370                 375                 380
Leu Lys Ile Phe Ala Leu Thr Asp Asn Cys Glu Glu Thr Lys Lys Tyr
385                 390                 395                 400
Trp Asn Phe Phe Arg Tyr Asp Ile Leu Cys Asp Thr His Ser Gln Asn
                    405                 410                 415
Phe Leu Leu Pro
            420

<210> SEQ ID NO 19
<211> LENGTH: 48
<212> TYPE: DNA
<213> ORGANISM: Artificial Sequence
<220> FEATURE:
<223> OTHER INFORMATION: Synthetic
```

```
<400> SEQUENCE: 19
tcgcacaaac actgtggtgc ctatgtagcg ggcatgcatc tctacgta        48

<210> SEQ ID NO 20
<211> LENGTH: 48
<212> TYPE: DNA
<213> ORGANISM: Artificial Sequence
<220> FEATURE:
<223> OTHER INFORMATION: Synthetic

<400> SEQUENCE: 20
cccagctgtc tgtcgaatga tgatagttgt tccaatgtag gcagctcg        48

<210> SEQ ID NO 21
<211> LENGTH: 48
<212> TYPE: DNA
<213> ORGANISM: Artificial Sequence
<220> FEATURE:
<223> OTHER INFORMATION: Synthetic Primer

<400> SEQUENCE: 21
ttgccatcct ccaaagcata gtaggcagcc agcgtgaagt tcacatca        48

<210> SEQ ID NO 22
<211> LENGTH: 32
<212> TYPE: DNA
<213> ORGANISM: Mus musculus
<220> FEATURE:
<223> OTHER INFORMATION: Synthetic Primer

<400> SEQUENCE: 22
ataagcttat gggcgtgaga gcagcacctt cc                        32

<210> SEQ ID NO 23
<211> LENGTH: 29
<212> TYPE: DNA
<213> ORGANISM: Mus musculus
<220> FEATURE:
<223> OTHER INFORMATION: Synthetic Primer

<400> SEQUENCE: 23
gaagtcgacg aaacaactcc tacaaaaac                            29

<210> SEQ ID NO 24
<211> LENGTH: 30
<212> TYPE: DNA
<213> ORGANISM: Mus musculus
<220> FEATURE:
<223> OTHER INFORMATION: Synthetic Primer

<400> SEQUENCE: 24
ctcaagcttc agcctactca atgccgaatc                           30

<210> SEQ ID NO 25
<211> LENGTH: 1311
<212> TYPE: DNA
<213> ORGANISM: Danio rerio

<400> SEQUENCE: 25
atgggtatgg ggagagcagg atcttactac cccggggctg agcgcctcat ctctccggta    60
ctacatctac tagtgctgtg caccctctcc tccctcactc ccataggtga gagtcaggtt   120
cagactcctc agtgccgcat ccagaagtgc actaccgact tcgtttctct gacgtcccat   180
```

| | |
|---|---|
| ctgaacccat cactggatgg ctttgatacg gagttctgca aggcgctgcg agcctattcg | 240 |
| gcctgtacgc agcgtacagc caagagctgc aggggaacc tggtcttcca ctccgccatg | 300 |
| ctgggcatca ctgaccttat gagccagagg aactgctcca aagacgggcc cacgtcctcc | 360 |
| acccatcccg tcatccctat cgagccttgc aactatcaca gccggcatca ccaccacgtg | 420 |
| tcgcggttcg ggacgggggt gcccgaacac cctcgtctga tgtacctgtt ctgtggcctg | 480 |
| ttcggggacc ctcatcttag gacttttaaa gaccagtttc aaacgtgtaa agttgaaggg | 540 |
| gcttggcctc tcattgataa caactacctg tcagtgcagg tcactaatgt tccagtggtt | 600 |
| tatggatcca gtgccacagc taccaataag atcacaataa tcttcaaacc ataccaagaa | 660 |
| tgcacagacc agaaggtcta ccaggccgtg acagacgacc ttccagccgc cttcgtagac | 720 |
| ggcaccatca gcggaggtga cagtgagacc cgcagcatct ggatcctgga gaaatctccc | 780 |
| ggtcggcatg tagaaatcca cgctgcgtac atcggggtca ccatcatcat acgccagcag | 840 |
| ggccgttacc tgacactagc tgtgcgaatg cctgaggaac tggccatggc ctttgatgaa | 900 |
| acgcaggacc tgcagctgtg catgaacggc tgccccacat cagagcgcat tgaccaggag | 960 |
| ggacacctcc agctgcccgt gcttggcctc cagcaggctg gctttcagca gcagcagcag | 1020 |
| cccagggtgg aagcccagag aggcgtcttc actcttgaaa gtgcctccag gaggtgcagg | 1080 |
| gaccaactgg aggtgaagga catctatttc cactcctgtg tgtttgacct gctcactaca | 1140 |
| ggagatgcca acttcaccac tgccgcctac aatgccctga agacatgga gacactgcat | 1200 |
| cccaaaaagg agcgctggca gattttcccc aactcggctt ccaggctgag tccttttca | 1260 |
| ttgcttctca ctgcactgct gagcagcttc cttatcgctg tgcttttata a | 1311 |

<210> SEQ ID NO 26
<211> LENGTH: 1233
<212> TYPE: DNA
<213> ORGANISM: Danio rerio

<400> SEQUENCE: 26

| | |
|---|---|
| atgggaatgg cagcatcagc tggtggtggg aatcactcac acacaacatg gaaacacatt | 60 |
| gtgatcattg tttcaatggt cctgctcttt agtgctccat cagtatgtgc gcagtgtcga | 120 |
| atcttgcgat gcaactcaga cttcgtggct gcgactttgg agagcggtgt cattggagga | 180 |
| ggcaataaag agggtgtaaa tacgggatac tgcagcgccc tgcgatccta cgccctctgc | 240 |
| acccagcgga cggcccgagc ctgcagggga gaccttgcgt atcactctgc tgtacagggc | 300 |
| atcgaggacc tgctcataca ataccgctgc ccaaaagcag gccccacggc tcagcctcag | 360 |
| cctcggcccc tgcccaagc ccctctctcc ggggatggat gcttctacga aagggtttt | 420 |
| atacagaggg agggccgggc cccagaatat ctacactgtg gggtgtttgg agacccgcat | 480 |
| atccgtacct tcaacgagga gttccagacg tgtgcagtgc agggcgcctg gcctctcata | 540 |
| gataaccagt atctgtacat ccaggccacc agcagtccca ccaggagag ctctgacacc | 600 |
| accatactca cagaggtcac ggtgatcttc cagaactggc gtgagtgcgc tgaacagcag | 660 |
| gtttatcaag caaaactggg caacgttcct ccagcgtttg cggacggctc tgtgactggc | 720 |
| ggggaccgca gagggcatca gagtctgcgt attcactcac aagacccagg ccggcatgct | 780 |
| gaaatctggg ctactcatat tgggaccatg ataatagtgc ggcaggttgg ccagtcgctg | 840 |
| agcctgtccg tccgctctcc tcgtgccatc gtggagtcct atacgccgga acaggacctg | 900 |
| cagttgtgtg tgtgggggtg tcccattcca caacgtttag agatgctgca tgcacatcca | 960 |
| ttcgaccccg catacacaca ctgttcctcg ctgtttccgg ggagagatgt gtatttccag | 1020 |

-continued

```
gcctgcctgt tgatgtgca ggtgaccggg gatgtgaact ccagcgcttc agctgtggct    1080
gcgttagagg acgctcgagc catgatttct gaccccgcga gtgttcattt ggtgactggt    1140
gggacgggta ataactcccc gtcattgctg gtggttctag gtttcagttt ccttacagag    1200
accctcagac acagttttt ggggtcagcg tga                                 1233
```

<210> SEQ ID NO 27
<211> LENGTH: 1302
<212> TYPE: DNA
<213> ORGANISM: Danio rerio

<400> SEQUENCE: 27

```
atggttatgg ggaaaggagc aggaccatcg gcgctacaag tctgccagtt ccttgcactg      60
tttctcagtc tgtttccagc agccactctg cagtgtaaga tcctcaagtg taactcagag     120
ttctgggcct ccacctccaa ttctggccca gaagaggagt tttgcactgc tctgcgagca     180
tacaacagtt gtgtacgtcg caccgctcgt acatgccggg gtgacctggc ctaccattca     240
gcccaacatg gtatagagga tcttatgagc aacacaact gctccaaaga agggcccact      300
acccagcctc gtgcccgcac agtcccaccc ccagtcttgt caccaccca aacagacatt      360
catattccct ctgacgagcc agaggtatgc cattatgagc ggagtctacc acgtaatgct     420
gcacctccca attacaccca ttgtggcttt tttggggatc cacatcttcg cacattcaac     480
gatgactttc aaacctgtaa agttgaggga gcctggccac ttatccacaa taagtacctg     540
tctgtccaag ttacaaacac tccagttgtt gttggatctt cagctacagc tactagcaag     600
ctaacaatca tcttcaacag ctttcaagaa tgcgtagacc agaagacgta ccgtgcagag     660
accgaagatc ttcctgctgc attcattgat ggttcgaaga atggaggtga gggccatggg     720
gccaacaccc tacgtgtggt agagaaggta cctggacaac atgtggagat ccaggcacgt     780
tatattggca caacaattgt agttcggaaa gttggccact accttacctt tgctgtgcgg     840
atgccagagg aggtggtaaa ttcagtggaa gaccaggaca atcaggatct ttacctctgc     900
ctgcatggtt gccctgccaa ccagcgaata gacttcagga cctttaaggc acgagcagca     960
gagagccatg gtgtaggccg gggacgtcca gggaacccct cctatggctt cacgtaccag   1020
tcagccatgg ccaagtgcaa agaacgtcta cctgttgagg atttgtactt caatcgtgt    1080
gttttgacc tgctatcttc cggggatatc aacttcactc tggcggccta ctacgccttt   1140
gaggatgtta aaatgctcca ctccaacaaa aacaagtacc atctctttga aaaggataca   1200
atatttaact ctgcctccag aaaattggcg tttagtattc taatcttcat cagctttgtc   1260
attgtgcagt tatggattga ctcgtgttcc atttgtctgt ag                      1302
```

<210> SEQ ID NO 28
<211> LENGTH: 436
<212> TYPE: PRT
<213> ORGANISM: Danio rerio

<400> SEQUENCE: 28

```
Met Gly Met Gly Arg Ala Gly Ser Tyr Tyr Pro Gly Ala Glu Arg Leu
  1               5                  10                  15

Ile Ser Pro Val Leu His Leu Val Leu Cys Thr Leu Ser Ser Leu
             20                  25                  30

Thr Pro Ile Gly Glu Ser Gln Val Gln Thr Pro Gln Cys Arg Ile Gln
         35                  40                  45

Lys Cys Thr Thr Asp Phe Val Ser Leu Thr Ser His Leu Asn Pro Ser
```

```
                50                  55                  60
Leu Asp Gly Phe Asp Thr Glu Phe Cys Lys Ala Leu Arg Ala Tyr Ser
 65                  70                  75                  80

Ala Cys Thr Gln Arg Thr Ala Lys Ser Cys Arg Gly Asn Leu Val Phe
                 85                  90                  95

His Ser Ala Met Leu Gly Ile Thr Asp Leu Met Ser Gln Arg Asn Cys
                100                 105                 110

Ser Lys Asp Gly Pro Thr Ser Ser Thr His Pro Val Ile Pro Ile Glu
                115                 120                 125

Pro Cys Asn Tyr His Ser Arg His His His Val Ser Arg Phe Gly
                130                 135                 140

Thr Gly Val Pro Glu His Pro Arg Leu Met Tyr Leu Phe Cys Gly Leu
145                 150                 155                 160

Phe Gly Asp Pro His Leu Arg Thr Phe Lys Asp Gln Phe Gln Thr Cys
                165                 170                 175

Lys Val Glu Gly Ala Trp Pro Leu Ile Asp Asn Asn Tyr Leu Ser Val
                180                 185                 190

Gln Val Thr Asn Val Pro Val Val Tyr Gly Ser Ser Ala Thr Ala Thr
                195                 200                 205

Asn Lys Ile Thr Ile Ile Phe Lys Pro Tyr Gln Glu Cys Thr Asp Gln
210                 215                 220

Lys Val Tyr Gln Ala Val Thr Asp Asp Leu Pro Ala Ala Phe Val Asp
225                 230                 235                 240

Gly Thr Ile Ser Gly Gly Asp Ser Glu Thr Arg Ser Ile Trp Ile Leu
                245                 250                 255

Glu Lys Ser Pro Gly Arg His Val Glu Ile His Ala Ala Tyr Ile Gly
                260                 265                 270

Val Thr Ile Ile Ile Arg Gln Gln Gly Arg Tyr Leu Thr Leu Ala Val
                275                 280                 285

Arg Met Pro Glu Glu Leu Ala Met Ala Phe Asp Glu Thr Gln Asp Leu
                290                 295                 300

Gln Leu Cys Met Asn Gly Cys Pro Thr Ser Glu Arg Ile Asp Gln Glu
305                 310                 315                 320

Gly His Leu Gln Leu Pro Val Leu Gly Leu Gln Ala Gly Phe Gln
                325                 330                 335

Gln Gln Gln Gln Pro Arg Val Glu Ala Gln Arg Gly Val Phe Thr Leu
                340                 345                 350

Glu Ser Ala Ser Arg Arg Cys Arg Asp Gln Leu Glu Val Lys Asp Ile
                355                 360                 365

Tyr Phe His Ser Cys Val Phe Asp Leu Leu Thr Thr Gly Asp Ala Asn
                370                 375                 380

Phe Thr Thr Ala Ala Tyr Asn Ala Leu Lys Asp Met Glu Thr Leu His
385                 390                 395                 400

Pro Lys Lys Glu Arg Trp Gln Ile Phe Pro Asn Ser Ala Ser Arg Leu
                405                 410                 415

Ser Pro Phe Ser Leu Leu Leu Thr Ala Leu Leu Ser Ser Phe Leu Ile
                420                 425                 430

Ala Val Leu Leu
                435

<210> SEQ ID NO 29
<211> LENGTH: 410
<212> TYPE: PRT
<213> ORGANISM: Danio rerio
```

<400> SEQUENCE: 29

Met Gly Met Ala Ala Ser Ala Gly Gly Asn His Ser His Thr Thr
1               5                   10                  15

Trp Lys His Ile Val Ile Val Ser Met Val Leu Leu Phe Ser Ala
            20                  25                  30

Pro Ser Val Cys Ala Gln Cys Arg Ile Leu Arg Cys Asn Ser Asp Phe
            35                  40                  45

Val Ala Ala Thr Leu Glu Ser Gly Val Ile Gly Gly Asn Lys Glu
    50                  55                  60

Gly Val Asn Thr Gly Tyr Cys Ser Ala Leu Arg Ser Tyr Ala Leu Cys
65              70                  75                  80

Thr Gln Arg Thr Ala Arg Ala Cys Arg Gly Asp Leu Ala Tyr His Ser
                85                  90                  95

Ala Val Gln Gly Ile Glu Asp Leu Leu Ile Gln Tyr Arg Cys Pro Lys
                100                 105                 110

Ala Gly Pro Thr Ala Gln Pro Gln Pro Arg Pro Leu Pro Gln Ala Pro
            115                 120                 125

Leu Ser Gly Asp Gly Cys Phe Tyr Glu Lys Gly Phe Ile Gln Arg Glu
130                 135                 140

Gly Arg Ala Pro Glu Tyr Leu His Cys Gly Val Phe Gly Asp Pro His
145                 150                 155                 160

Ile Arg Thr Phe Asn Glu Glu Phe Gln Thr Cys Ala Val Gln Gly Ala
                165                 170                 175

Trp Pro Leu Ile Asp Asn Gln Tyr Leu Tyr Ile Gln Ala Thr Ser Ser
            180                 185                 190

Pro Thr Arg Glu Ser Ser Asp Thr Thr Ile Leu Thr Glu Val Thr Val
            195                 200                 205

Ile Phe Gln Asn Trp Arg Glu Cys Ala Glu Gln Val Tyr Gln Ala
210                 215                 220

Lys Leu Gly Asn Val Pro Pro Ala Phe Ala Asp Gly Ser Val Thr Gly
225                 230                 235                 240

Gly Asp Arg Arg Gly His Gln Ser Leu Arg Ile His Ser Gln Asp Pro
            245                 250                 255

Gly Arg His Ala Glu Ile Trp Ala Thr His Ile Gly Thr Met Ile Ile
        260                 265                 270

Val Arg Gln Val Gly Gln Ser Leu Ser Leu Ser Val Arg Ser Pro Arg
            275                 280                 285

Ala Ile Val Glu Ser Tyr Thr Pro Glu Gln Asp Leu Gln Leu Cys Val
    290                 295                 300

Trp Gly Cys Pro Ile Ser Gln Arg Leu Glu Met Leu His Ala His Pro
305                 310                 315                 320

Phe Asp Pro Ala Tyr Thr His Cys Ser Ser Leu Phe Pro Gly Arg Asp
                325                 330                 335

Val Tyr Phe Gln Ala Cys Leu Phe Asp Val Gln Val Thr Gly Asp Val
                340                 345                 350

Asn Ser Ser Ala Ser Ala Val Ala Leu Glu Asp Ala Arg Ala Met
            355                 360                 365

Ile Ser Asp Pro Ala Ser Val His Leu Val Thr Gly Gly Thr Gly Asn
            370                 375                 380

Asn Ser Pro Ser Leu Leu Val Val Leu Gly Phe Ser Phe Leu Thr Glu
385                 390                 395                 400

Thr Leu Arg His Ser Phe Leu Gly Ser Ala

```
                    405                 410

<210> SEQ ID NO 30
<211> LENGTH: 433
<212> TYPE: PRT
<213> ORGANISM: Danio rerio

<400> SEQUENCE: 30

Met Val Met Gly Lys Gly Ala Gly Pro Ser Ala Leu Gln Val Cys Gln
 1               5                  10                  15

Phe Leu Ala Leu Phe Leu Ser Leu Phe Pro Ala Ala Thr Leu Gln Cys
            20                  25                  30

Lys Ile Leu Lys Cys Asn Ser Glu Phe Trp Ala Ser Thr Ser Asn Ser
        35                  40                  45

Gly Pro Glu Glu Phe Cys Thr Ala Leu Arg Ala Tyr Asn Ser Cys
 50                  55                  60

Val Arg Arg Thr Ala Arg Thr Cys Arg Gly Asp Leu Ala Tyr His Ser
 65                  70                  75                  80

Ala Gln His Gly Ile Glu Asp Leu Met Ser Gln His Asn Cys Ser Lys
                85                  90                  95

Glu Gly Pro Thr Thr Gln Pro Arg Ala Arg Thr Val Pro Pro Pro Val
           100                 105                 110

Leu Ser Pro Pro Gln Thr Asp Ile His Ile Pro Ser Asp Glu Pro Glu
       115                 120                 125

Val Cys His Tyr Glu Arg Ser Leu Pro Arg Asn Ala Ala Pro Pro Asn
130                 135                 140

Tyr Thr His Cys Gly Phe Phe Gly Asp Pro His Leu Arg Thr Phe Asn
145                 150                 155                 160

Asp Asp Phe Gln Thr Cys Lys Val Glu Gly Ala Trp Pro Leu Ile His
                165                 170                 175

Asn Lys Tyr Leu Ser Val Gln Val Thr Asn Thr Pro Val Val Val Gly
            180                 185                 190

Ser Ser Ala Thr Ala Thr Ser Lys Leu Thr Ile Ile Phe Asn Ser Phe
        195                 200                 205

Gln Glu Cys Val Asp Gln Lys Thr Tyr Arg Ala Glu Thr Glu Asp Leu
210                 215                 220

Pro Ala Ala Phe Ile Asp Gly Ser Lys Asn Gly Gly Glu Gly His Gly
225                 230                 235                 240

Ala Asn Thr Leu Arg Val Val Glu Lys Val Pro Gly Gln His Val Glu
                245                 250                 255

Ile Gln Ala Arg Tyr Ile Gly Thr Thr Ile Val Val Arg Lys Val Gly
            260                 265                 270

His Tyr Leu Thr Phe Ala Val Arg Met Pro Glu Glu Val Val Asn Ser
        275                 280                 285

Val Glu Asp Gln Asp Asn Gln Asp Leu Tyr Leu Cys Leu His Gly Cys
290                 295                 300

Pro Ala Asn Gln Arg Ile Asp Phe Arg Thr Phe Lys Ala Arg Ala Ala
305                 310                 315                 320

Glu Ser His Gly Val Gly Arg Gly Arg Pro Gly Asn Pro Ser Tyr Gly
                325                 330                 335

Phe Thr Tyr Gln Ser Ala Met Ala Lys Cys Lys Glu Arg Leu Pro Val
            340                 345                 350

Glu Asp Leu Tyr Phe Gln Ser Cys Val Phe Asp Leu Leu Ser Ser Gly
        355                 360                 365
```

| Asp | Ile | Asn | Phe | Thr | Leu | Ala | Ala | Tyr | Tyr | Ala | Phe | Glu | Asp | Val | Lys |
|---|---|---|---|---|---|---|---|---|---|---|---|---|---|---|---|
| 370 | | | | 375 | | | | | 380 | | | | | | |

| Met | Leu | His | Ser | Asn | Lys | Asn | Lys | Tyr | His | Leu | Phe | Glu | Lys | Asp | Thr |
|---|---|---|---|---|---|---|---|---|---|---|---|---|---|---|---|
| 385 | | | | | 390 | | | | | 395 | | | | | 400 |

| Ile | Phe | Asn | Ser | Ala | Ser | Arg | Lys | Leu | Ala | Phe | Ser | Ile | Leu | Ile | Phe |
|---|---|---|---|---|---|---|---|---|---|---|---|---|---|---|---|
| | | | | 405 | | | | | 410 | | | | | 415 | |

| Ile | Ser | Phe | Val | Ile | Val | Gln | Leu | Trp | Ile | Asp | Ser | Cys | Ser | Ile | Cys |
|---|---|---|---|---|---|---|---|---|---|---|---|---|---|---|---|
| | | | 420 | | | | | 425 | | | | | 430 | | |

Leu

<210> SEQ ID NO 31
<211> LENGTH: 2145
<212> TYPE: DNA
<213> ORGANISM: Homo sapiens

<400> SEQUENCE: 31

| | | | | | |
|---|---|---|---|---|---|
| attgcagcca | gtccggggga | tcggggacag | acatggagaa | ggagatggag | gaccccctgg | 60 |
| ctggagcaga | ccaacagaat | aggcaactat | ggctggagaa | ccgggtatca | gagtaatgct | 120 |
| tgacctcggg | aaacaccaaa | tttcttcttc | cgatcgcaga | agtagtactc | ggcgaaattc | 180 |
| actaggtagg | aggctcctca | tctgggaaga | accggtgcct | gggggaccct | ggctggatag | 240 |
| gtatggggga | tcgaggccgg | tcccctagtc | tccggtcccc | ccatggcagt | cctccaactc | 300 |
| taagcaccct | cactctcctg | ctgctcctct | gtggacaggc | tcactcccag | tgcaagatcc | 360 |
| tccgctgcaa | tgccgagtac | gtctcgttca | ctctgagcct | tcggggaggg | ggctcaccgg | 420 |
| acacgccacg | tggaggcggc | cgtggtgggc | cggcctcagg | tggcttgtgt | cgcgccctgc | 480 |
| gctcctacgc | tctctgcacg | cggcgcaccg | cccgcacctg | ccgcggggac | ctcgctttcc | 540 |
| actccgcggt | gcatggcata | gaggacctga | tgatccagca | caactgctca | cgccagggtc | 600 |
| ccacggcctc | gccccggcc | cggggtcctg | cctgcccgg | gccggccca | gcgcccctga | 660 |
| ccccagatcc | ctgtgactat | gaagcccggt | tttccaggct | gcacggtcga | accccgggtt | 720 |
| tcttgcattg | tgcttccttt | ggagaccccc | atgtgcgcag | cttccacaat | cactttcaca | 780 |
| catgccgcgt | ccaaggagct | tggccccctac | tagataacga | cttcctcttt | gtccaagcca | 840 |
| ccagctcccc | ggtagcatcg | ggagccaacg | ctaccaccat | ccggaagatc | actatcatat | 900 |
| ttaaaaacat | gcaggaatgc | attgaccaga | aagtctacca | ggctgaggta | gacaatcttc | 960 |
| ctgcagcctt | tgaagatggt | tctgtcaatg | ggggcgaccg | acctgggggc | tcgagtttgt | 1020 |
| ccattcaaac | tgctaaccctt | gggagccacg | tggagattcg | agctgcctac | attggaacaa | 1080 |
| ctataatcgt | tcgtcagaca | gctggacagc | tctccttctc | catcagggta | gcggaggatg | 1140 |
| tggcacgggc | cttctctgct | gagcaggatc | tacagctgtg | tgttggggga | tgccctccga | 1200 |
| gccagcgact | ctctcgctca | gagcgcaatc | gccgtggggc | gatagccata | gatactgcca | 1260 |
| gaaggttgtg | taaggaaggg | cttccggttg | aagatgccta | cttccaatcc | tgcgtctttg | 1320 |
| atgtttcagt | ctccggtgac | cccaacttta | ctgtggcagc | tcagtcagct | ctggacgatg | 1380 |
| cccgagtctt | cttgaccgat | ttggagaact | tgcacctttt | cccagtagat | gcggggcctc | 1440 |
| ccctctctcc | agccacctgc | ctagtccggc | ttctttcggt | cctctttgtt | ctgtggtttt | 1500 |
| gcattcagta | agtaggccag | caacccgtga | ctagtttgga | aacggtttga | ggagagaggt | 1560 |
| tgatgtgaga | aaacacaaag | atgtgccaaa | ggaaacagtg | gggacaggag | acaacgacct | 1620 |
| tactcaatca | cacgaggttg | cagtccaggg | ctgaaatgac | cctagaataa | agattctgag | 1680 |
| acagggtttt | gcactccaga | ccttggtatg | ggctccccat | gtatttcccc | attagtgatt | 1740 |

```
tcccacttgt agtgaaattc tactctctgt acacctgata tcactcctgc aaggctagag    1800
attgtgagag cgctaagggc cagcaaaaca ttaaagggct gagatatctt aaaggcagaa    1860
actagaaaag gggaaaccat gattatctat aagaaaatca aaagaggggt ttgggaattt    1920
agctcagtgg tagagcactt gcctagcaag cgcaaggccc tggttcggt ccccagctcc     1980 taaaaaagaa aaaaaaatc aaaagagaaa aaactaatta aggcaagctt tttggttcag     2040
aaatgaagtg ggcattgtct ggcagaggaa gtcagctttt ggagactggc accaacatct    2100
ccacccttcc tactctgtta ttaaagtgac gaattcccca tcctg                    2145
```

<210> SEQ ID NO 32
<211> LENGTH: 3216
<212> TYPE: DNA
<213> ORGANISM: Homo sapiens

<400> SEQUENCE: 32

```
agttgtctcc cgagcgctgg ctgcgccgcc cgagccgctg ggccggggaa gcactggccg     60
ttcgctcccg ggccggcccc gccaggcgct cgcaggcatg cagcccggga gcaggaggcg    120
ctccccgggc cgctgctgag ccggccgggg cggcggggac cagcgccagc ggagcccctc    180
ccaccttgcc ccggggcaga cgagcggcgc cccgacaccc cctcttctcc cgcagccccg    240
ccagcgccac ccccgcggg ccgcagggcc tcatgcagcc gccaagggag aggctagtgg     300
taacaggccg agctggatgg atgggtatgg ggagaggggc aggacgttca gccctgggat    360
tctggccgac cctcgccttc cttctctgca gcttccccgc agccaccttcc ccgtgcaaga   420 tcctcaagtg caactctgag ttctggagcg ccacgtcggg cagccacgcc ccagcctcag    480
acgacacccc cgagttctgt gcagccttgc gcagctacgc cctgtgcacg cggcggacgg    540
cccgcacctg ccggggtgac ctggcctacc actcggccgt ccatggcata gaggacctca   600
tgagccagca caactgctcc aaggatggcc ccacctcgca gccacgcctg cgcacgctcc    660
caccggccgg agacagccag gagcgctcgg acagccccga gatctgccat tacgagaaga   720
gctttcacaa gcactcggcc ccccccaact acacgcactg tggcctcttc ggggacccac    780
acctcaggac tttcaccgac cgcttccaga cctgcaaggt gcagggcgcc tggccgctca    840
tcgacaataa ttacctgaac gtgcaggcca ccaacacgcc tgtgctgccc ggctcagcgg    900
ccactgccac cagcaagctc accatcatct tcaagaactt ccaggagtgt gtggaccaga    960
aggtgtacca ggctgagatg gacgagctcc cggccgcctt cgtggatggc tctaagaacg   1020
gtggggacaa gcacggggcc aacagcctga agatcactga gaaggtgtca ggccagcacg   1080
tggagatcca ggccaagtac atcggcacca ccatcgtggt gcgccaggtg ggccgctacc   1140 tgaccttgc cgtccgcatg ccagaggaag tggtcaatgc tgtggaggac tgggacagcc    1200
agggtctcta cctctgcctg cggggctgcc ccctcaacca gcagatcgac ttccaggcct   1260
tccacaccaa tgctgagggc accggtgccc gcaggctggc agccgccagc cctgcaccca   1320
cagcccccga gaccttccca tacgagacag ccgtggccaa gtgcaaggag aagctgccgg    1380
tggaggacct gtactaccag gcctgcgtct tcgacctcct caccacgggc gacgtgaact   1440
tcacactggc cgcctactac gcgttggagg atgtcaagat gctccactcc aacaaagaca   1500
aactgcacct gtatgagagg actcgggacc tgccaggcag ggcggctgcg gggctgcccc    1560 tggcccccg gccctcctg ggcgccctcg tccgctcct ggcctgctc cctgtgttct       1620 gctagacgcg tagatgtgga gggaggcgcg ggctccgtcc tctcggcttc cccatgtgtg   1680
```

```
ggctgggacc gcccacgggg tgcagatctc ctggcgtgtc caccatggcc ccgcagaacg    1740
ccagggaccg cctgctgcca agggctcagg catggacccc tcccttcta gtgcacgtga     1800 caaggttgtg gtgactggtg ccgtgatgtt tgacagtaga gctgtgtgag agggagagca    1860
gctcccctcg ccccgcccct gcagtgtgaa tgtgtgaaac atcccctcag ctgaagccc     1920 cccacccca ccagagacac actgggaacc gtcagagtca gctccttccc cctcgcaatg     1980
cactgaaagg cccggccgac tgctgctcgc tgatccgtgg ggcccctgt gcccgccaca     2040 cgcacgcaca cactcttaca cgagagcaca ctcgatcccc ctaggccagc ggggacaccc    2100
cagccacaca gggaggcatc cttggggctt ggccccaggc agggcaaccc cggggcgctg    2160
cttggcacct tagcagactg ctggaacctt ttggccagta ggtcgtgccc gcctggtgcc    2220
ttctggcctg tggcctccct gcccatgttc acctggctgc tgtgggtacc agtgcaggtc    2280
ccggttttca ggcacctgct cagctgcccg tctctggcct gggcccctgc ccttccacc     2340 ctgtgcttag aaagtcgaag tgcttggttc taaatgtcta aacagagaag agatccttga    2400
cttctgttcc tctccctcct gcagatgcaa gagctcctgg gcagggtgc ctgggcccca     2460 gggtgtggca ggagacccag tggatggggc cagctggcct gccctgatcc tctgcttcct    2520
cctcacaacc ccaagagccc ccagcccggt ccatccacgt ctggagtctg gggagaggag    2580
cagggtctta ggactctcag ctctgagcat ccctggcagg gtcttcaacc tctaatctct    2640
tcccttaagc cctgtggcca cacagccagg agagacttgc cgctggctcc cgcctcattt    2700
cagcccaggg tgctcatcca ggggcccaga acagtcccac ctgtgctgct atgcccacag    2760
cacaaagcca ggcttcactc ccaaaagtgc agccaggccc tggagggtga tcctgccagc    2820
agccctacag ctccacaccc tacccaccca tcggcagcct ctctgctgtt ccccagggac    2880
ctctcataca ctggccagga ggctgcagaa cgtgtgtctc cccctccctc caagaggtcc    2940
tgctccctct gccagaaccg tgtgtgggcg ggtgggaggg cgctcggggc ccggcccctc    3000
cctctccctg ctggttttag ttggtcccta tgttggaagt aaaaagtgaa gcactttatt    3060
ttggttgtgt ttgctcacgt tctgcttgga agtggggacc cctcactgcg tccacgtgtc    3120
tgcgacctgt gtggagtgtc accgcgtgta catactgtaa attatttatt aatggctaaa    3180
tgcaagtaaa gtttggtttt tttgttattt tctttt                             3216
```

<210> SEQ ID NO 33
<211> LENGTH: 419
<212> TYPE: PRT
<213> ORGANISM: Mus musculus

<400> SEQUENCE: 33

```
Met Gly Gln Ser Pro Ser Pro Arg Ser Pro His Gly Ser Pro Pro Thr
 1               5                  10                  15

Leu Ser Thr Leu Thr Leu Leu Leu Leu Cys Gly Gln Ala His Ser
             20                  25                  30

Gln Cys Lys Ile Leu Arg Cys Asn Ala Glu Tyr Val Ser Ser Thr Leu
         35                  40                  45

His Leu Arg Gly Gly Gly Ser Pro Asp Thr Pro Arg Gly Gly Gly Arg
     50                  55                  60

Gly Gly Leu Ala Ser Gly Leu Cys Arg Ala Leu Arg Ser Tyr Ala
 65                  70                  75                  80

Leu Cys Thr Arg Arg Thr Ala Arg Thr Cys Arg Gly Asp Leu Ala Phe
                 85                  90                  95

His Ser Ala Val His Gly Ile Glu Asp Leu Met Ile Gln His Asn Cys
```

```
            100                 105                 110
Ser Arg Gln Gly Pro Thr Ala Pro Pro Ala Arg Gly Pro Ala Leu
        115                 120                 125

Pro Gly Ala Gly Pro Ala Pro Leu Thr Pro Asp Pro Cys Asp Tyr Glu
130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Ile Arg Gln Thr Ala Gly Gln Leu Ser
        275                 280                 285

Phe Ser Ile Arg Val Ala Glu Asp Val Ala Arg Ala Phe Ser Ala Glu
    290                 295                 300

Gln Asp Leu Gln Leu Cys Val Gly Gly Cys Pro Pro Ser Gln Arg Leu
305                 310                 315                 320

Ser Arg Ser Glu Arg Asn Arg Arg Gly Ala Ile Ala Ile Asp Thr Ala
                325                 330                 335

Arg Arg Leu Cys Lys Glu Gly Leu Pro Val Glu Asp Ala Tyr Phe Gln
            340                 345                 350

Ser Cys Val Phe Asp Val Ser Val Ser Gly Asp Pro Asn Phe Thr Val
        355                 360                 365

Ala Ala Gln Thr Ala Leu Asp Asp Ala Arg Ile Phe Leu Thr Asp Leu
    370                 375                 380

Glu Asn Leu His Leu Phe Pro Ser Asp Ala Gly Pro Pro Leu Ser Pro
385                 390                 395                 400

Ala Ile Cys Leu Val Pro Leu Leu Ser Ala Leu Phe Val Trp Leu Cys
                405                 410                 415

Phe Ser Lys

<210> SEQ ID NO 34
<211> LENGTH: 454
<212> TYPE: PRT
<213> ORGANISM: Mus musculus

<400> SEQUENCE: 34

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Leu Trp Pro
                20                  25                  30

Thr Leu Ala Phe Leu Leu Cys Ser Phe Pro Ala Ala Ile Ser Pro Cys
            35                  40                  45

Lys Ile Leu Lys Cys Asn Ser Glu Phe Trp Ser Ala Thr Ser Ser Gly
```

```
                50                  55                  60
Ser His Ala Pro Ala Ser Asp Asp Val Pro Glu Phe Cys Ala Ala Leu
 65                  70                  75                  80

Arg Thr Tyr Ala Leu Cys Thr Arg Arg Thr Ala Arg Thr Cys Arg Gly
                     85                  90                  95

Asp Leu Ala Tyr His Ser Ala Val His Gly Ile Glu Asp Leu Met Ser
                    100                 105                 110

Gln His Asn Cys Ser Lys Asp Gly Pro Thr Ser Gln Pro Arg Val Arg
                    115                 120                 125

Thr Leu Pro Pro Ala Gly Asp Ser Gln Glu Arg Ser Asp Ser Pro Glu
                130                 135                 140

Ile Cys His Tyr Glu Lys Ser Phe His Lys His Ser Ala Ala Pro Asn
145                 150                 155                 160

Tyr Thr His Cys Gly Leu Phe Gly Asp Pro His Leu Arg Thr Phe Thr
                    165                 170                 175

Asp His Phe Gln Thr Cys Lys Val Gln Gly Ala Trp Pro Leu Ile Asp
                    180                 185                 190

Asn Asn Tyr Leu Asn Val Gln Val Thr Asn Thr Pro Val Leu Pro Gly
                    195                 200                 205

Ser Ala Ala Thr Ala Thr Ser Lys Leu Thr Ile Ile Phe Lys Asn Phe
                210                 215                 220

Gln Glu Cys Val Asp Gln Lys Val Tyr Gln Ala Glu Met Asp Glu Leu
225                 230                 235                 240

Pro Ser Ala Phe Ala Asp Gly Ser Lys Asn Gly Gly Asp Lys His Gly
                    245                 250                 255

Ala Asn Ser Leu Lys Ile Thr Glu Lys Val Ser Gly Gln His Val Glu
                    260                 265                 270

Ile Gln Ala Lys Tyr Ile Gly Thr Thr Ile Val Val Arg Gln Val Gly
                    275                 280                 285

Arg Tyr Leu Thr Phe Ala Val Arg Met Pro Glu Glu Val Val Asn Ala
                290                 295                 300

Val Glu Asp Arg Asp Ser Gln Gly Leu Tyr Leu Cys Leu Arg Gly Cys
305                 310                 315                 320

Pro Leu Asn Gln Gln Ile Asp Phe Gln Ala Phe Arg Ala Asn Ala Glu
                    325                 330                 335

Ser Pro Arg Arg Pro Ala Ala Ser Pro Ser Pro Val Val Pro Glu
                    340                 345                 350

Thr Phe Pro Tyr Glu Thr Ala Val Ala Lys Cys Lys Glu Lys Leu Pro
                    355                 360                 365

Val Glu Asp Leu Tyr Tyr Gln Ala Cys Val Phe Asp Leu Leu Thr Thr
                370                 375                 380

Gly Asp Val Asn Phe Thr Leu Ala Ala Tyr Tyr Ala Leu Glu Asp Gly
385                 390                 395                 400

Lys Met Leu His Ser Asn Lys Asp Lys Leu His Leu Phe Glu Arg Thr
                    405                 410                 415

Arg Glu Leu Pro Gly Ala Val Ala Ala Ala Ala Ala Ala Ala Thr Thr
                    420                 425                 430

Phe Pro Leu Ala Pro Gln Ile Leu Leu Gly Thr Ile Pro Leu Leu Val
                    435                 440                 445

Leu Leu Pro Val Leu Trp
                450

<210> SEQ ID NO 35
```

<211> LENGTH: 437
<212> TYPE: PRT
<213> ORGANISM: Homo sapiens

<400> SEQUENCE: 35

```
Met Gly Leu Arg Ala Ala Pro Ser Ser Ala Ala Ala Ala Ala Ala Glu
  1               5                  10                  15

Val Glu Gln Arg Arg Pro Gly Leu Cys Pro Pro Leu Glu Leu
             20                  25                  30

Leu Leu Leu Leu Leu Phe Ser Leu Gly Leu Leu His Ala Gly Asp Cys
             35                  40                  45

Gln Gln Pro Ala Gln Cys Arg Ile Gln Lys Cys Thr Thr Asp Phe Val
 50                  55                  60

Ser Leu Thr Ser His Leu Asn Ser Ala Val Asp Gly Phe Asp Ser Glu
 65                  70                  75                  80

Phe Cys Lys Ala Leu Arg Ala Tyr Ala Gly Cys Thr Gln Arg Thr Ser
                 85                  90                  95

Lys Ala Cys Arg Gly Asn Leu Val Tyr His Ser Ala Val Leu Gly Ile
                100                 105                 110

Ser Asp Leu Met Ser Gln Arg Asn Cys Ser Lys Asp Gly Pro Thr Ser
                115                 120                 125

Ser Thr Asn Pro Glu Val Thr His Asp Pro Cys Asn Tyr His Ser His
130                 135                 140

Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
                180                 185                 190

Asn Tyr Leu Ser Val Gln Val Thr Asn Val Pro Val Val Pro Gly Ser
                195                 200                 205

Ser Ala Thr Ala Thr Asn Lys Val Thr Ile Ile Phe Lys Ala His His
                210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
                260                 265                 270

Ala Arg Tyr Ile Gly Thr Thr Val Phe Val Arg Gln Val Gly Arg Tyr
                275                 280                 285

Leu Thr Leu Ala Ile Arg Met Pro Glu Asp Leu Ala Met Ser Tyr Glu
                290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
                340                 345                 350

Thr Ala Asn Thr Gln Cys His Glu Lys Met Pro Val Lys Asp Ile Tyr
                355                 360                 365

Phe Gln Ser Cys Val Phe Asp Leu Leu Thr Thr Gly Asp Ala Asn Phe
                370                 375                 380

Thr Ala Ala Ala His Ser Ala Leu Glu Asp Val Glu Ala Leu His Pro
```

```
                385                 390                 395                 400
Arg Lys Glu Arg Trp His Ile Phe Pro Ser Ser Gly Asn Gly Thr Pro
                        405                 410                 415

Arg Gly Gly Ser Asp Leu Ser Val Ser Leu Gly Leu Thr Cys Leu Ile
                420                 425                 430

Leu Ile Val Phe Leu
            435

<210> SEQ ID NO 36
<211> LENGTH: 436
<212> TYPE: PRT
<213> ORGANISM: Danio rerio

<400> SEQUENCE: 36

Met Gly Met Gly Arg Ala Gly Ser Tyr Tyr Pro Gly Ala Glu Arg Leu
 1               5                  10                  15

Ile Ser Pro Val Leu His Leu Leu Val Leu Cys Thr Leu Ser Ser Leu
                20                  25                  30

Thr Pro Ile Gly Glu Ser Gln Val Gln Thr Pro Gln Cys Arg Ile Gln
            35                  40                  45

Lys Cys Thr Thr Asp Phe Val Ser Leu Thr Ser His Leu Asn Pro Ser
 50                  55                  60

Leu Asp Gly Phe Asp Thr Glu Phe Cys Lys Ala Leu Arg Ala Tyr Ser
65                  70                  75                  80

Ala Cys Thr Gln Arg Thr Ala Lys Ser Cys Arg Gly Asn Leu Val Phe
                85                  90                  95

His Ser Ala Met Leu Gly Ile Thr Asp Leu Met Ser Gln Arg Asn Cys
            100                 105                 110

Ser Lys Asp Gly Pro Thr Ser Thr His Pro Val Ile Pro Ile Glu
        115                 120                 125

Pro Cys Asn Tyr His Ser Arg His His His Val Ser Arg Phe Gly
    130                 135                 140

Thr Gly Val Pro Glu His Pro Arg Leu Met Tyr Leu Phe Cys Gly Leu
145                 150                 155                 160

Phe Gly Asp Pro His Leu Arg Thr Phe Lys Asp Gln Phe Gln Thr Cys
                165                 170                 175

Lys Val Glu Gly Ala Trp Pro Leu Ile Asp Asn Asn Tyr Leu Ser Val
            180                 185                 190

Gln Val Thr Asn Val Pro Val Val Tyr Gly Ser Ser Ala Thr Ala Thr
        195                 200                 205

Asn Lys Ile Thr Ile Ile Phe Lys Pro Tyr Gln Glu Cys Thr Asp Gln
    210                 215                 220

Lys Val Tyr Gln Ala Val Thr Asp Asp Leu Pro Ala Ala Phe Val Asp
225                 230                 235                 240

Gly Thr Ile Ser Gly Gly Asp Ser Glu Thr Arg Ser Ile Trp Ile Leu
                245                 250                 255

Glu Lys Ser Pro Gly Arg His Val Glu Ile His Ala Ala Tyr Ile Gly
            260                 265                 270

Val Thr Ile Ile Ile Arg Gln Gln Gly Arg Tyr Leu Thr Leu Ala Val
        275                 280                 285

Arg Met Pro Glu Glu Leu Ala Met Ala Phe Asp Glu Thr Gln Asp Leu
    290                 295                 300

Gln Leu Cys Met Asn Gly Cys Pro Thr Ser Glu Arg Ile Asp Gln Glu
305                 310                 315                 320
```

-continued

```
Gly His Leu Gln Leu Pro Val Leu Gly Leu Gln Ala Gly Phe Gln
            325                 330             335

Gln Gln Gln Gln Pro Arg Val Glu Ala Gln Arg Gly Val Pro Thr Leu
            340                 345             350

Glu Ser Ala Ser Arg Arg Cys Arg Asp Gln Leu Glu Val Lys Asp Ile
            355                 360             365

Tyr Phe His Ser Cys Val Phe Asp Leu Leu Thr Thr Gly Asp Ala Asn
    370                 375                 380

Phe Thr Thr Ala Ala Tyr Asn Ala Leu Lys Asp Met Glu Thr Leu His
385                 390                 395                 400

Pro Lys Lys Glu Arg Trp Gln Ile Phe Pro Asn Ser Ala Ser Arg Leu
            405                 410                 415

Ser Pro Phe Ser Leu Leu Leu Thr Ala Leu Leu Ser Ser Phe Leu Ile
            420                 425                 430

Ala Val Leu Leu
        435
```

DRG11-RESPONSIVE (DRAGON) POLYPEPTIDES

This application is a continuation of U.S. patent application Ser. No. 13/281,510, filed Oct. 26, 2011, which is a continuation of U.S. patent application Ser. No. 12/509,951, filed Jul. 27, 2009, which is a divisional of U.S. application Ser. No. 11/230,180, filed Sep. 19, 2005, which is a divisional of U.S. patent application Ser. No. 10/419,296, filed Apr. 17, 2003, issued as U.S. Pat. No. 7,319,138, on Jan. 15, 2008, which claims benefit from U.S. Provisional Application No. 60/373,519, filed Apr. 18, 2002, the entire contents of which are hereby incorporated by reference.

FIELD OF THE INVENTION

This invention relates to a DRG11-responsive gene and its homologs useful for treating and diagnosing diseases, developmental defects, and injuries of the nervous system, retina, skin, muscle, bone, and joint tissue.

BACKGROUND OF THE INVENTION

Developmentally regulated transcription factors drive developmental gene programs that result in embryo formation and the birth, proliferation, growth, migration, and differentiation of the cells that eventually make up the different tissues of the body. This involves the expression and repression of many genes including those whose protein products act as regulators of this process as signal molecules. When the signal proteins are secreted, they may act both as paracrine signals between different cells, including on stem cells, and as autocrine signals on the same cells that produce the signal molecule. When the protein is not secreted, but rather inserted into the cell membrane, it may contribute to cell-cell interactions.

In the case of the developing nervous system, multiple secreted and non-secreted signal molecules expressed at different times and in different spatial locations are involved in: (i) determining the induction of the neural plate; (ii) regionalization of the neural tube along dorsoventral and anteroposterior axes; (iii) generation of neurons and glia from multipotent precursors (neuronal determination); (iv) determination of survival or apoptotic cell death; (v) migration of neurons; (vi) differentiation and regional patterning of neurons; (vii) neurite outgrowth and axon guidance; (viii) formation of specific synaptic connections between neurons, and (ix) determining neuronal-glial interactions.

Some of these signal molecules may be re-expressed in the adult after injury, or the failure of such re-expression may relate to the failure of mature neurons to survive, grow, or regenerate after injury. Some of the signal molecules may act in pathological situations to either promote or suppress abnormal growth or function. These signal molecules, acting on specific transmembrane receptors, may serve as neuronal determinants, survival factors, growth factors, guidance cues, or differentiation factors, and many may have potential therapeutic roles as biological agents beyond their specific involvement in development. Such factors can have biological activity both in vivo and for maintaining cultured cells in vitro, or for converting pluripotent stem cells into specific neuronal or non-neuronal subtypes. Similarly, mimicking the action of these signal molecules by activating their membrane bound receptors or the intracellular signal transduction pathways coupled to their receptors, may also have therapeutic potential.

SUMMARY OF THE INVENTION

We have discovered a novel gene family, designated "Dragon" (DRG11-Responsive Axonal Guidance and Outgrowth of Neurite), expressed in the nervous system, retina, skin, muscle, bone, and joint tissue. Three homologous proteins have been identified in each of the mouse, zebrafish, and human. A partial sequence of an ortholog has also been identified in C. elegans.

The invention features substantially pure DRAGON, Dragon-like 1 (DL-1), and Dragon-like 2 (DL-2) proteins, fragments, homologs, and orthologs, as well as non-naturally occurring but substantially identical proteins. Preferably, the proteins are mammalian and/or are substantially identical to murine DRAGON, Dragon-like 1 (mDL-1), or Dragon-like 2 (mDL-2) (SEQ ID NO: 5-7, respectively), or human DRAGON, Dragon-like 1 (hDL-1), or Dragon-like 2 (hDL-2) (SEQ ID NO: 8-10, respectively). Also included in this invention are the zebrafish homologs of DRAGON, DL-1, and DL2 (SEQ ID NO: 28-30, respectively) and the C. elegans homolog containing the polypeptide sequence of SEQ ID NO: 18.

Also featured are substantially pure nucleic acids which encode DRAGON and the Dragon-like proteins, for example, from mammals. Preferably, the nucleic acids are substantially identical to the murine DRAGON, DL-1, or DL2 (SEQ ID NO: 1-3, respectively), human DRAGON, DL-1, or DL-2 (SEQ ID NO: 4, 31, and 32, respectively), or zebrafish DRAGON, DL-1, or DL-2 (SEQ ID NO: 25-27, respectively). Other embodiments include nucleic acids which, but for the degeneracy of the genetic code, would be substantially identical to the identified murine, human, and zebrafish Dragon family members, as well as nucleic acids which hybridize under high stringency or, less preferably, low stringency conditions to any of those nucleic acids.

Monoclonal and polyclonal antibodies that selectively bind the Dragon family proteins, for example, of SEQ ID NO: 5-10, 18, or 28-30, can also be prepared and are included in the invention. Preferably, the antibodies specific for murine DRAGON bind a protein sequence encoded by residues 38-56, 261-278, or 369-386 of SEQ ID NO: 5, and the antibodies specific for hDRAGON bind a protein sequence encoded by residues 54-72, 277-294, or 385-408 of SEQ ID NO: 8. Other immunogenic portions of the proteins of the Dragon family also can be used for antibody production.

Also provided are expression vectors containing a coding sequence operably linked to an expression control element, such as a promoter or enhancer element. Preferred coding sequences include those that encode any Dragon family protein or fragment thereof, or express an antisense nucleic acid which is complementary to and capable of hybridizing to a nucleic acid that encodes a member of the Dragon family, or its promoter. Preferably, these antisense nucleic acids include at least 12 and more preferably at least 25 contiguous nucleotides. These vectors can be used to transfect cells, resulting in the production of Dragon family proteins and/or sense or antisense nucleic acids. Suitable cells include, for example, bacteria, yeast, and mammalian, for example, human cells. Transfection may result in stable or transient Dragon expression.

Transgenic non-human organisms with altered Dragon expression levels are also included in the invention. A transgenic organism of this invention can either have a homologous Dragon-coding sequence (for example, a human DRAGON-coding sequence) inserted into its genome such that Dragon expression is increased, or the endogenous Dragon gene(s) can be disrupted rendering the organism Dragon-deficient. Any non-human organism can be used for transgenic Dragon expression or can be rendered Dragon-deficient. Preferably, the transgenic or Dragon-deficient organisms are *C. elegans* or mammals, such as mice.

The invention also provides a method for treating a patient with a neurological disorder, a developmental deficit, or a congenital disorder of the nervous system by administering a therapeutically effective amount of a Dragon family protein. Preferably, the Dragon protein is a mammalian protein, for example, hDRAGON or hDL-2. Neurological disorders that can be treated according to the methods of this invention include neurodegenerative diseases such as Parkinson's disease, Huntington's disease, Alzheimer's disease, motor neuron diseases and other spinal muscular atrophies, and neuropathies including diabetic neuropathy and inherited demyelinating neuropathies. Other nervous system injuries or functional disorders that can be treated, for example, by DRAGON or DL-2, include those caused by trauma, (e.g., peripheral nerve, dorsal root, spinal cord, and brain injury) cerebrovascular disease (e.g., ischemia, thrombosis, or hemorrhage), chemical-induced neurotoxicity, metabolic diseases, infection, primary and secondary neoplasms of the nervous system, congenital abnormalities of nervous system (e.g., neurofibromatosis, phakomatosis, cerebral palsy, mental retardation), sensory and motor-abnormalities, (e.g., pain, nociceptive inflammatory, peripheral and central neuropathic pain), cognitive and mood disorders, psychoses, epilepsy, coordination disorders. Nervous system disorders caused by non-neuronal cells are also amenable to treatment using mammalian DRAGON or DL-2. Disorders of this type include, for example, demyelinating disorders, axonal conduction deficits, and abnormal growth of glial cells (e.g., gliomas, Schwanomas, and neurofibromatosis), degenerative diseases of the retina, cochlea and olfactory mucosa. Treatment may be by any method and is preferably by oral, parenteral, intrathecal, or intracerebrovascular administration.

DRAGON may also be used to treat disorders of the skin. Preferably, the DRAGON protein is mammalian, most preferably human. Administration of a DRAGON protein will preferably be topical in a cream, gel, ointment, or irrigation solution. Alternatively, the DRAGON protein can be administered by subcutaneous injection at or near the lesion site. Disorders amenable to treatment include trauma (i.e., accidental or surgical), burns (i.e., chemical, thermal, or radiation), allergic reactions such as eczema, psoriasis, or contact dermatitis, pressure ulcers, and acne.

The DRAGON protein may also be used to treat disorders of the retina and optic nerve. Administration of a DRAGON protein, preferably a mammalian (i.e., human) protein, may be in the form of eye drops or an irrigation solution. Alternatively, intraocular or intraorbital injection may be used. Retinal disorders amenable to treatment using a DRAGON protein include, for example, traumatic injuries (i.e., detached retina), macular degeneration, and sarcoidosis. Optic nerve diseases amenable to treatment with a DRAGON protein include, for example, ischemic optic neuropathy, primary glaucomatous optic nerve disease (GOND), toxic optic nerve disease, and Leber's Hereditary Optic Neuropathy (LHON).

Dragon-like 1 (DL-1) can be used for treatment of disease conditions of the bone, muscle, joint, or cartilage including muscle wasting, congenital myopathies, muscular dystrophy, and the innervation of muscle by motor axons (e.g., following peripheral nerve injury), bone fracture, metabolic disorders of bone, disorders of bone formation or resorption, neoplasms of bone, congenital abnormalities of bone (bone dyplasias, achondorplasia, or endochondromatosis), inflammatory or degenerative joint diseases (e.g. arthritis, osteoarthritis, and rheumatoid arthritis), muscle paralysis and other diseases resulting in the failure of the neuromuscular system (e.g., myasthenia gravis).

DL-2 can also be used for treatment of cardiovascular diseases and disorders including, for example, developmental heart abnormalities, congenital cardiac malformations, and blood vessel malformations (e.g., aneurisms).

Embryonic or adult pluripotent cells can be induced to differentiate into neuronal, retinal, epidermal (DRAGON or DL-2), or myogenic (DL-1) phenotypes by contacting the cells with a Dragon protein in a manner sufficient to increase the Dragon biological activity. The Dragon protein that contacts the cells to induce a particular phenotype may result from the overexpressing a Dragon nucleic acid by the cells or the cells can be cultured in the presence of an exogenously applied Dragon protein. Preferably, the cells are human embryonic stem cells or bone marrow-derived stem cells. Optionally, a TGF-$\beta$ family member or TGF-$\beta$ receptor can be inhibited to aid in inducing a neuronal phenotype. Cells that have been induced or regulated by DRAGON or DL-2 treatment may be used for subsequent administration to patients to replace lost or abnormally functioning cells.

The invention also provides a method for diagnosing a Dragon-related condition in a patient. Typically, the condition is diagnosed by assessing a Dragon family nucleic acid (e.g., gene) for one or more mutations that reduce Dragon biological activity. The Dragon family nucleic acid may be, for example, DRAGON, DL-1, or DL-2. These mutations may be in an untranslated region such that gene expression is impaired. Alternatively, the mutation may be in a coding region, causing a reduction in protein function. Common techniques for assessing Dragon nucleic acids include, for example, Northern and Southern analysis, including the polymerase chain reaction (PCR), and restriction fragment length polymorphism (RFLP) analysis. Any appropriate patient sample can be used in the diagnostic screening provided; however, particularly useful sample sources include, for example, blood samples and tissue biopsies.

The Dragon family proteins and nucleic acids can also be used to identify candidate compounds which modulate (increase or decrease) Dragon expression, or mimic or inhibit Dragon biological activity. Compounds identified using these screening techniques are useful for treating Dragon-related diseases and conditions described herein. A method for identifying candidate compounds that modulate Dragon activity includes the steps of: (a) exposing a sample to a test compound, wherein the sample contains a Dragon nucleic acid, a Dragon promoter operably linked to a reporter gene (for example, a detectable label such as alkaline phosphatase), or a Dragon protein; and (b) identifying a useful candidate compound by assaying for a change in the level of Dragon expression or biological activity in the sample, relative to a sample not exposed to the test compound.

The invention also features a method for identifying endogenous and synthetic Dragon family binding partners such as Dragon receptors and Dragon ligands. The method includes the steps of: (i) providing a Dragon fusion protein which consists of a Dragon protein linked to a tag molecule; (ii) contacting a sample containing a putative Dragon binding partner with a Dragon fusion protein under conditions which allow for a Dragon-Dragon binding partner complex to form, (iii) detecting the Dragon fusion protein by detecting the tag molecule, and (iv) interpreting the Dragon fusion protein detection to determine whether the Dragon fusion protein is complexed to a Dragon binding partner from the sample. In one embodiment, a further step of (v) isolating the Dragon- Dragon binding partner complex using a method directed against the tag molecule. In one preferred embodiment, the step (iii) detecting is done using a detectably labeled antibody. Preferred techniques in step (iii) include, for example, Western blotting and ELISA assays. In another preferred embodiment, the step (v) isolating is done using affinity chromatography.

By "Dragon protein" or "Dragon-family protein" is meant any polypeptide that is substantially identical to the human, murine, or zebrafish DRAGON, Dragon-like 1 (DL-1), or Dragon-like 2 (DL-2) proteins. Dragon proteins also include substantially identical fragments of DRAGON, DL-1, DL-2, or any other Dragon-family protein. Dragon fragments are typically at least 50, 100, 150, 200, 250, 300, 350, or 400 amino acids in length.

By "Dragon nucleic acid" or "Dragon-family nucleic acid" is meant any polynucleotide that is substantially identical to the human or murine DRAGON, DL-1, or DL-2 cDNA sequences, any polynucleotide having a degenerate sequence that encodes a DRAGON, DL-1, or DL-2 protein, or any polynucleotide whose complement hybridizes to a human or murine DRAGON, DL-1, or DL-2 sequence under high stringency conditions. Alternatively, a Dragon nucleic acid encodes a protein which is substantially identical to the human or murine DRAGON, DL-1, or DL-2 proteins.

By "DRAGON protein" is meant a polypeptide having a sequence substantially identical to SEQ ID NO: 5, 8, 18, or 28.

By "DL-1 protein" is meant a polypeptide having a sequence substantially identical to either SEQ ID NO: 6, 9, or 29.

By "DL-2 protein" is meant a polypeptide having a sequence substantially identical to either SEQ ID NO: 7, 10, or 30.

By "DRAGON nucleic acid" is meant a polynucleotide having a sequence which encodes a DRAGON protein. Preferably, a DRAGON nucleic acid is substantially identical or hybridizes under high stringency conditions to SEQ ID NO: 1, 4, or 25.

By "DL-1 nucleic acid" is meant a polynucleotide having a sequence which encodes a DL-1 protein. Preferably, a DL-1 nucleic acid is substantially identical or hybridizes under high stringency conditions to SEQ ID NO: 2, 26, or 31.

By "DL-2 nucleic acid" is meant a polynucleotide having a sequence which encodes a DL-2 protein. Preferably, a DL-2 nucleic acid is substantially identical or hybridizes under high stringency conditions to SEQ ID NO: 3, 27, or 32.

By "substantially identical" is meant a polypeptide or nucleic acid exhibiting at least 50%, 75%, 85%, 90%, 95%, or even 99% identity to a reference amino acid or nucleic acid sequence. For polypeptides, the length of comparison sequences will generally be at least 20 amino acids, preferably at least 30 amino acids, more preferably at least 40 amino acids, and most preferably 50 amino acids, or full-length. For nucleic acids, the length of comparison sequences will generally be at least 60 nucleotides, preferably at least 90 nucleotides, and more preferably at least 120 nucleotides, or full length.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, e.g., Ausubel et al., *Current Protocols in Molecular Biology*, John Wiley & Sons, New York, N.Y., 2000, hereby incorporated by reference.

By "Dragon antisense nucleic acid" is meant a nucleic acid complementary to a Dragon coding, regulatory, or promoter sequence, including human and murine DRAGON, Dragon-like 1 (DL-1) and Dragon-like 2 (DL-2). Preferably, the antisense nucleic acid decreases expression (e.g., transcription and/or translation) of the Dragon by at least 5%, 10%, 25%, 50%, 75%, 90%, 95%, or even 99%. Preferably, the Dragon antisense nucleic acid comprises from about 8 to 30 nucleotides. A Dragon antisense nucleic acid may also contain at least 40, 60, 85, 120, or more consecutive nucleotides that are complementary to a Dragon mRNA or DNA, and may be as long as a full-length Dragon gene or mRNA. The antisense nucleic acid may contain a modified backbone, for example, phosphorothioate, phosphorodithioate, or other modified backbones known in the art, or may contain non-natural internucleoside linkages.

A Dragon antisense nucleic acid may also be encoded by a vector where the vector is capable of directing expression of the antisense nucleic acid. This vector may be inserted into a cell using methods known to those skilled in the art. For example, a full length Dragon nucleic acid sequence, or portions thereof, can be cloned into a retroviral vector and driven from its endogenous promoter or from the retroviral long terminal repeat or from a promoter specific for the target cell type of interest. Other viral vectors which can be used include adenovirus, adeno-associated virus, vaccinia virus, bovine papilloma virus, or a herpes virus, such as Epstein-Barr Virus.

By "vector" is meant a DNA molecule, usually derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

By "substantially pure" is meant a nucleic acid, polypeptide, or other molecule that has been separated from the components that naturally accompany it. Typically, the polypeptide is substantially pure when it is at least 60%, 70%, 80%, 90% 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "promoter" is meant a nucleic acid sequence sufficient to direct transcription of a gene. Also included in the invention are those promoter elements which are sufficient to render promoter-dependent gene expression controllable for cell type-specific, tissue-specific or inducible by external signals or agents (e.g. enhancers or repressors); such elements may be located in the 5' or 3' regions of the native gene, or within an intron.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences.

By "signal sequence" is meant a nucleic acid sequence which, when operably linked to a nucleic acid molecule, facilitates secretion of the product of the nucleic acid molecule. The signal sequence is preferably located 5' to the nucleic acid molecule.

By "transgene" is meant any piece of nucleic acid that is inserted by artifice into a cell, or an ancestor thereof, and becomes part of the genome of the animal which develops from that cell. Such a transgene may include a gene which is partly or entirely heterologous to the transgenic animal, or may represent a gene homologous to an endogenous gene of the animal.

By "transgenic" is meant any cell which includes a nucleic acid sequence that has been inserted by artifice into a cell, or an ancestor thereof, and becomes part of the genome of the organism which develops from that cell. Preferably, the transgenic organisms are transgenic mammals (e.g., rodents or ruminants), or C. elegans, Zebra fish, or Drosophila. Preferably the nucleic acid (transgene) is inserted by artifice into the nuclear genome.

By "antibody that selectively binds" is meant an antibody capable of a high affinity interaction with a specific target molecule, having a dissociation constant of <1 μM, <100 nM, <10 nM, <1 nM, or even <100 pM. Preferably, the antibody has at least 10-fold, 100-fold, 1,000-fold, or even 10,000-fold lower affinity for other, non-target molecules.

By a "neurological disorder" is meant any disease or condition that causes injury to any component of the peripheral or central nervous system, including the retina. Neurological disorders include acute and chronic conditions. Acute conditions include, for example, trauma, stroke, and chemical-induced neurotoxicity. Chronic conditions include, for example, neurodegenerative diseases and cancers of the nervous system including gliomas, schwanomas, and astrocytomas. Neurological disorders can also arise from developmental defects, including inherited or congenital defects (e.g. cerebral palsy), and autoimmune diseases (e.g., multiple sclerosis). Neurological disorders also include functional disorders such as paralysis, and epilepsy, as well as sensory, mood, and psychomotor disorders (e.g., fibromyalgia, dysthesia).

By a "neurodegenerative disease" is meant any disease of the central, peripheral, or autonomic nervous system that is characterized by progressive neuronal loss or dysfunction, including but not limited to Alzheimer's Disease, dementia pugilistica, Parkinson's Disease, Huntington's Disease, Niemann-Pick disease, multiple sclerosis, neuropathies (e.g., central, peripheral, compression type, and diabetic) and ischemic conditions such as stroke and cerebral artery infarction. Defects in myelin repair are also considered neurological diseases. The defects may arise during the process of demyelination, the removal of myelin debris following injury, or the remyelination process.

By a "bone disorder" is meant any condition of the bone which is characterized by altered bone remodeling. Bone disorders include physical traumas such as bone fractures, metabolic bone diseases such as Paget's disease and hyperostosis, and bone neoplasms (e.g., oesteochondromas, oesteogenic sarcoma).

By a "joint disorder" is meant any trauma or disease process which causes inflammation in or around the cartilage or joint capsule. Joint disorders include, for example, inflammatory arthritis, rheumatoid arthritis, and osteoarthritis.

By a "muscle disorder" is meant any dysfunction of muscle tissue regardless of cause. Muscle disorder may arise for congenital abnoimalities, trauma, metabolic disease, or autoimmune disease. Muscle disorders include, for example, muscular dystrophy, myasthenia gravis, transient and periodic muscle paralysis, muscle wasting diseases, muscular dystrophy, myotonia congenital, myotonic dystrophy, and loss of innervation of motor endplates.

By a "Dragon-related condition" is meant any disease or disorder which is associated with the dysfunction or altered (increased or decreased) activity or expression of any one or more of the Dragon protein family. Alternatively, Dragon-related conditions can also refer to any disease or disorder which, although not associated with Dragon dysfunction, is amenable to treatment by modulating (increasing or decreasing) the activity or expression of any one or more Dragon proteins or nucleic acids or by mimicking their actions. Dragon-related conditions include, for example, neurological, retinal, and skin disorders, neurodegenerative diseases, and muscle, bone, or joint disorders.

By a "therapeutically effective amount" is meant a quantity of compound (e.g., a Dragon family protein) delivered with sufficient frequency to provide a medical benefit to the patient. Thus, a therapeutically effective amount of a Dragon family protein is an amount sufficient to treat or ameliorate a Dragon-related condition or symptoms.

By "treating" is meant administering a pharmaceutical composition for the purpose of improving the condition of a patient by reducing, alleviating, or reversing at least one adverse effect or symptom.

BRIEF DESCRIPTION OF DRAWINGS

FIG. 1B is the nucleic acid (SEQ ID NO: 1) and deduced polypeptide sequence of murine DRAGON (mDRAGON; SEQ ID NO: 5). The DRAGON protein contains an N-terminal signal peptide and a C-terminal glycophosphatidyl inositol (GPI) anchor.

FIG. 2 is a graph illustrating the result of a computational structure-function analysis of niDRAGON (SEQ ID NO: 5), demonstrating the presence of a signal sequence which results in protein secretion.

FIG. 3 is a sequence alignment of hDRAGON (SEQ ID NO: 8) and a portion of the insulin-like growth factor binding protein 2 (IGFBP2; SEQ ID NO: 12).

FIG. 4 is a sequence alignment of hDRAGON (SEQ ID NO: 8) and a portion of the ephrin type-B receptor 3 precursor (EPHB3; SEQ ID NO: 13).

FIG. 5 is a sequence alignment showing domain homology between mDRAGON (SEQ ID NO: 5) and portions of human Notch 3 (SEQ ID NO: 14) and murine phosphatidylinoitol-4-kinase type II beta (SEQ ID NO: 15).

FIG. 6 is a sequence alignment showing the domain homology between mDRAGON (SEQ ID NO: 5) and a portion of thrombospondin-1 (SEQ ID NO: 16; THR-1) and Slit2 (SEQ ID NO: 17).

FIG. 8A is an amino acid sequence alignment of mDRAGON (SEQ ID NO: 5), mDL-2 (SEQ ID NO: 7), and mDL-1 (SEQ ID NO: 6). FIG. 8B is an amino acid sequence alignment of mDRAGON (SEQ ID NO: 5), hDRAGON (SEQ ID NO: 8), and zDRAGON (SEQ ID NO: 26).

FIG. 9A-9C demonstrate that DRAGON and DL-2, but not DL-1, mRNA is expressed in mouse embryonic E14.5 spinal cord. DRAGON is the only family member expressed in the DRG. FIGS. 9D-9F are transverse sections of whole mouse E17.5 embryo demonstrating DRAGON, DL-1, and DL-2 mRNA expression. FIGS. 9G-9I demonstrate DRAGON mRNA expression in transverse sections of mouse E17.5 embryo head. (FIG. 9G: Mes.: mesencephalic vesicle; E.: ependymal layer; M.: mantle layer. FIG. 9H: M.: myelencephalon; D: diencephalon; S: striatum; C: cortex. FIG. 9I: D: DRG; S.C.: spinal cord; C.: cochlea; R.: retina; Olf.: future olfactory lobe) FIGS. 9J-9L demonstrate DL-2 mRNA expression in transverse section of mouse E17.5 embryo head.

FIG. 10 is a series of photomicrographs showing the distribution of DRAGON mRNA in the adult rat DRG by in situ hybridization.

FIG. 13A is a Western blot analysis of protein extract from untransfected HEK293 cells (−), or those transfected (+) with DRAGON expression vector. A distinct band having a molecular weight of about 50 KDa is recognized by the anti-DRAGON antibody in transfected, but not control, cells. ERK protein level was used as a loading control. FIG. 13B is a photomicrograph of an immunocytochemical study showing significant staining of DRAGON-expressing HEK cells (top). Pretreatment of DRAGON-expressing HEK cells with PI-PLC causes a significant reduction of anti-DRAGON staining (bottom). Non-transfected HEK cells show no anti-DRAGON staining (not shown). FIG. 13C is a photomicrograph of a Western blot analysis of samples of DRAGON-expressing HEK cell culture medium, with or without pretreatment using PI-PLC. A band corresponding to DRAGON is detected in PI-PLC treated medium samples. FIG. 13D is a series of photomicrographs from an anti-DRAGON immunohistochemical study of adult spinal cord and DRG at low (top) and high (middle) magnification. As a control, the anti-DRAGON antibody was pretreated with the immunogenic DRAGON fragment prior to immunohistochemical staining (bottom). Scale, 100 μM.

FIG. 16A is a Northern blot showing the developmental expression of DRAGON in Zebrafish embryos over the first 36 hours post fertilization (hpf). FIGS. 16B-16C are lateral views of an 18-20 somite stage zebrafish embryo following in situ hybridization using a DRAGON antisense probe (FIG. 16B) or the sense control (FIG. 16C). DRAGON expression is strongest at the anterior pole and in the tail-bud region (arrows). More diffuse and lower levels of expression are seen in other parts of the brain. FIG. 16D is a dorsal view of a flat-mounted embryo showing DRAGON staining in the CNS. DRAGON expression is particularly strong in the region surrounding the olfactory placodes (black arrow) and in the retina (white arrow). FIGS. 16E-16G are photomicrographs demonstrating that DRAGON overexpression causes abnormalities in brain morphology and, at a lower frequency (7-15%), cylopia. FIG. 16H is a Northern blot of zebrafish embryo RNA demonstrating that a morpholino oligonucleotide (MO) targeted against the splice donor site of DRAGON exon1 blocks RNA splicing and protein expression. An inverted morpholino oligonucleotide (cont. MO), which preserves the base composition, was used as the control. Primers flanking the intron used for RT-PCR produce the predicted bands from the end products of splicing in the control but not the experimental morpholinos. FIGS. 16I-16J are photomicrographs of 24 hour zebrafish embryos following MO injection. Morphologically, the eyes are affected and extensive cell death in the brain obscures the clear definition of the midbrain-hindbrain boundary. FIGS. 16K-16M show TUNEL staining of MO injected embryos at the 21 somite stage revealing a pattern of cell death correlating with the pattern of DRAGON expression.

FIG. 17 is a sequence alignment of mDRAGON (SEQ ID NO: 5) and a region of *C. elegans* DRAGON. The full length *C. elegans* DRAGON is also provided (SEQ ID NO: 18).

DETAILED DESCRIPTION

DRG11 is a paired homeodomain transcription factor that is expressed both by dorsal root ganglion (DRG) sensory neurons and by dorsal horn neurons early in development (Saito et al., Mol. Cell. Neurosci. 6:280-92, 1995). Its absence, following a null mutation of its gene, leads to abnormalities in the spatio-temporal distribution of sensory neuron projections to the dorsal horn, as well as defects in dorsal horn morphogenesis (Chen et al., Neuron 31:59-73, 2001). These developmental abnormalities may account for a significantly attenuated sensitivity to noxious stimuli in the DRG11 deficient mice (Chen et al., supra).

DRG11 Responsive Gene Identification

Figure 1A:
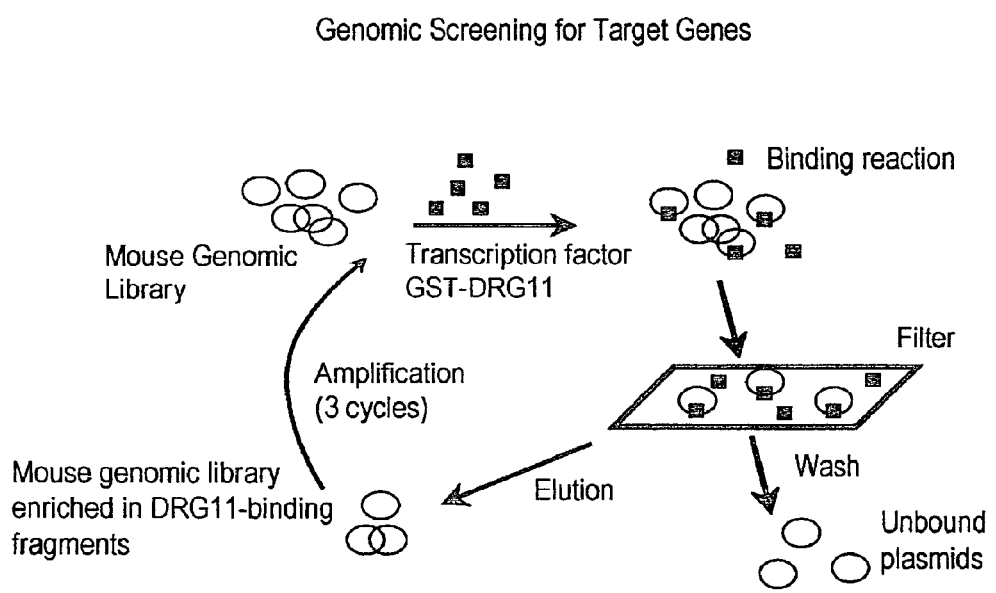
FIG. 1A is a schematic diagram illustrating a strategy for genomic screening with a CpG island library. The plasmid DNA was bound with GST-DRG11-DBD and passed through a nitrocellulose filter. DRG11-bound plasmids were eluted and amplified in bacterial cultures. The DRG11-bound plasmids were concentrated by repeating the cycle a total of five times.

A Genomic Binding Site (GBS) strategy was used in a mouse CpG island library to isolate genes responsive to the transcription factor DRG11 and to identify proteins that are involved in the development of sensory pathways (primary sensory neurons and spinal cord neurons) and other neurons (FIG. 1A). The general strategy isolates DRG11-binding fragments from mouse genomic DNA using a fusion protein (DRG-GST) consisting of a recombinant DRG11 DNA binding domain (amino acids 31-90 of mDRG-11) and GST. DRG11-responsive genes are located and isolated from the genomic region adjacent to the DRG-11 binding site. Mouse CpG islands are selected by the methyl-CpG binding domain of MeCP2, which binds DNA methylated at CpG and allows fractionation of DNA according to its degree of CpG methylation. The CpG library consists of short stretches of DNA containing a high density of nonmethylated CpG dinucleotides. About 60% of human genes are associated with CpG islands. These regions often include the promoter region and one or more exons of associated genes, allowing the isolation of full length eDNAs and genomic mapping.

The GBS cloning using the CpG island library was performed according to the method of Watanabe et al. (Mol. Cell. Biol. 18:442-449, 1998). Briefly, ten micrograms of the mouse library plasmid DNA was incubated with the DRG-GST fusion protein. The resulting solution was then passed slowly through a presoaked nitrocellulose filter and washed. The trapped plasmid DNA was eluted from the filter and transformed into DH5α (E. coli) competent cells. The cells were cultured in Luria broth-ampicillin (LB) medium and plasmid DNA was prepared. The cycle was repeated for a total of three times. After the third cycle, the plasmid DNA library, enriched in genomic fragments that bind to the DRG11 DNA binding domain, was plated on LB-ampicillin agar plates, and individual clones were amplified, sequenced, and characterized.

Identification and Characterization of Murine DRAGON

Among the most abundant clones obtained, was a 363 base pair (bp) DNA fragment located 750 bp upstream of an open reading frame of a novel gene. Sequence analysis studies indicated that the genomic fragment is located in the promoter region of the new gene. Genomic database analysis, combined with RT-PCR and RACE (Rapid Amplification of cDNA Ends) of mouse DRG and spinal cord cDNA libraries found that the open reading frame encoded a novel cDNA (SEQ ID NO: 1) that we have called DRAGON. The nucleotide and predicted 436 amino acid sequence of DRAGON (SEQ ID NO: 5) are shown in (FIG. 1B).

Sequence analysis of the mDRAGON coding region identified conserved domains with homology to notch-3 (FIG. 5), phosphatidylinositol-4-phosphate-5-kinase type II beta (FIG. 5), insulin-like growth factor binding protein-2 (IGFBP2; FIG. 3), thrombospondin (FIG. 6), ephrin type-B receptor 3 precursor (EPHB3; FIG. 4), and Slit-2 (FIG. 6), all of which are known to influence axonal guidance, neurite outgrowth, and other neuronal developmental functions. The C-terminus of mDRAGON is also predicted to contain a hydrophobic domain indicative of a 21 amino acid extracellular GPI anchoring. A computational structure-function analysis of mDRAGON reveals the presence of a putative signal peptide sequence (FIG. 2), indicating that the gene product is a secreted protein, and further supporting an extracellular localization.

Identification of DRAGON Homologs

Sequence homology analysis using a mouse genome database identified two murine genes homologous to DRAGON. The cDNA sequences of these homologs (mDL-1 and mDL-2) are provided in SEQ ID NO: 2 and SEQ ID NO: 3, respectively. The deduced polypeptide sequences are also provided (SEQ ID NO: 6 and 7). Sequence alignments indicating areas of homology between mDRAGON, mDL-1, and mDL-2 are shown in FIG. 8A. The GPI anchor sequence is predicated to be at the C-terminal 27 and 36 amino acids of mDL-1 and mDL-2, respectively.

DRG11 Induces DRAGON Expression

Following the initial identification of mDRAGON using GBS cloning, the mDRAGON promoter (363 bp fragment) was confirmed to be DRG11-responsive using the reporter gene assay generally described by Ogura et al. (Proc. Natl. Acad. Sci. USA, 92:392-396, 1995). The 363 bp fragment was subcloned into the PGL3-Promoter reporter vector containing an SV40 promoter upstream of the luciferase gene. DRG11 triggered a 6-fold increase in luciferase activity as compared to control (FIG. 7B), revealing the presence of one or several DRG11 response elements in the 363 base pair promoter fragment. No induction in luciferase activity was detected in the absence of DRG11, indicating that the enhancer activity of the DRAGON promoter fragment was DRG11 dependent.

Tissue Localization of Dragon Gene Expression

Figure 7A:
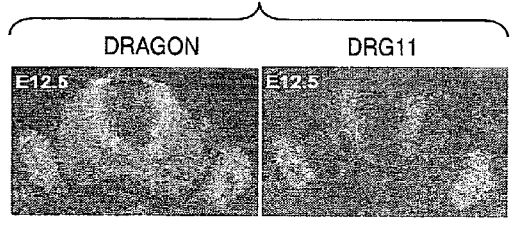
FIG. 7A is a photomicrograph of an in situ hybridization study showing that DRAGON and DRG11 mRNAs are both expressed in the dorsal root ganglion (DRG) and the spinal cord at E12.5.
Figure 7B:
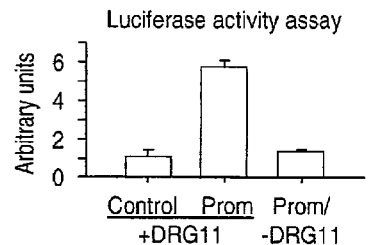
FIG. 7B is a bar graph showing the DRG11-dependent enhancer activity of the DRAGON promoter fragment.
Figure 7C:
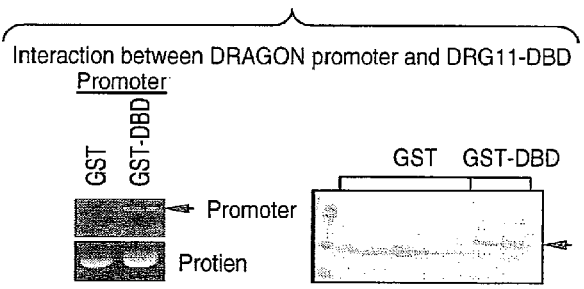
FIG. 7C shows the results of a pull-down experiment using either GST or GST-DBD (DBD=DRG11 DNA Binding Domain). The purified proteins (right panel) were incubated with the DRAGON promoter fragment, and "pulled down" using glutathione sepharose. Only GST-DBD fusion protein pulled down the promoter fragment as assessed by agarose gel electrophoresis.
Figure 7D:
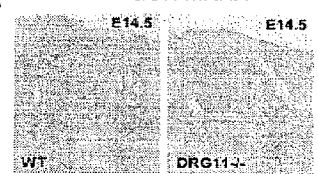
FIG. 7D is a photomicrograph of an in situ hybridization study demonstrating a decrease in DRAGON mRNA expression in the DRG and the spinal cord of DRG11−/− mouse at E14.5, compared to wildtype.
Figure 7E:
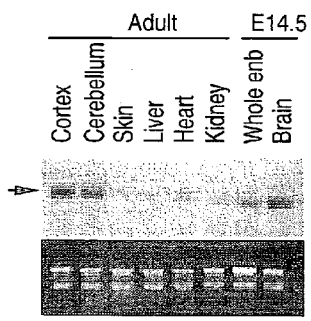
FIG. 7E shows the result of a Northern blot analysis of DRAGON mRNA expression in adult and embryonic E14.5 tissue.

In situ hybridization was used to demonstrate that at E12.5 DRG11 and DRAGON expression overlaps (FIG. 7A). In the DRG most neurons express both DRG11 and DRAGON; in the spinal cord DRG11 and DRAGON are expressed in the same medial region adjacent to the ventricular zone (FIG. 7A). A pull down assay was carried out to confirm interaction of DRG11 with the 363 bp promoter fragment of DRAGON obtained with the GBS screening. The promoter fragment was pulled down by a GST-DRG11-DBD fusion protein but not GST (FIG. 7C). Finally, DRAGON mRNA expression in DRG11 null mutant embryonic mice was examined. DRAGON expression in the spinal cord and DRG were significantly reduced in DRG11−/− mice compared to wildtype littermates (FIG. 7D).

Figure 7F:
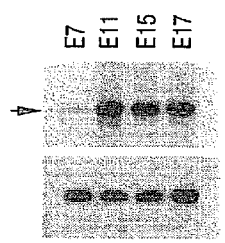
FIG. 7F shows the result of a Northern blot analysis of DRAGON mRNA expression in whole mouse embryos during development. β-actin mRNA levels were used as a loading control.

DRAGON mRNA is expressed in embryonic and adult mouse DRGs, spinal cord and brain, with little or no expression in the liver and kidney, and low levels in the heart (FIGS. 7E, 9A, 9D, 9G, 9J, and 10). DRAGON expression begins early in development (at least E7) (FIG. 7F), much earlier than DRG11 (E12). Its expression is dynamically regulated in the PNS and CNS during development.

Figure 11:
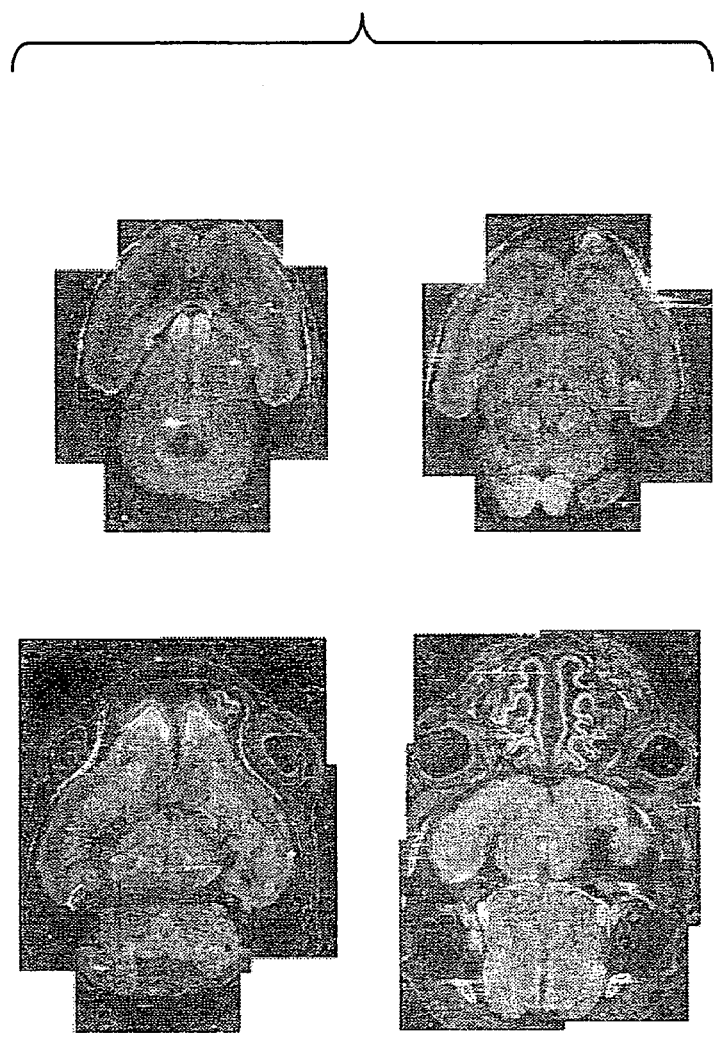
FIG. 11 is a series of photomicrographs showing the distribution of DRAGON mRNA in the brain of an E18 mouse by in situ hybridization.
Figure 12:
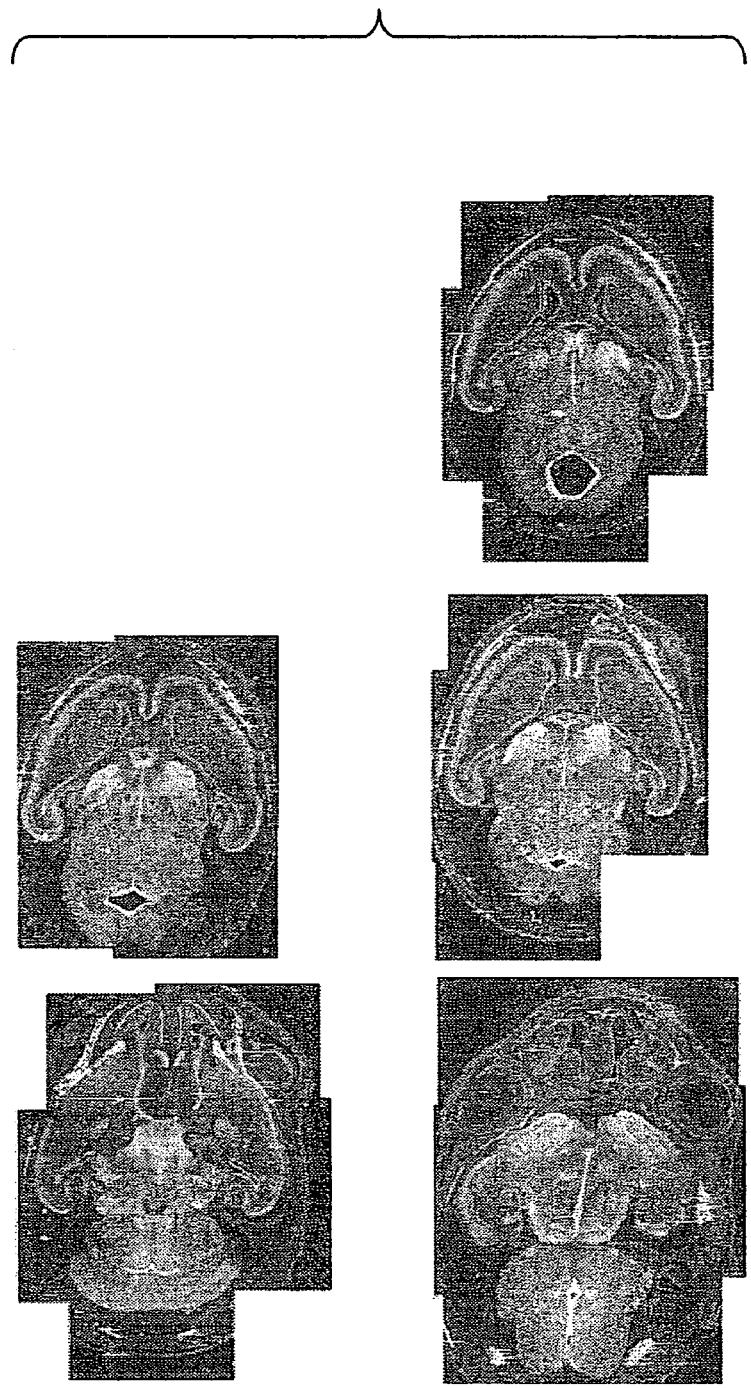
FIG. 12 is a series of photomicrographs showing the distribution of DL-2 mRNA in the brain of an E18 mouse by in situ hybridization.

The relative tissue distribution pattern of DRAGON, DL-2 and DL-1 mRNA in mouse embryos (E14.5) indicate that DRAGON and DL-2, but not DL-1, are primarily expressed in the nervous system, and that DRAGON and DL-2 expression in the nervous system is largely non-overlapping (FIGS. 9G-9L). DRAGON is heavily expressed in DRG neurons and in the dorso-medial mantle layer of the spinal cord, with lower expression laterally and ventrally. DL-2 shows no expression in the DRG but strong expression in the spinal cord and brain. In the spinal cord, DL-2 is expressed in the midline, extending from the roof to the floor plate around the central canal in the ependymal layer, medial and ventral to DRAGON (FIGS. 9C and 9F). DL-2-expressing neurons are also present in the marginal layer and ventral horn. A complementary DRAGON and DL-2 expression pattern is also present in embryonic brain. DRAGON is expressed in the alar plate of the myelencephalon, in the marginal layer of the mesencephalon, and with lower intensity laterally, in the basal plate of the pons, and in the cerebellar primordia. DL-2 is expressed in the ependymal layers of the myelencephalon, mesencephalon and pons. DL-2 but not DRAGON is expressed in the telencephalic cortex, most intensely medially. DRAGON is heavily expressed in the diencephalon, except in the ependymal layer where DL-2 is heavily expressed. DRAGON is homogeneously expressed in the striatum whereas DL-2 is only expressed on its medial surface (FIGS. 9G-9L). DRAGON, but not DL-2, is expressed in the cortex of the future olfactory lobe, retina and olfactory epithelium (FIGS. 11 and 12), Both DRAGON and DL-2 are expressed in the cochlea.

Figure 9:
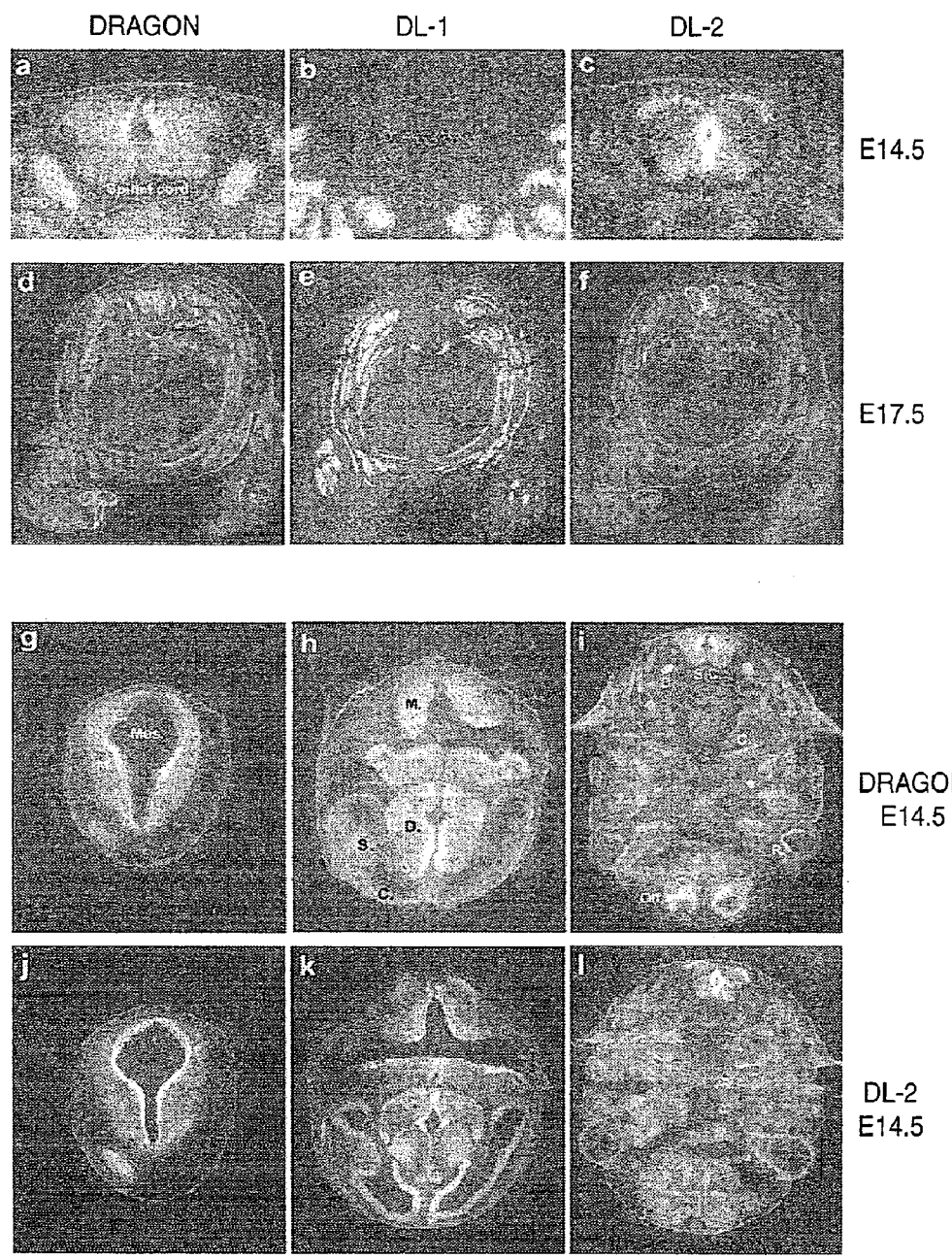
FIGS. 9A-9L are a series of photomicrographs showing, by in situ hybridization, the developmental distribution of DRAGON family members in the mouse embryo.

The mDL-1 gene has a very specific expression pattern in the developing mouse embryo. Expression was restricted to muscle and cartilage tissues distributed along the whole organism, indicating a role in muscle and bone development (FIGS. 9B and 9E). A structure-function analysis of the mDL-1 protein sequence indicated the presence of a signal peptide suggesting that mDL-1, like mDRAGON, is a secreted factor.

DRAGON Protein Expression

Figure 13A:
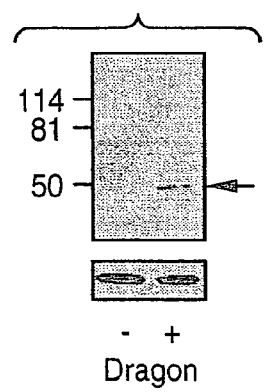
FIGS. 13A-13D provide experimental results using a novel anti-DRAGON rabbit polyclonal antibody.
Figure 13B:
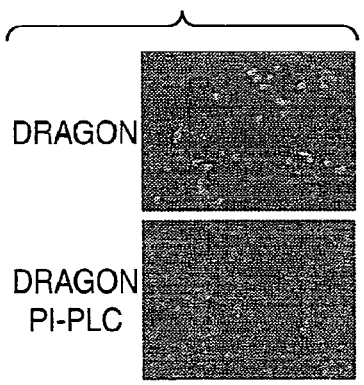
Figure 13C:
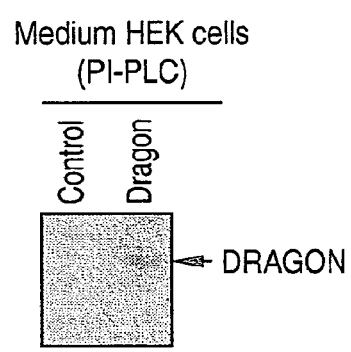

A rabbit polyclonal antibody was raised against the peptide sequence TAAAHSALEDVEALHPRK (SEQ ID NO: 11; residues 388-405 of mDRAGON), present in the C-terminus of DRAGON, upstream of its hydrophobic tail. The antibody binds with high affinity to recombinant DRAGON expressed in HEK293T transfected cells, recognizing a band of 50 KDa in Western blots (FIG. 13A). Antibody specificity was confirmed by immunocytochemistry of DRAGON-expressing HED293T cells (FIG. 13B). Western blots of protein extracts from neonatal and adult DRG and DRG primary cultures show a similar band with an additional lower band of 40 KDa, indicating possible proteolytic cleavage of endogenous DRAGON. Treatment of HEK293T cells expressing DRAGON with PI-PLC results in the decrease of DRAGON detection on HEK cells and its release into the culture medium (FIG. 13C), indicating that DRAGON is GPI-anchored.

Figure 13D:
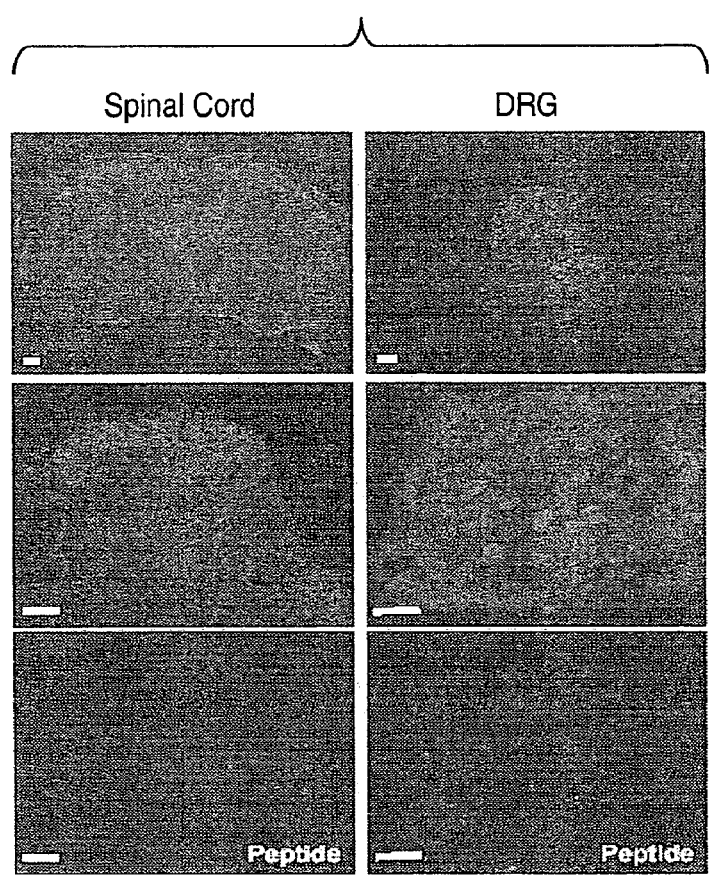
Figure 14A:
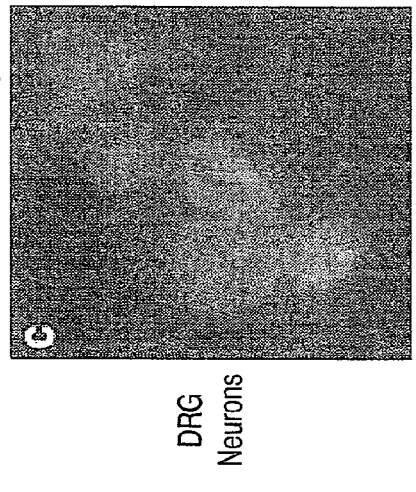
FIGS. 14A-14C are a series of photomicrographs that demonstrate the adhesion of DRG neurons to DRAGON-expressing HEK 293 cells. P14 neonatal DRG neurons were plated on a monolayer of confluent HEK cells and DRAGON transfected HEK cells. The culture slides were washed, fixed, and immunostained for DRG neurons using anti-NeuN (neuronal marker). Double immuno-labeling using anti-NeuN and anti-DRAGON indicates a direct interaction between DRAGON expressing HEK cells and DRG neurons (FIG. 14C).
Figure 14B:
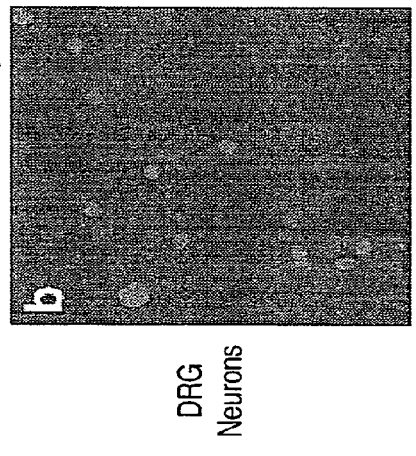
Figure 14C:
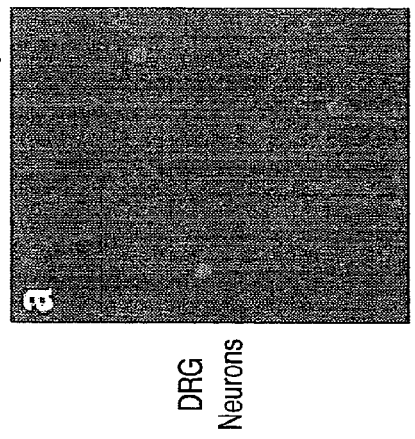
Figure 14D:
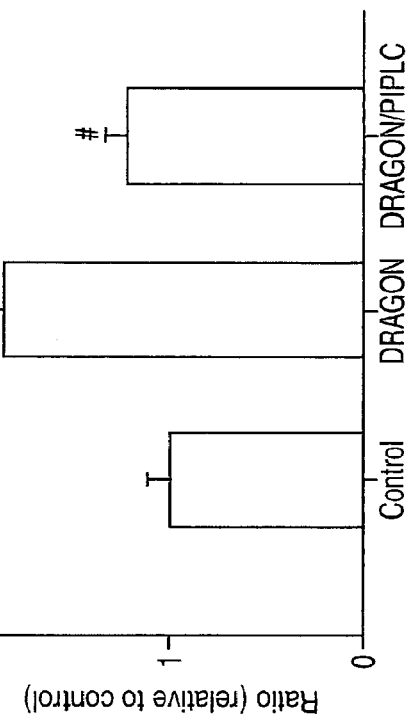
FIG. 14D is a bar graph quantifying the adhesion experiment results. A 1.9-fold increase in the number of adherent DRG neurons when plated on DRAGON-expressing HEK 293 cells, compared to control HEK 293 cells. Pretreatment of the DRAGON-expressing HEK cells with PI-PLC significantly reduced the adherence of DRG neurons.
Figure 18:
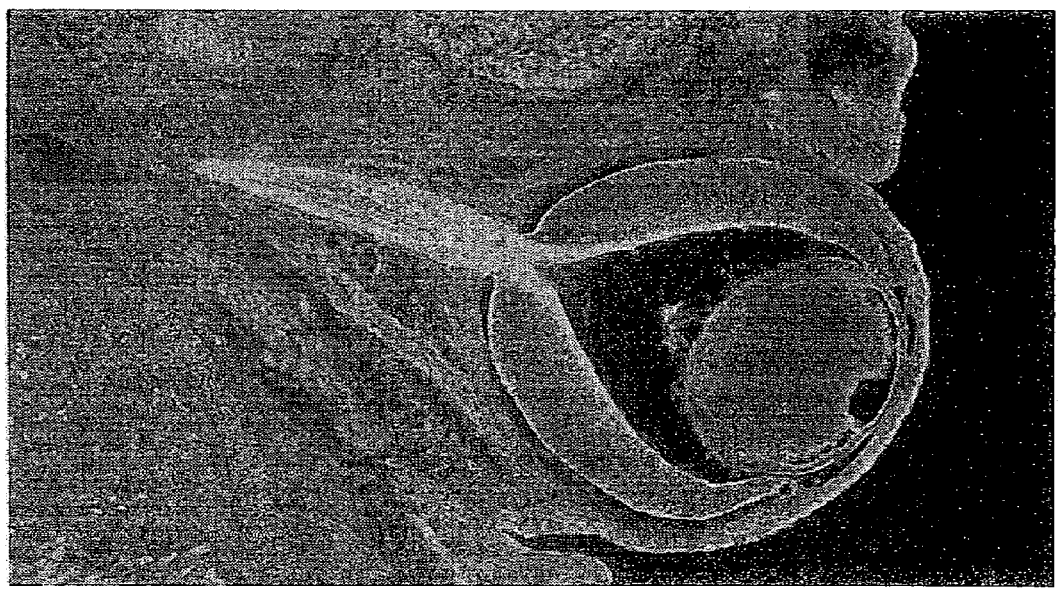
FIG. 18 is a photomicrograph showing the distribution of DRAGON expression in the retina and optic nerve of a mouse embryo (E14.5) using immunohistochemistry.
Figure 19:
FIG. 19 is a photomicrograph showing the distribution of DRAGON expression in rat glaborous skin (base of the epidermis of the hindpaw) using immunohistochemistry. DRAGON expression is highest in the Merkel cells.

Immunohistochemistry confirms expression of DRAGON in the DRG, spinal cord and brain in the areas where DRAGON mRNA is found (FIG. 13D). In the adult DRG, DRAGON is more abundantly expressed in small neurons with unmyelinated axons than in medium and large myelinated neurons (Aδ and Aβ-fibers) (FIG. 13D). In the adult spinal cord, DRAGON expression is most prominent in the superficial laminae of the dorsal horn (FIG. 13D). Immunohistochemical studies also demonstrated that the DRAGON protein is expressed in the E14.5 mouse retina and optic nerve (FIG. 18) and skin (FIG. 19).

DRAGON Promotes Cellular Adhesion

Cell surface GPI-anchored proteins, including the ephrins and tenascin, act as neuronal and non-neuronal cell adhesion molecules, binding to molecules expressed on neighboring cells or in the extracellular matrix. To examine whether DRAGON has a cell adhesion role, we measured the amount of adhesion between DRG neurons and HEK293 cells expressing recombinant DRAGON. DRAGON expression caused nearly a two-fold increase in the number of cultured DRG neurons that adhered to a monolayer of DRAGON-expressing HEK cells, compared to control HEK cells (FIGS. 14A-14D). Moreover, pretreatment of DRAGON-expressing HEK cells with PI-PLC resulted in only basal levels of DRG adhesion (FIGS. 14A-14D). These results may reflect homophilic or heterophilic DRAGON interactions with the endogenous DRAGON protein expressed on the surface of DRG neurons.

DRAGON Promotes Neuronal Survival

The anti-DRAGON polyclonal antibody was added to neonatal rat DRG neuronal cultures to investigate the contribution of DRAGON to neuronal survival. Neuronal cultures were treated with 0.25% anti-DRAGON serum, 0.25% pre-inunune serum (negative control), or vehicle. A statistically significant 20-25% increase in neuronal cell death was measured following anti-DRAGON treatment compared to controls.

|  | 0.25% anti-DRAGON serum | 0.25% pre-immune serum | Vehicle Control (no serum) |
| --- | --- | --- | --- |
| % viable neurons (mean) | 41.8% | 55.3% | 51.8% |
| Standard Error (S.E.) | 1.7% | 2.3% | 2.5% |
| Number of isolated DRG cultures (n) | 12 | 12 | 11 |

Neural Induction in *Xenopus* Embryos

Figure 15A:
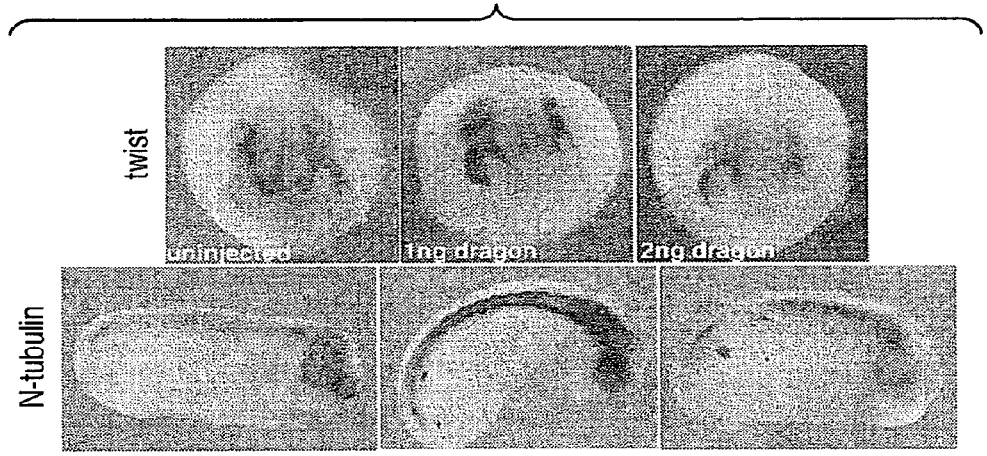
FIG. 15A is a series of photomicrographs demonstrating the effect of DRAGON overexpression in *Xenopus laevis*. Embryos were injected in the animal pole of 1 out of 2 cells at the 2-cell stage with DRAGON RNA and analyzed at late neurula (st23) for changes in neural crest patterning and early tadpole stages (st28) for ectopic induction of neural tissue. DRAGON overexpression inhibits twist RNA expression. However, DRAGON induces ectopic N-tubulin RNA expression.

In order to determine whether DRAGON affects cell differentiation and early embryonic development, DRAGON was injected into one cell at the animal pole of *Xenopus* embryos at the 2-cell stage. Embryos were allowed to develop until early tadpole stages. By injecting one out of two cells, a control side and an experimental side are present in the same embryo. A variety of markers were measured, including twist (expressed in anterior neural crest cells) and N-tubulin (a general neuronal differentiation marker), to determine whether DRAGON affects early neural patterning. Ectopic DRAGON caused a decrease in neural crest derivatives, as shown by loss of twist expression (FIG. 15A, top panels) and an increase in neuronal markers (FIG. 15A, bottom panels).

Figure 15B:
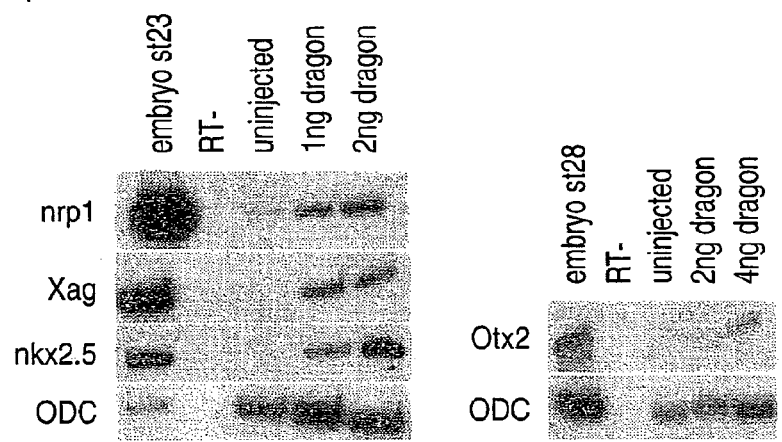
FIG. 15B is a Northern blot from animal cap explants demonstrating that DRAGON induces anterior neural markers, cement gland markers, and nkx2.5 (a cardiac marker).

In ectodermal explant assays, DRAGON induced anterior neural markers (FIG. 15B). Nrp1 is a pan-neural marker, Otx2 is expressed within the forebrain and midbrain regions, and XAG is expressed in the cement gland (the most anterior structure in the tadpole). In addition, DRAGON induced nkx2.5, an early marker of cardiac development.

Identification of Dragon Homologs in Other Species

Zebrafish Dragon Genes

The cDNA and polypeptide sequences of zebrafish homologs of DRAGON (SEQ ID NO: 25 and 28), DL-1 (SEQ ID NO: 26 and 29), and DL-2 (SEQ ID NO: 27 and 30) are provided. The sequence and domain structure of the three zebrafish genes are highly conserved with the mouse genes (70-75% homology) and Northern blot analysis shows a single transcript in each case. (FIG. 16A). DRAGON mRNA is present at the 2-4 cell stage of zebrafish embryogenesis, which is prior to initiation of zygotic transcription, suggesting a maternal or early developmental role for the protein. After the mid-blastula transition, the levels of DRAGON mRNA increase and are then maintained at a high level for up to 72 hours post fertilization, the latest stage examined (FIG. 16A).

In-situ hybridization reveals widespread and strong DRAGON expression in the zebrafish embryo. At the 18-somite stage, DRAGON is expressed along the midline in the telencephalon, diencephalon, and mesencephalon (FIGS. 16B and 16C). DRAGON is also expressed in the developing retina (FIG. 16D).

Overexpression of DRAGON in zebrafish embryos following sense injection into the fertilized egg, leads to abnormalities in the morphology of the brain and eye in 75-85% of treated embryos. The most common features include abnormal ventricle development, inappropriate cell death, particularly in the hindbrain, and neural tube twisting. DRAGON overexpression results in cyclopedia in 10-20% of embryos. The single eye is in an abnormally ventral location, with the anterior portion of the brain being dorsal to the eye (FIG. 16E-16G).

Embryos injected with a morpholine antisense oligonucleotide directed against the splice-donor site of the first exon of DRAGON show extensive CNS degeneration with a failure of development of the forebrain, hindbrain, and spinal cord (FIG. 16I-16M). The knockdown of DRAGON splicing and expression was confirmed by RT-PCR and compared to controls (FIG. 16H). Injected embryos had extensive apoptotic cell death in the brain, the brainstem and along the entire rostro-caudal extent of the spinal cord, as assessed by TUNEL assay and acridine orange staining. An inverted control oligonucleotide had no effect.

During early development, DL-1 shows high expression in the notochord and the adjacent adaxial cells (the earliest cells to develop into muscle fibers). Subsequently, DL-1 is expressed exclusively in the somites.

DL-2 mRNA first appears during zebrafish development at the three somite stage (approximately 10 hours postfertilization). DL-2 expression peaks at 18 hours, followed by a decrease over the next 72 hours.

Human Dragon Genes

The human homologs of all three murine Dragon gene family have been identified using the human genomic Celera database. The alignment of the human, mouse, and zebrafish DRAGON proteins is provided in FIG. 8B. The human homologs (SEQ ID NO: 8-10) are about 90% identical to the murine Dragon proteins (SEQ ID NO: 5-7).

C. Elegans DRAGON

Strong conservation of many domains present in members of the Dragon family among different species has also enabled us to identify the C. elegans ortholog (FIG. 17; SEQ ID NO: 18). The strong domain conservation pattern suggests a crucial role in development for the different members of this family.

Identification of Dragon Genes in Other Species

Homologs from other species can easily be identified based on sequence identity with the Dragon proteins and nucleic acids disclosed herein. Sequence identity may be measured using sequence analysis software on the default setting (e.g., Multiple sequences may also be aligned using the Clustal W(1.4) program (produced by Julie D. Thompson and Toby Gibson of the European Molecular Biology Laboratory, Germany and Desmond Higgins of European Bioinformatics Institute, Cambridge, UK) by setting the pairwise alignment mode to "slow," the pairwise alignment parameters to include an open gap penalty of 10.0 and an extend gap penalty of 0.1, as well as setting the similarity matrix to "blosum." In addition, the multiple alignment parameters may include an open gap penalty of 10.0, an extend gap penalty of 0.1, as well as setting the similarity matrix to "blosum," the delay divergent to 40%, and the gap distance to 8.

In Situ Hybridization

The in situ hybridization methods used herein have been described previously (Karchewski et al., J. Comp. Neurol. 413:327, 1999). Hybridization was performed on fresh frozen, mounted tissue sections from mouse embryo and adult rat dorsal root ganglia (DRG) using terminally-labeled oligonucleotide probes. Probes had approximately 50% G-C content and were complementary and selective for mDRAGON mRNAs. Probes were 3'-end labeled with $^{35}$S-dATP using a terminal transferase reaction and purified through a spin column (Qiagen). Hybridization was done under very high stringency conditions such that probe annealing required at least 90% sequence identity (Dagerlind et al., Histochemistry 98:39, 1992).

Briefly, slides were brought to room-temperature and covered with a hybridization solution (50% formamide, 1×Denhardt's solution, 1% sarcosyl, 10% dextran sulphate, 0.02M phosphate buffer, 4×SSC, 200 nM DTT, 500 mg/ml salmon sperm DNA) containing $10^7$ cpm/ml of labeled probe. Slides were incubated in a humidified chamber at 43° C. for 14-18 hours, then washed 4×15 min in 1×SSC at 55° C. In the final rinse, slides were brought to room temperature, washed in dH$_2$O, dehydrated in ethanol, and air dried.

Autoradiograms were generated by dipping slides in NTB2 nuclear track emulsion and storing in the dark at 4° C. Prior to conventional developing and fixation, sections were allowed to expose for 1-3 weeks, depending on the abundance of transcript. Unstained tissue was viewed under darkfield conditions using a fiber-optic darkfield stage adapter (MVI), while stained tissue was examined under brightfield conditions. Control experiments using sense probes were conducted to confirm the specificity of hybridization. The antisense oligonucleotide probes are as follows:

```
mDRAGON - specific for nucleotides 831-879 of SEQ ID NO: 1:
                                               (SEQ ID NO: 19)
5'-TCG CAC AAA CAC TGT GGT GCC TAT GTA GCG GGC ATG CAT CTC TAC GTA-3'.

mDL-1 - specific for nucleotides 913-960 of SEQ ID NO: 2:
                                               (SEQ ID NO: 20)
5'-CCC AGC TGT CTG TCG AAT GAT GAT AGT TGT TCC AAT GTA GGC AGC TCG-3' mDL-2 - specific for nucleotides 1252-1299 of SEQ ID NO: 3:
                                               (SEQ ID NO: 21)
5'-TTG CCA TCC TCC AAA GCA TAG TAG GCA GCC AGC GTG AAG TTC ACA TCA-3'.
```

Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

Synthesis of Dragon Proteins

Nucleic acids that encode Dragon family proteins or fragments thereof may be introduced into various cell types or cell-free systems for expression, thereby allowing purification of these Dragon proteins for biochemical characterization, large-scale production, antibody production, and patient therapy.

Eukaryotic and prokaryotic Dragon expression systems may be generated in which a Dragon family gene sequence is introduced into a plasmid or other vector, which is then used to transform living cells. Constructs in which the Dragon cDNA contains the entire open reading frame inserted in the correct orientation into an expression plasmid may be used for protein expression. Alternatively, portions of the Dragon gene sequences, including wild-type or mutant Dragon sequences, may be inserted. Prokaryotic and eukaryotic expression systems allow various important functional domains of the Dragon proteins to be recovered, if desired, as fusion proteins, and then used for binding, structural, and functional studies and also for the generation of appropriate antibodies.

Typical expression vectors contain promoters that direct the synthesis of large amounts of mRNA corresponding to the inserted Dragon nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of the Dragon nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Mammalian cells can also be used to express a Dragon protein. Stable or transient cell line clones can be made using Dragon expression vectors to produce Dragon proteins in a soluble (truncated and tagged) or membrane anchored (native) form. Appropriate cell lines include, for example, COS, HEK293T, CHO, or NIH cell lines.

Once the appropriate expression vectors containing a Dragon gene, fragment, fusion, or mutant are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. In vitro expression of Dragon proteins, fusions, polypeptide fragments, or mutants encoded by cloned DNA may also be used. Those skilled in the art of molecular biology will understand that a wide variety of expression systems and purification systems may be used to produce recombinant Dragon proteins and fragments thereof. Some of these systems are described, for example, in Ausubel et al. (supra).

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Polypeptides of the invention, particularly short Dragon fragments can also be produced by chemical synthesis (e.g., by the methods described in Solid Phase Peptide Synthesis, 2nd ed., 1984, The Pierce Chemical Co., Rockford, Ill.).

Dragon Fusion Proteins

Also included in the invention are Dragon family proteins fused to heterologous sequences, such as detectable markers (for example, proteins that may be detected directly or indirectly such as green fluorescent protein, hemagglutinin, or alkaline phosphatase), DNA binding domains (for example, GAL4 or LexA), gene activation domains (for example, GAL4 or VPI 6), purification tags, or secretion signal peptides. These fusion proteins may be produced by any standard method. For production of stable cell lines expressing a Dragon fusion protein, PCR-amplified Dragon nucleic acids may be cloned into the restriction site of a derivative of a mammalian expression vector. For example, KA, which is a derivative of pcDNA3 (Invitrogen, Carlsbad, Calif.) contains a DNA fragment encoding an influenza virus hemagglutinin (HA). Alternatively, vector derivatives encoding other tags, such as c-myc or poly Histidine tags, can be used.

The Dragon expression construct may be co-transfected, with a marker plasmid, into an appropriate mammalian cell line (e.g. COS, HEK293T, or NIH 3T3 cells) using, for example, LIPOFECTAMINE™ (Gibco-BRL, Gaithersburg, Md.) according to the manufacturer's instructions, or any other suitable transfection technique known in the art. Suitable transfection markers include, for example, f3-galactosidase or green fluorescent protein (GFP) expression plasmids or any plasmid that does not contain the same detectable marker as the Dragon fusion protein. The Dragon-expressing cells can be sorted and further cultured, or the tagged Dragon can be purified.

In one particular example, a DRAGON open reading frame (ORF) was amplified by polymerase chain reaction (PCR) using standard techniques and primers containing restriction sites (e.g. Sal I sites). The top strand primer consisted of the sequence 5'-ATA AGC TTA TGG GCG TGA GAG CAG CAC CTT CC-3' (SEQ ID NO: 22) and the bottom strand primer consisted of the sequence 5'-GAA GTC GAC GAA ACA ACT CCT ACA AAA AC-3' (SEQ IT) NO: 23). DRAGON cDNA was also amplified without the signal peptide and subcloned into a vector (pSecTagHis) having a strong secretion signal peptide. The same bottom strand primer was used (SEQ ID NO: 23); however, the top strand primer was substituted for one having the sequence 5'-CTC AAG CIT CAG CCT ACT CAA TGC CGA ATC-3' (SEQ ID NO: 24).

In another example, we generated DRAGON-alkaline phosphatase (AP) fusion protein using the mammalian expression vector, pAPtag-5' (Flanagan et al., Meth. Enzymol. 327:198-210, 2000). When expressed in mammalian cells (e.g. HEK 293), the DRAGON-AP fusion protein is secreted at high levels into the culture medium and is easily detected by the AP activity assay. The resulting DRAGON-AP fusion protein can be used to screen expression libraries to identify, clone, sequence, and characterize molecules which interact with DRAGON, such as cell surface receptors or endogenous DRAGON ligands. Of course, this method is broadly applicable to all Dragon-family proteins and can be used in conjunction with any number of suitable tags known in the art.

Interaction Trap Assays

Two-hybrid methods, and modifications thereof, may also be used to identify novel proteins that interact with Dragon-family proteins, and hence may be naturally occurring Dragon ligands or receptors. In addition, regulators of Dragon, e.g., proteins that interfere with or enhance the interaction between Dragon and other proteins, may be identified by the use of a three-hybrid system. Such assays are well-known to skilled artisans, and may be found, for example, in Ausubel et al. (supra).

Generation of Anti-Dragon Antibodies

In order to prepare polyclonal antibodies, Dragon family proteins, fragments, or fusion proteins containing defined portions of Dragon proteins may be synthesized in bacterial, fungal, or mammalian cells by expression of corresponding DNA sequences in a suitable cloning vehicle. The proteins can be purified, coupled to a carrier protein, mixed with Freund's adjuvant (to enhance stimulation of the antigenic response in an innoculated animal), and injected into rabbits or other laboratory animals. Following booster injections at bi-weekly intervals, the rabbits or other laboratory animals are then bled and the sera isolated. The sera can be used directly or can be purified prior to use by various methods, including affinity chromatography employing reagents such as Protein A-Sepharose, antigen-Sepharose, and anti-mouse-Ig-Sepharose. The sera can then be used to probe protein extracts from Dragon-expressing tissue electrophoretically fractionated on a polyacrylamide gel to identify Dragon proteins. Alternatively, synthetic peptides can be made that correspond to the antigenic portions of the protein and used to innoculate the animals. As described above, a polyclonal antibody against mDRAGON was created using, as the immunogenic DRAGON fragment, a polypeptide corresponding to residues 388-405 of SEQ ID NO: 5. Suitable immunogens for creating anti-hDRAGON antibodies include, for example, the polypeptide sequences encoded by residues 54-72, 277-294, or 385-408 of SEQ ID NO: 8.

Alternatively, monoclonal antibodies may be prepared using Dragon proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, New York, N.Y., 1981). Once produced, monoclonal antibodies are also tested for specific Dragon protein recognition by Western blot or immunoprecipitation analysis.

Antibodies of the invention may also be produced using Dragon amino acid sequences that do not reside within highly conserved regions, and that appear likely to be antigenic, as analyzed by criteria such as those provided by the Peptide Structure Program (Genetics Computer Group Sequence Analysis Package, Program Manual for the GCG Package, Version 7, 1991) using the algorithm of Jameson and Wolf (CABIOS 4:181, 1988).

Use of Dragon Proteins and Nucleic Acids in Diagnosis

Dragon family proteins may be used in diagnosing existing disorders or the propensity for developing disorders of the nervous system (DRAGON and DL-2) or bone, muscle, skin, joint, and cartilage tissue (DL-1), where a decrease or increase in the level of Dragon protein or nucleic acid production, relative to a control, provides an indication of a deleterious condition. Alternatively, a patient sample may be analyzed for one or more alterations in a Dragon nucleic acid sequence, compared to a wild-type Dragon sequence, using a mismatch detection approach. The alteration in the Dragon sequence need not be in a coding region. Alterations in, for example, promoter regions can result in alterations of Dragon protein levels and/or tissue distribution. Wild-type Dragon nucleic acid sequences for use in this assay include SEQ ID NO: 1-4 and 31-32.

Generally, these techniques involve PCR amplification of nucleic acid from the patient sample, followed by identification of the mutation (e.g., mismatch) by either altered hybridization, aberrant electrophoretic gel migration, binding or cleavage mediated by mismatch binding proteins, or direct nucleic acid sequencing. Any of these techniques may be used to facilitate mutant Dragon detection, and each is well known in the art (see, for example, Orita et al., Proc. Natl. Acad. Sci. USA 86:2766-2770, 1989; and Sheffield et al., Proc. Natl. Acad. Sci. USA 86:232-236, 1989).

Mismatch detection assays may be used to diagnose a Dragon nucleic acid-mediated predisposition to a nervous system, bone, muscle, skin or cartilage condition. For example, a patient heterozygous for a Dragon mutation may show no clinical symptoms and yet possess a higher than normal probability of developing one or more types of these diseases. Given this diagnosis, a patient may take precautions to control their exposure to adverse environmental factors and to carefully monitor their medical condition (for example, through frequent physical examinations). This type of Dragon diagnostic approach may also be used to detect Dragon nucleic acid mutations in prenatal screens.

Measurement of Dragon RNA is also a useful diagnostic. For example, a decrease in a Dragon mRNA or protein in a subject, relative to a control subject, would suggest a diagnosis of the presence or propensity for acquiring a disorder of the nervous system, or the bone, muscle, skin, or joint tissue. In addition, a decrease in Dragon mRNA or protein, relative to control, may correlate with a poor prognosis for treatment of these conditions using a non-Dragon therapy.

Levels of Dragon protein or nucleic acid expression may be assayed by any standard technique and compared to control samples showing normal Dragon protein or nucleic acid expression. For example, expression in a biological sample (e.g., a biopsy) may be monitored by standard Northern blot analysis, using, for example, probes designed from a Dragon nucleic acid. Measurement of such expression may be aided by PCR (see, e.g., Ausubel et at, supra; PCR Technology: Principles and Applications for DNA Amplification, ed., H. A. Ehrlich, Stockton Press, NY; and Yap and McGee, Nucl. Acids Res. 19:4294, 1991).

In yet another approach, immunoassays may be used to detect or monitor a Dragon protein in a biological sample. Dragon-specific polyclonal or monoclonal antibodies may be used in any standard immunoassay format (e.g., ELISA, Western blot, or RIA assay) to measure Dragon levels; again comparison is to wild-type Dragon levels. Examples of immunoassays are described, e.g., in Ausubel et al. (supra). Immunohistochemical techniques may also be utilized for Dragon detection. For example, a tissue sample may be obtained from a patient, and a section stained for the presence of a Dragon protein using an antibody against that protein and any standard detection system (e.g., one which includes a secondary antibody conjugated to horseradish peroxidase). General guidance regarding such techniques can be found in, e.g., Bancroft and Stevens (Theory and Practice of Histological Techniques, Churchill Livingstone, 1982) and Ausubel et al. (supra).

Identification of Candidate Compounds for Treatment of Dragon-Related Conditions A candidate compound that is beneficial in the treatment, stabilization, or prevention of a Dragon-related condition (e.g. disorders of the nervous system, retina, skin, and bone, muscle, joint, or cartilage tissue) can be identified by the methods of the present invention. A candidate compound can be identified for its ability to affect the biological activity of a Dragon protein or the expression of a Dragon gene or to mimic its action. Compounds that are identified by the methods of the present invention that increase the biological activity or expression levels of a Dragon protein or that compensate for the loss of Dragon protein activity or gene expression, for example, due to loss of the Dragon gene due to a genetic lesion, can be used in the treatment or prevention of a Dragon-related condition. A candidate compound identified by the present invention can mimic the biological activity of a Dragon protein, bind a Dragon protein, modulate (e.g., increase or decrease) transcription of a Dragon gene, or modulate translation of a Dragon mRNA.

Any number of methods are available for carrying out screening assays to identify new candidate compounds that promote the expression of a Dragon gene. In one working example, candidate compounds are added at varying concentrations to the culture medium of cultured cells expressing one of the Dragon nucleic acid sequences of the invention. Gene expression is then measured, for example, by microarray analysis, Northern blot analysis (Ausubel et al., supra), or RT-PCR, using any appropriate fragment prepared from the nucleic acid molecule as a hybridization probe. The level of Dragon gene expression in the presence of the candidate compound is compared to the level measured in a control culture medium lacking the candidate compound. A compound which promotes an increase in the expression of a Dragon gene is considered useful in the invention and may be used as a therapeutic to treat a human patient.

In another working example, the effect of candidate compounds may be measured at the level of Dragon protein production using the same general approach and standard immunological techniques, such as Western blotting or immunoprecipitation with an antibody specific for a Dragon protein. For example, immunoassays may be used to detect or monitor the expression of at least one of the polypeptides of the invention in an organism. Polyclonal or monoclonal antibodies that are capable of binding to a Dragon protein may be used in any standard immunoassay format (e.g., ELISA, Western blot, or RIA assay) to measure the level of the protein. In some embodiments, a compound that promotes an increase in Dragon expression or biological activity is considered particularly useful.

Expression of a reporter gene that is operably linked to a Dragon promoter can also be used to identify a candidate compound for treating or preventing a Dragon-related condition. Assays employing the detection of reporter gene products are extremely sensitive and readily amenable to automation, hence making them ideal for the design of high-throughput screens. Assays for reporter genes may employ, for example, colorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. A genomic DNA fragment carrying a Dragon-specific transcriptional control region (e.g., a promoter and/or enhancer) is first cloned using standard approaches (such as those described by Ausubel et at (supra). The DNA carrying the Dragon transcriptional control region is then inserted, by DNA subcloning, into a reporter vector, thereby placing a vector-encoded reporter gene under the control of the Dragon transcriptional control region. The activity of the Dragon transcriptional control region operably linked to the reporter gene can then be directly observed and quantified as a function of reporter gene activity in a reporter gene assay.

In one embodiment, for example, the Dragon transcriptional control region could be cloned upstream from a luciferase reporter gene within a reporter vector. This could be introduced into the test cells, along with an internal control reporter vector (e.g., a lacZ gene under the transcriptional regulation of the β-actin promoter). After the cells are exposed to the test compounds, reporter gene activity is measured and Dragon reporter gene activity is normalized to internal control reporter gene activity.

In addition, candidate compounds may be identified using any of the Dragon fusion proteins described above (e.g., as compounds that bind to those fusion proteins), or by any of the two-hybrid or three-hybrid assays described above.

A candidate compound identified by the methods of the present invention can be from natural as well as synthetic sources. Those skilled in the field of drug discovery and development will understand that the precise source of test extracts or compounds is not critical to the methods of the invention. Examples of such extracts or compounds include, but are not limited to, plant-, fungal-, prokaryotic-, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Use of Transgenic Animals to Identify a Candidate Compound

The present invention also provides methods for using transgenic and knockout animals that develop a Dragon-related condition and accurately recapitulate many of the features of the Dragon-related condition associated with loss or mutation of a Dragon gene. Desirably, the Dragon gene is used to produce the transgenic animal or the Dragon gene is the target of the knockout. However, other genes involved in or related to Dragon expression or activity, may also be used to produce transgenic animals so that the effect on a Dragon-related condition may be studied in this context.

A transgenic animal expressing a mutant Dragpn gene can be used to identify candidate compounds that are useful for the treatment or prevention of a Dragon-related condition. Transgenic animals expressing a conditional mutant Dragon gene (e.g., using a tetracycline regulatable system) can also be generated by methods well known to those skilled in the art; such methods are described in, for example, WO 94/29442, WO 96/40892, WO 96/01313, and Yamamoto et al.

(Cell 101:57-66, 2000). In addition, the knockout animal may be a conditional knockout using, for example, the FLP/FRT system described in, for example, U.S. Pat. No. 5,527,695, and in Lyznik et al. (Nucleic Acid Research 24:3784-3789, 1996) or the Cre-lox recombination system described, for example, in Kilby et al. (Trends in Genetics 9:413-421, 1993).

Transgenic animals may be made using standard techniques, such as those described in Sambrook et al., Molecular Cloning: A Laboratory Manual, Cold Spring Harbor Laboratory, N.Y., 1989). Any tissue specific promoter may direct the expression of any Dragon protein used in the invention, such as neuron-specific promoters, muscle-specific promoters, skin-specific promoters, retina-specific promoters, and bone-specific promoters.

The disclosed transgenic and knock-out animals may be used as research tools to determine genetic and physiological features of a Dragon-related condition, and for identifying compounds that can affect such conditions. Knockout animals also include animals where the normal Dragon gene(s) has been inactivated or removed and replaced with a polymorphic allele of this gene. These animals can serve as a model system for the risk of developing, treating, stabilizing, or preventing a Dragon-related condition that is associated with a Dragon gene polymorphism or mutation.

In general, a transgenic or knockout animal can be used to identify a candidate compound useful for treating or preventing a Dragon-related condition by contacting the transgenic or knockout animal with the candidate compound and comparing the presence, absence, or level of expression of genes, either at the RNA level or at the protein level, in tissue from a transgenic or knockout animal as described above, and tissue from a matching non-transgenic or knockout animal. Standard techniques for detecting RNA expression, e.g., by Northern blotting, or protein expression, e.g., by Western blotting, are well known in the art. The response to or progression of disease in a transgenic or knockout animal, as compared with non-transgenic or knockout animals can be used to identify compounds that may be effective therapeutics against a Dragon-related condition, such as nervous system disorders or disorders of muscle, skin, bone, or cartilage tissue. Transgenic and knockout animals can also be used to predict whether compounds identified as therapeutics will affect disease progression.

Any transgenic animal, or cells derived from these animals, may be constructed and used for compound screening. Preferable animal models include, without limitation, mice, rats, rabbits, and flies.

Regulation of Stem Cell Fate Using Dragon Family Proteins

Differentiation of stem cells, particularly ES cells, can be accomplished by exposing the cells to supraphysiological concentrations of Dragon proteins. Specifically, DRAGON or DL-2 can induce a stem cell to adopt a neuronal phenotype, whereas DL-1 promotes myogenic phenotypes. Stem cell differentiation may be accomplished using any appropriate technique. For example, transgenic stem cells overexpressing a Dragon protein can be created. Preferably, the Dragon gene is operably linked to an inducible promoter in order to control the timing and level of Dragon protein expression. Alternatively, stem cell differentiation can be done by the treatment with an exogenous Dragon protein. Typically, a recombinant Dragon protein is produced using a non-stem cell line (e.g., CEO cells), the Dragon protein is isolated, and the stem cells are treated in vitro with the protein.

Dragon-induced stem cell differentiation into neuronal phenotypes can be facilitated by blocking competing differentiation pathways (e.g., pathways that lead to differentiation into cell types of mesodermal or endoderrnal origin). Examples of these competing pathways include, but are not limited to, signaling pathways for TGF-β superfamily members (Nodal, Activin, and bone morphogenic proteins (BMPs) 2, 4, and 7), which have been shown to be important for endoderm and mesoderm differentiation (Nature Reviews Neurosci. 3: 271-280). By inhibiting any one of these TGF-β family members that lead to endoderm or mesoderm differentiation, differentiation into a cell of neuroectodermal origin is favored.

It will be apparent to one of skill in the art that the timing and extent of TGF-β pathway inhibition and overexpression or application of a Dragon protein will vary depending on the methods and dosages used. For example, inhibition of a of TGF-β pathway by gene knockout technology persists throughout the lifetime of an ES cell, whereas inhibition of the same pathway via antisense oligonucleotides is generally transient such that antisense oligonucleotides need to be reapplied. In the latter case, one of skill in the art would be able to readily determine when and how much of the antisense oligonucleotide to reapply to promote neuronal differentiation.

Stem cells that have been induced to differentiate along a neuronal (using DRAGON or DL-2) or myogenic (using DL-1) lineage can be transplanted into a patient in need of cell replacement therapy. For example, patients diagnosed as having neurodegenerative diseases (e.g., Alzheimer's disease, Parkinson's disease, and Huntington's disease) can be treated by transplanting, into affected brain regions, stem cells that have been induced to differentiate along a neuronal lineage by exposure to DRAGON or DL-2. Stem cells treated with DL-1 to induce myogenic differentiation can be transplanted into patients diagnosed as having a muscle wasting disease such as muscular dystrophy, myotonia congenital, or myotonic dystrophy.

Administration of a Dragon Protein or a Candidate Compound for the Treatment or Prevention of a Dragon-Related Condition The present invention also includes the administration of a Dragon family protein for the treatment or prevention of a Dragon-related condition. The administration of a biologically active Dragon protein that, regardless of its method of manufacture, retains full biological activity, can be envisioned as restoring Dragon biological activity in a patient lacking endogenous activity of a Dragon protein due to a loss or reduction of expression or biological activity, e.g., by mutation or loss of a Dragon gene or cells that normally express a Dragon.

Peptide agents of the invention, such as a Dragon protein, can be administered to a subject, e.g., a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in Remington's Pharmaceutical Sciences, (19th edition), ed. A. Gennaro, 1995, Mack Publishing Company, Easton, Pa.

Pharmaceutical formulations of a therapeutically effective amount of a peptide agent or candidate compound of the invention, or pharmaceutically acceptable salt-thereof, can be administered orally, parenterally (e.g. intramuscular, intraperitoneal, intravenous, or subcutaneous injection), or by intrathecal or intracerebroventricular injection in an admixture with a pharmaceutically acceptable carrier adapted for the route of administration.

Methods well known in the art for making formulations are found, for example, in Remington's Pharmaceutical Sciences (19th edition), ed. A. Gennaro, 1995, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The protein or candidate compound of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

The protein or candidate compound of the present invention can be prepared in any suitable manner. The protein or candidate compound can be isolated from naturally occurring sources, recombinantly produced, or produced synthetically, or produced by a combination of these methods. The synthesis of short peptides is well known in the art. See e.g. Stewart et al., Solid Phase Peptide Synthesis (Pierce Chemical Co., 2d ed., 1984).

Gene Therapy

Another example of how Dragon family polynucleotides of the invention can be effectively used in treatment is gene therapy. See, generally, for example, U.S. Pat. No. 5,399,346. The general principle is to introduce the polynucleotide, for example, a Dragon gene, into a target cell in a patient, and allow it to supplement the activity of the defective endogenous Dragon protein. Alternatively, a Dragon gene can be inserted into an embryonic or adult stem or progenitor cell to promote cell survival or induce differentiation into a particular cell fate.

Entry into the cell is facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in neuronal, bone, muscle, skin, joint, or cartilage cells, or a heterologous promoter that can be induced by a suitable agent.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Other embodiments are within the claims.

What is claimed is:

1. A substantially pure polypeptide comprising a fragment of at least 50 consecutive amino acids of a sequence selected from the group consisting of SEQ ID NO: 6, 9 and 29, wherein said polypeptide or fragment thereof lacks the C-terminal GPI anchor domain and is linked to a heterologous sequence.

2. The polypeptide of claim 1, wherein said fragment is recombinant.

3. The polypeptide of claim 1, wherein said fragment lacks the N-terminal signal sequence.

4. A pharmaceutical composition comprising the polypeptide of claim 1 and a pharmaceutically acceptable carrier.

* * * * *